US012344874B2

(12) United States Patent
Savile et al.

(10) Patent No.: US 12,344,874 B2
(45) Date of Patent: Jul. 1, 2025

(54) TRANSAMINASE BIOCATALYSTS

(71) Applicant: Codexis, Inc., Redwood City, CA (US)

(72) Inventors: Christopher K. Savile, Santa Clara, CA (US); Emily Mundorff, Garden City, NY (US); Jeffrey C. Moore, Westfield, NJ (US); Paul N. Devine, Tinton Falls, NJ (US); Jacob M. Janey, New York, NY (US)

(73) Assignee: Codexis, Inc., Redwood City, CA (US)

( * ) Notice: Subject to any disclaimer, the term of this patent is extended or adjusted under 35 U.S.C. 154(b) by 622 days.

(21) Appl. No.: 17/361,832

(22) Filed: Jun. 29, 2021

(65) Prior Publication Data

US 2021/0332399 A1 Oct. 28, 2021

Related U.S. Application Data

(60) Continuation of application No. 16/807,977, filed on Mar. 3, 2020, now Pat. No. 11,078,505, which is a continuation of application No. 16/195,227, filed on Nov. 19, 2018, now Pat. No. 10,619,176, which is a continuation of application No. 15/915,437, filed on Mar. 8, 2018, now Pat. No. 10,160,985, which is a division of application No. 15/376,837, filed on Dec. 13, 2016, now Pat. No. 9,944,963, which is a continuation of application No. 15/140,809, filed on Apr. 28, 2016, now Pat. No. 9,550,982, which is a division of application No. 14/818,885, filed on Aug. 5, 2015, now Pat. No. 9,353,355, which is a division of application No. 14/518,143, filed on Oct. 20, 2014, now Pat. No. 9,133,445, which is a division of application No. 13/604,323, filed on Sep. 5, 2012, now Pat. No. 8,889,380, which is a continuation of application No. 12/714,397, filed on Feb. 26, 2010, now Pat. No. 8,293,507.

(60) Provisional application No. 61/155,902, filed on Feb. 26, 2009.

(51) Int. Cl.

| | |
|---|---|
| ***C12N 9/00*** | (2006.01) |
| ***C12N 9/10*** | (2006.01) |
| ***C12N 15/52*** | (2006.01) |
| ***C12P 13/00*** | (2006.01) |
| ***C12P 17/18*** | (2006.01) |
| *C12N 15/62* | (2006.01) |

(52) U.S. Cl.

CPC .......... *C12P 17/182* (2013.01); *C12N 9/1096* (2013.01); *C12N 15/52* (2013.01); *C12P 13/001* (2013.01); *C12Y 206/01018* (2013.01); *C12N 15/62* (2013.01); *Y02P 20/52* (2015.11)

(58) Field of Classification Search

CPC .... C12N 9/1096; C12P 13/001; C12P 17/182; C12P 17/10; C12P 17/12; C12P 13/00; C12Y 206/01

USPC ........................................................ 435/193

See application file for complete search history.

(56) References Cited

U.S. PATENT DOCUMENTS

| | | | |
|---|---|---|---|
| 4,950,606 | A | 8/1990 | Stirling et al. |
| 5,169,780 | A | 12/1992 | Stirling et al. |
| 5,300,437 | A | 4/1994 | Stirling et al. |
| 5,346,828 | A | 9/1994 | Stirling et al. |
| 5,360,724 | A | 11/1994 | Matcham et al. |
| 5,866,512 | A | 2/1999 | Matcham et al. |
| 5,965,432 | A | 10/1999 | Kobayashi et al. |
| 6,107,521 | A | 8/2000 | Lin et al. |
| 6,117,679 | A | 9/2000 | Stemmer |
| 6,133,018 | A | 10/2000 | Wu et al. |
| 6,221,638 | B1 | 4/2001 | Yamada et al. |
| 6,344,351 | B2 | 2/2002 | Yamada et al. |
| 6,346,402 | B1 | 2/2002 | Iwasaki et al. |
| 6,376,246 | B1 | 4/2002 | Crameri et al. |
| 6,586,182 | B1 | 7/2003 | Patten et al. |
| 7,169,952 | B2 | 1/2007 | Yamada et al. |
| 7,172,885 | B2 | 2/2007 | Pannuri et al. |
| 7,326,708 | B2 | 2/2008 | Cypes et al. |
| 7,468,459 | B2 | 12/2008 | Xio et al. |
| 7,588,923 | B2 | 9/2009 | Fotheringham et al. |
| 8,293,507 | B2 | 10/2012 | Savile et al. |
| 8,889,380 | B2 | 11/2014 | Savile et al. |
| 9,133,445 | B2 | 9/2015 | Savile et al. |
| 9,353,355 | B2 | 5/2016 | Savile et al. |
| 9,550,982 | B2 | 1/2017 | Savile et al. |
| 9,944,963 | B2 | 4/2018 | Savile et al. |
| 10,160,985 | B2 | 12/2018 | Savile et al. |
| 10,619,176 | B2 | 4/2020 | Savile et al. |
| 2005/0153417 | A1 | 7/2005 | Davis et al. |
| 2006/0195947 | A1 | 8/2006 | Davis et al. |
| 2008/0220990 | A1 | 9/2008 | Fox |
| 2008/0248539 | A1 | 10/2008 | Giver et al. |
| 2009/0123983 | A1 | 5/2009 | Niddam-Hildesheim |

(Continued)

FOREIGN PATENT DOCUMENTS

| | | |
|---|---|---|
| EP | 1075534 B1 | 5/2005 |
| EP | 0857790 B1 | 8/2005 |

(Continued)

OTHER PUBLICATIONS

Cameron, M., et al., "The highly stereospecific enzyme catalysed transamination of 4-fluorophenylglyoxylic acid to 4-(S)-fluorephenylglycine", Journal of Molecular Catalysis, 14: 1-5, 2001.

(Continued)

*Primary Examiner* — Robert B Mondesi
*Assistant Examiner* — Mohammad Y Meah

(57) ABSTRACT

The present disclosure relates to polypeptides having transaminase activity, polynucleotides encoding the polypeptides, and methods of using the polypeptides.

9 Claims, No Drawings

Specification includes a Sequence Listing.

(56) References Cited

U.S. PATENT DOCUMENTS

| | | | |
|---|---|---|---|
| 2009/0192326 | A1 | 7/2009 | Perlman et al. |
| 2009/0221595 | A1 | 9/2009 | Perlman et al. |
| 2009/0246837 | A1 | 10/2009 | Robins et al. |
| 2009/0247532 | A1 | 10/2009 | Huang et al. |
| 2009/0312196 | A1 | 12/2009 | Colbeck et al. |

FOREIGN PATENT DOCUMENTS

| | | | |
|---|---|---|---|
| EP | 404146 | B1 | 3/2006 |
| EP | 1818411 | A1 | 8/2007 |
| EP | 1045025 | B1 | 10/2008 |
| EP | 0987332 | B1 | 8/2009 |
| EP | 1819825 | B1 | 1/2010 |
| JP | 63273486 | A | 11/1988 |
| KR | 2006007124 | A | 1/2006 |
| WO | 99/46398 | A1 | 9/1999 |
| WO | 2000/66760 | A1 | 11/2000 |
| WO | 2006/126498 | A1 | 11/2006 |
| WO | 2007/093372 | A1 | 8/2007 |
| WO | 2008/127646 | A2 | 10/2008 |
| WO | 2009/045507 | A2 | 4/2009 |
| WO | 2009/084024 | A2 | 7/2009 |
| WO | 2010/081053 | A2 | 7/2010 |

OTHER PUBLICATIONS

Cho, B.-K., et al., "Asymmetric Synthesis of L-Homophenylalanine by Equilibrium-Shift Using Recombinant Aromatic L-Amino Acid Transaminase", Biotechnology and Bioengineering, 83(2):226-234, 2003.

Cho, B.-K., et al., "Engineering Aromatic L-Amino Acid Transaminase for the Asymmetric Synthesis of Constrained Analogs of L-Phenylalanine", Biotechnology and Bioengineering, 94(5):842-850, 2006.

Cho, B.-K., et al., "Enzymatic Resolution for the Preparation of Enantiomerically Enriched D-β-Heterocyclic Alanine Derivatives Using *Escherichia coli* Aromatic L-Amino Acid Transaminase", Biotechnology and Bioengineering, 88 (4):512-519, 2004.

Cho, B.-K., et al., "Redesigning the Substrate Specificity of ω-Aminotransferase for the Kinetic Resolution of Aliphatic Chiral Amines", Biotechnology and Bioengineering, 99(2):275-284, 2008.

Cho, B.-K., et al., "Simultaneous Synthesis of Enantiomerically Pure (S)-Amino Acids and (R)-Amines Using Coupled Transaminase Reactions", Biotechnology and Bioengineering, 81(7):783-789, 2003.

Christen, P., et al., "From Cofactor to Enzymes. The Molecular Evolution of Pyridoxal-5'-Phosphate-Dependent Enzymes", The Chemical Record, 1:436-447, 2001.

Crump, S.P et al., "Biocatalytic Production of Amino Acids by Transamination", In Biocatalytic Production of Amino Acids and Derivatives; Rozzell, J. D., Wagner, F., Eds.; Wiley: New York, 1992; pp. 43-58.

Eliot, A.C., et al., "The Dual-Specific Active Site of 7,8-Diaminopelargonic Acid Synthase and the Effect of the R391A Mutation", Biochemistry, 41:12582-12589, 2002.

Fadnavis, N.W., et al., "Asymmetric synthesis of nonproteinogenic amino acids with L-amino acid transaminase: synthesis of (2S)-2-amino-4-oxo-4-phenylbutyric and (3E,2S)-2-amino-4-phenylbutenoic acids", Tetrahedron: Asymmetry, 17:2199-2202, 2006.

Fernandez, F.J., et al., "Structural Studies of the Catalytic Reaction Pathway of a Hyperthermophilic Histidinol-phosphate Aminotransferase", The Journal of Biological Chemistry, 279(20):21478-21488, 2004.

Goto, M., et al., "Crystal Structures of Branched-Chain Amino Acid Aminotransferase Complexed with Glutamate and Glutarate: True Reaction Intermediate and Double Substrate Recognition of the Enzyme", Biochemistry, 42:3725-3733, 2003.

Hansen, K.B., et al., "First generation process for the preparation of the DPP-IV inhibitor Sitagliptin", Organic Process Research & Development, 9:634-639, 2005.

Maruyama, K., et al., "Structures of *Escherichia coli* Histidinol-Phosphate Aminotransferase and Its Complexes with Histidinol-Phosphate and N-(5'-Phosphopyridoxyl)-L-Glutamate: Double Substrate Recognition of the Enzyme".

Hirotsu K., et al., "Dual Substrate Recognition of Aminotransferases", The Chemical Record, 5:160-172, 2005.

Höhne, M., et al., "Efficient Asymmetric Synthesis of Chiral Amines by Combining Transaminase and Pyruvate Decarboxylase", ChemBioChem, 9:363-365, 2008.

Hwang, B.-Y., et al., "High-throughput screening method for the identification of active and enantioselective ω- transaminases", Enzyme and Microbial Technology, 34:429-436, 2004.

Hwang, B.-Y., et al., "Revisit of aminotransferase in the genomic era and its application to biocatalysis", Journal of Molecular Catalysis B: Enzymatic, 37:47-55, 2005.

Hwang, J.-Y., et al., "Simultaneous Synthesis of 2-Phenylethanol and L-Homophenylalanine Using Aromatic Transaminase With Yeast Ehrlich Pathway", Biotechnology and Bioengineering, 102(5):1323-1329, 2009.

Iwasaki, A., et al., "Microbial synthesis of (R)- and (S)-3,4-dimethoxyamphetamines through stereoselective transamination", Biotechnology Letters, 24: 1845-1846, 2003.

Iwasaki, A., et al., "Microbial synthesis of chiral amines by (R)-specific transamination with *Arthrobacter* sp. KNK168", Applied Microbiology Biotechnology 69: 499-505, 2006.

Käck, H., et al., "Crystal Structure of Diaminopelargonic Acid Synthase: Evolutionary Relationships between Pyridoxal-5'-phosphate-dependent Enzymes", J. Mol. Biol., 291:857-876, 1999.

Koszelewski, D., et al., "Asymmetric Synthesis of Optically Pure Pharmacologically Relevant Amines Employing ω-Transaminases", Adv. Synth. Catal., 350:2761-2766, 2008.

Koszelewski, D., et al., "Deracemisation of α-Chiral Primary Amines by a One-Pot, Two-Step Cascade Reaction Catalysed by ω-Transaminases", Eur. J. Org. Chem., pp. 2289-2292, 2009.

Koszelewski, D., et al., "Formal Asymmetric Biocatalytic Reductive Amination", Agnew. Chem. Int. Ed., 47:9337-9340, 2008.

Koszelewski, D., et al., "Synthesis of Optically Active Amines Employing Recombinant ω-Transaminases in *E. coli* Cells", ChemCatChem, pp. 1-6, 2009.

Liu, W., et al., "Crystal Structures of Unbound and Aminooxyacetate-Bound *Escherichia coli* γ-Aminobutyrate Aminotransferase", Biochemistry, 43:10896-10905, 2004.

Liu, W., et al., "Kinetic and Crystallographic Analysis of Active Site Mutants of *Escherichia coli* γ-Aminobutyrate Aminotransferase", 44:2982-2992, 2005.

Matsui, I., et al., "The Molecular Structure of Hyperthermostable Aromatic Aminotransferase with Novel Substrate Specificity from Pyrococcus horikoshii", The Journal of Biological Chemistry, 275(7): 4871-4879, 2000.

Mihara, H., et al., "N-Methyl-L-amino acid dehydrogenase from Pseudomonas putida. A novel member of an unusual NAD(P)-dependent oxidoreductase superfamily", FEBS Journal, 272:1117-1123, 2005.

Nobe, Y., et al., "The Novel Substrate Recognition Mechanism Utilized by Aspartate Aminotransferase of the Extreme Thermophile Thermus thermophilus HB8", The Journal of Biological Chemistry, 273(45):29554-29564, 1998.

Noland, B.W., et al., "Structural Studies of *Salmonella typhimurium* ArnB (PmrH) Aminotransferase: A 4-Amino-4- Deoxy-L-Arabinose Lipopolysaccharide-Modifying Enzyme", Structure, 10:1569-1580, 2002.

Okada, K., et al., "Structures of *Escherichia coli* Branched-Chain Amino Acid Aminotransferase and Its Complexes with 4-Methylvalerate and 2-Methylleucine: Induced Fit and Substrate Recognition of the Enzyme", Biochemistry, 40:7453-7463, 2001.

Okada, K., et al., "Three-Dimensional Structure of *Escherichia coli* Branched-Chain Amino Acid Aminotransferase at 2.5 Å Resolution", J. Biochem., 121:637-641, 1997.

Okamoto, A., et al., "Crystal Structures of Paracoccus denitrificans Aromatic Amino Acid Aminotransferase: A Substrate Recognition Site Constructed by Rearrangement of Hydrogen Bond Network", J. Mol. Biol., 280:443-461, 1998.

(56) References Cited

OTHER PUBLICATIONS

Okamoto, A., et al., "The Active Site of Paracoccus denitrificans Aromatic Amino Acid Aminotransferase Has Contrary Properties: Flexibility and Rigidity", Biochemistry, 38:1176-1184, 1999.
Oue, S., et al., "Paracoccus denitrificans Aromatic Amino Acid Aminotransferase: A Model Enzyme for the Study of Dual Substrate Recognition Mechanism", J. Biochem, 121:161-171, 1997.
Peisach, D., et al., "Crystallographic Study of Steps along the Reaction Pathway of D-Amino Acid Aminotransferase", Biochemistry, 37:4958-4967, 1998.
Sandmark, J., et al., "Conserved and Nonconserved Residues in the Substrate Binding Site of 7,8-Diaminopelargonic Acid Synthase from *Escherichia coli* Are Essential for Catalysis", Biochemistry, 43:1213-1222, 2004.
Sandmark, J., et al., "Structural Basis for the Inhibition of the Biosynthesis of Biotin by the Antibiotic Amiclenomycin", The Journal of Biological Chemistry, 277(45):43352-43358, 2002.
Savile, C.K., et al., "Biocatalytic asymmetric synthesis of chiral amines from ketones applied to Sitagliptin manufacture", Science, 329: 205-309, including supporting materials, 2010.
Shin J.-S., et al., "Purification, characterization, and molecular cloning of a novel amine:pyruvate transaminase from Vibrio fluvialis JS17", Appl. Microbiol. Biotechnol., 61:463-471, 2003.
Shin, J.-S., et al., "Asymmetric Synthesis of Chiral Amines With ω-Transaminase", Biotechnology and Bioengineering, 65(2):206-211, 1999.
Shin, J.-S., et al., "Exploring the Active Site of Amine: Pyruvate Aminotransferase on the Basis of the Substrate Structure-Reactivity Relationship: How the Enzyme Controls Substrate Specificity and Stereoselectivity", J. Org. Chem., 67:2848-2853, 2002.
Sivaraman, J., et al., "Crystal Structure of Histidinol Phosphate Aminotransferase (HisC) from *Escherichia coli*, and its Covalent Complex with Pyridoxal-5'-phosphate and L-Histidinol Phosphate", J. Mol. Biol., 311:761-776, 2001.
Sugio, S., et al., "Crystal structures of L201A mutant of D-amino acid aminotransferase at 2.0 Å resolution: implication of the structural role of Leu201 in transamination", Protein Engineering, 11(8):613-619, 1998.
Taylor, P.P., et al., "Novel biosynthetic approaches to the production of unnatural amino acids using transaminases", Tibtech, 16:412-418, 1998.
Truppo, M.D., et al., "Efficient kinetic resolution of racemic amines using a transaminase in combination with an amino acid oxidase", Chemical Communications, pp. 2127-2129, 2009.
Truppo, M.D., et al., "Efficient production of chiral amines at concentrations of 50g/L using transaminases", Adv. Synth, Catal., 351:1-5, 2009.
Truppo, M.D., et al., "Rapid determination of both the activity and enantioselectivity of ketoreductases", Angew. Chem. Int. Ed. Engl., 47(14):2639-41, 2008.
Truppo, M.D., et al., "Rapid screening and scale-up of transaminase catalysed reactions," Organic & Biomolecular Chemistry, 7:395-398, 2009.
Truppo, M.D., "Rapid Screening and Process Development of Biocatalytic Reactions", Thesis submitted Univ. of Manchester, Faculty of Engineering and Physical Sciences, 1-296, 2009.
Ura, H., et al., "Substrate Recognition Mechanism of Thermophilic Dual-Substrate Enzyme", J. Biochem., 130:89-98, 2001.
Ura, H., et al., "Temperature Dependence of the Enzyme-Substrate Recognition Mechanism", J. Biochem., 129:173-178, 2001.
Van Ophem, P.W., et al., "Effects of the E177K Mutation in D-Amino Acid Transaminase. Studies on an Essential Coenzyme Anchoring Group That Contributes to Stereochemical Fidelity", Biochemistry, 38:1323-1331, 1999.
Yonaha, K., et al., "Properties of the Bound Coenzyme and Subunit Structure of ω-Amino Acid:Pyruvate Aminotransferase", The Journal of Biological Chemistry, 258(4):2660-2665, 1983.
Yun, H., et al., "Asymmetric synthesis of (S)-α-methylbenzylamine by recombinant *Escherichia coli* co-expressing omega-transaminase and acetolactate synthase", Biosci. Biotechnol. Biochem., 72(11):3030-3033, 2008.
Yun, H., et al., "Kinetic Resolution of (R,S)-sec-Butylamine Using Omega-Transaminase From Vibrio fluvialis JS17 Under Reduced Pressure", Biotechnology and Bioengineering, 87(6):772-778, 2004.
Yun, H., et al., "Synthesis of Enantiomerically Pure trans-(1R,2R)- and cis-(1S,2R)-1-Amino-2-Indanol by Lipase and ω-Transaminase", Biotechnology and Bioengineering, 93(2):391-395, 2006.
Yun, H., et al., "Use of Enrichment Culture for Directed Evolution of the Vibrio fluvialis JS17 ω-Transaminase, Which is Resistant to Product Inhibition by Aliphatic Ketones", Applied and Environmental Microbiology, 71(8):4220-4224, 2005.

SEQUENCE LISTING

```
<160> NUMBER OF SEQ ID NOS: 168

<210> SEQ ID NO 1
<211> LENGTH: 993
<212> TYPE: DNA
<213> ORGANISM: Artificial Sequence
<220> FEATURE:
<223> OTHER INFORMATION: ATA117

<400> SEQUENCE: 1

atggctttct ctgctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

ctgcactctg acgttaccta caccgttttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcattcgttt ctgtttctat cacccgtggt tactcttcta ccccaggtga acgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcagttcag    600

gaaacccacg accgtggttt cgaagctccg ctgctgctgg acggtgacgg tctgctggct    660

gaaggttctg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgcactaccg ctggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac taa                                 993


<210> SEQ ID NO 2
<211> LENGTH: 330
<212> TYPE: PRT
<213> ORGANISM: Artificial Sequence
<220> FEATURE:
<223> OTHER INFORMATION: ATA117

<400> SEQUENCE: 2

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Val Thr Tyr Thr Val Phe His Val Trp Asn Gly Asn Ala Phe Arg Leu
65                  70                  75                  80
```

```
Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Phe Val Ser Val Ser Ile Thr
        115                 120                 125

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Ser Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Ala Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 3
<211> LENGTH: 990
<212> TYPE: DNA
<213> ORGANISM: Artificial Sequence
<220> FEATURE:
<223> OTHER INFORMATION: Variant of ATA117

<400> SEQUENCE: 3

```
atggctttct ctgctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

ctgcactctg acgttaccta caccgggttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcagtcgttt ctgtttctat cacccgtggt tactcttcta ccccaggtga acgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcagttcag    600
```

```
gaaacccacg accgtggttt cgaagctccg ctgctgctgg acggtgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgcactaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

```
<210> SEQ ID NO 4
<211> LENGTH: 330
<212> TYPE: PRT
<213> ORGANISM: Artificial Sequence
<220> FEATURE:
<223> OTHER INFORMATION: Variant of ATA117

<400> SEQUENCE: 4

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Val Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Val Val Ser Val Ser Ile Thr
        115                 120                 125

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Gly Gly Gly Val Trp
        275                 280                 285

Pro Phe Val Ser Val Asp Gly Asn Pro Ile Ser Asp Gly Val Pro Gly
```

```
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 5
<211> LENGTH: 990
<212> TYPE: DNA
<213> ORGANISM: Artificial Sequence
<220> FEATURE:
<223> OTHER INFORMATION: Variant of ATA117

<400> SEQUENCE: 5

```
atggctttct ctgctgacac ctctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

ctgcactctg acgctaccta caccgggttc cacgtttgga acggtaacgc tttccgtctg     240

gacgaccaca tcgaacgtct gttctctaac gctgaatcta tgcgtatcat cccgccgctg     300

acccaggacg aagttaaaga aatcgctctg gaactggttg ctaaaaccga actgcgtgaa     360

gcaatcgttt ctgtttctat cacccgtggt tactcttcta ccccaggtga acgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcagttcag     600

gaaacccacg accgtggttt cgaagctccg ctgctgctgg acggtgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgacga agttctgggt     840

tgcactaccg ctggtggtgt ttggccgttc gtttctgttg acggtaaccc gatctctgac     900

ggtgttccgg gtccggttac ccagtctatc atccgtcgtt actgggaact gaacgttgaa     960

tcttcttctc tgctgacccc ggtacagtac                                      990
```

<210> SEQ ID NO 6
<211> LENGTH: 330
<212> TYPE: PRT
<213> ORGANISM: Artificial Sequence
<220> FEATURE:
<223> OTHER INFORMATION: Variant of ATA117

<400> SEQUENCE: 6

```
Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95
```

```
Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Ala Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 7
<211> LENGTH: 990
<212> TYPE: DNA
<213> ORGANISM: Artificial Sequence
<220> FEATURE:
<223> OTHER INFORMATION: Variant of ATA117

<400> SEQUENCE: 7

```
atggctttct ctgctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

ctgcactctg acgttaccta caccgttttc cacgtttgga acggtaacgc tttccgtctg    240

gacgaccaca tcgaacgtct gttctctaac gctgaatcta tgcgtatcat cccgccgctg    300

acccaagacg aagttaaaga aatcgctctg gaactggttg ctaaaaccga gctgcgtgaa    360

gcattagttt ctgtttctat cacccgtggt tactcttcta ccccaggtga acgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcagttcag    600

gaaacccacg accgtggttt cgaagctccg ctgctgctgg acggtgacgg tctgctggct    660

gaaggtccgg gtttcaacgt tgttgttatc aaagacggtg ttgttcgttc tccgggtcgt    720
```

```
gctgctctgc cgggcatcac ccgtaaaacc gttctggaaa tcgctgaatc tctgggtcac    780

gaagctatcc tggctgacat caccctggct gaactgctgg acgctgacga agttctgggt    840

tgcactaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

```
<210> SEQ ID NO 8
<211> LENGTH: 330
<212> TYPE: PRT
<213> ORGANISM: Artificial Sequence
<220> FEATURE:
<223> OTHER INFORMATION: Variant of ATA117

<400> SEQUENCE: 8

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Val Thr Tyr Thr Val Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Leu Val Ser Val Ser Ile Thr
        115                 120                 125

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
```

```
305                 310                 315                 320

Ser Ser Ser Leu Leu Thr Pro Val Gln Tyr
                325                 330


<210> SEQ ID NO 9
<211> LENGTH: 990
<212> TYPE: DNA
<213> ORGANISM: Artificial Sequence
<220> FEATURE:
<223> OTHER INFORMATION: Variant of ATA117

<400> SEQUENCE: 9

atggctttct ctgctgacac ctctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

ctgcactctg acgttaccta caccgttttc cacgtttgga acggtaacgc tttccgtctg     240

gacgaccaca tcgaacgtct gttctctaac gctgaatcta tgcgtatcat cccgccgctg     300

acccaggacg aagttaaaga aatcgctctg gaactggttg ctaaaaccga actgcgtgaa     360

gcaatcgttt ctgtttctat cacccgtggt tactcttcta ccccaggtga acgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcagttcag     600

gaaacccacg accgtggttt cgaagctccg ctgctgctgg acggtgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgacga agttctgggt     840

tgcactaccg gtggtggtgt ttggccgttc gtttctgttg acggtaaccc gatctctgac     900

ggtgttccgg gtccggttac ccagtctatc atccgtcgtt actgggaact gaacgttgaa     960

tcttcttctc tgctgacccc ggtacagtac                                      990


<210> SEQ ID NO 10
<211> LENGTH: 330
<212> TYPE: PRT
<213> ORGANISM: Artificial Sequence
<220> FEATURE:
<223> OTHER INFORMATION: Variant of ATA117

<400> SEQUENCE: 10

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Val Thr Tyr Thr Val Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110
```

```
Val Ala Lys Thr Glu Leu Arg Glu Ala Ile Val Ser Val Ser Ile Thr
        115                 120                 125

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 11
<211> LENGTH: 990
<212> TYPE: DNA
<213> ORGANISM: Artificial Sequence
<220> FEATURE:
<223> OTHER INFORMATION: Variant of ATA117

<400> SEQUENCE: 11

atggctttct ctgctgacac ctctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

ctgcactctg acgttaccta caccgttttc cacgtttgga acggtaacgc tttccgtctg     240

gacgaccaca tcgaacgtct gttctctaac gctgaatcta tgcgtatcat cccgccgctg     300

acccaggacg aagttaaaga aatcgctctg gaactggttg ctaaaaccga actgcgtgaa     360

gcattagttt ctgtttctat cacccgtggt tactcttcta ccccaggtga acgtgacatc     420

accaaacatc gtccgcaggt ttacatgtac gctgttccgt accagtggat cgtaccgttt     480

gaccgcatcc gtgacggtgt tcacgctatg gttgctcagg ctgttcgtcg tactccgcgt     540

tcttctatcg acccgcaggt taaaaacttc cagtggggtg acctgatccg tgcagttcag     600

gaaacccacg accgtggttt cgaagctccg ctgctgctgg acggtgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780
```

```
gaagctatcc tggctgacat caccctggct gaactgctgg acgctgacga agttctgggt    840

tgcactaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990


<210> SEQ ID NO 12
<211> LENGTH: 330
<212> TYPE: PRT
<213> ORGANISM: Artificial Sequence
<220> FEATURE:
<223> OTHER INFORMATION: Variant of ATA117

<400> SEQUENCE: 12

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Val Thr Tyr Thr Val Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Leu Val Ser Val Ser Ile Thr
        115                 120                 125

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ala Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
```

325 330

<210> SEQ ID NO 13
<211> LENGTH: 990
<212> TYPE: DNA
<213> ORGANISM: Artificial Sequence
<220> FEATURE:
<223> OTHER INFORMATION: Variant of ATA117

<400> SEQUENCE: 13
atggctttct ctgctgacac ctctgaaatc gtttacaccc acgacaccgg tctggactat 60
atcacctact ctgaccacga actggacccg gctaacccgc tggctggtgg tgctgcttgg 120
atcgaaggtg ctttcgttcc gccgtctgaa gctcgtatct ctatcttcga ccagggttac 180
ctgcactctg acgctaccta caccgggttc cacgtttgga acggtaacgc tttccgtctg 240
gacgaccaca tcgaacgtct gttctctaac gctgaatcta tgcgtatcat cccgccgctg 300
acccaggacg aagttaaaga aatcgctctg gaactggttg ctaaaaccga actgcgtgaa 360
gcaatcgttt ctgtttctat cacccgtggt tactcttcta ccccaggtga acgtgacatc 420
accaaacatc gtccgcaggt ttacatgtac gctgttccgt accagtggat cgtaccgttt 480
gaccgcatcc gtgacggtgt tcacgctatg gttgctcagt ctgttcgtcg tactccgcgt 540
tcttctatcg acccgcaggt taaaaacttc cagtggggtg acctgatccg tgcagttcag 600
gaaacccacg accgtggttt cgaggctccg ctgctgctgg acggtgacgg tctgctggct 660
gaaggtccgg gtttcaacgt tgttgttatc aaagacggtg ttgttcgttc tccgggtcgt 720
gctgctctgc cgggtatcac ccgtaaaacc gttctggaaa tcgctgaatc tctgggtcac 780
gaagctatcc tggctgacat caccctggct gaactgctgg acgctgacga agttctgggt 840
tgcactaccg gtggtggtgt ttggccgttc gtttctgttg acggtaaccc gatctctgac 900
ggtgttccgg gtccggttac ccagtctatc atccgtcgtt actgggaact gaacgttgaa 960
tcttcttctc tgctgacccc ggtacagtac 990

<210> SEQ ID NO 14
<211> LENGTH: 330
<212> TYPE: PRT
<213> ORGANISM: Artificial Sequence
<220> FEATURE:
<223> OTHER INFORMATION: Variant of ATA117

<400> SEQUENCE: 14

Met Ala Phe Ser Ala Asp Thr Ser Glu Ile Val Tyr Thr His Asp Thr
1 5 10 15

Gly Leu Asp Tyr Ile Thr Tyr Ser Asp His Glu Leu Asp Pro Ala Asn
20 25 30

Pro Leu Ala Gly Gly Ala Ala Trp Ile Glu Gly Ala Phe Val Pro Pro
35 40 45

Ser Glu Ala Arg Ile Ser Ile Phe Asp Gln Gly Tyr Leu His Ser Asp
50 55 60

Ala Thr Tyr Thr Gly Phe His Val Trp Asn Gly Asn Ala Phe Arg Leu
65 70 75 80

Asp Asp His Ile Glu Arg Leu Phe Ser Asn Ala Glu Ser Met Arg Ile
85 90 95

Ile Pro Pro Leu Thr Gln Asp Glu Val Lys Glu Ile Ala Leu Glu Leu
100 105 110

Val Ala Lys Thr Glu Leu Arg Glu Ala Ile Val Ser Val Ser Ile Thr
115 120 125

```
Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 15
<211> LENGTH: 990
<212> TYPE: DNA
<213> ORGANISM: Artificial Sequence
<220> FEATURE:
<223> OTHER INFORMATION: Variant of ATA117

<400> SEQUENCE: 15

```
atggctttct ctgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180

ctgacttctg acgctaccta caccgggttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcaatcgttt ctgtttctat cacccgtggt tactcttcta ccccaggtga acgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg ttctccgcgt    540

tcttctatcg acccgcaggt taaaaacttc cagtggggtg acctgatccg tgcatggcag    600

gaaacccacg accgtggttt cgaggctccg ctgctgctgg acggtgacgg tctgctggct    660

gaaggtccgg gttacaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900
```

```
ggtgttccgg gtccggttac ccagtctatc atccgtcgtt actgggaact gaacgttgaa    960

tcttcttctc tgctgacccc ggtacagtac                                     990


<210> SEQ ID NO 16
<211> LENGTH: 330
<212> TYPE: PRT
<213> ORGANISM: Artificial Sequence
<220> FEATURE:
<223> OTHER INFORMATION: Variant of ATA117

<400> SEQUENCE: 16

Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Ser Pro Arg Ser Ser Ile Asp Pro Gln Val Lys Asn Phe Gln Trp
            180                 185                 190

Gly Asp Leu Ile Arg Ala Trp Gln Glu Thr His Asp Arg Gly Phe Glu
        195                 200                 205

Ala Pro Leu Leu Leu Asp Gly Asp Gly Leu Leu Ala Glu Gly Pro Gly
    210                 215                 220

Tyr Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 17
<211> LENGTH: 990
<212> TYPE: DNA
<213> ORGANISM: Artificial Sequence
<220> FEATURE:
<223> OTHER INFORMATION: Variant of ATA117

<400> SEQUENCE: 17

```
atggctttct ctgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180

ctgttctctg acgctaccta caccgggttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcagtagttt ctgtttctat cacccgtggt tactcttcta ccccatatga gcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg acggtgacgg tctgctggct    660

gaaggtccgg gttacaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

<210> SEQ ID NO 18
<211> LENGTH: 330
<212> TYPE: PRT
<213> ORGANISM: Artificial Sequence
<220> FEATURE:
<223> OTHER INFORMATION: Variant of ATA117

<400> SEQUENCE: 18

```
Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Phe Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Val Val Ser Val Ser Ile Thr
        115                 120                 125

Arg Gly Tyr Ser Ser Thr Pro Tyr Glu Arg Asp Ile Thr Lys His Arg
    130                 135                 140
```

```
Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Tyr Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 19
<211> LENGTH: 990
<212> TYPE: DNA
<213> ORGANISM: Artificial Sequence
<220> FEATURE:
<223> OTHER INFORMATION: Variant of ATA117

<400> SEQUENCE: 19

```
atggctttct ctgctgacac ctctgaaatc gtttacaccc acgacaccgg tctggactat      60

atcacctact ctgaccacga actggacccg gctaacccgc tggctggtgg tgctgcttgg     120

atcgaaggtg ctttcgttcc gccgtctgaa gctcgtatct ctatcttcga ccagggttac     180

ctgacctctg acgctaccta caccgggttc cacgtttgga acggtaacgc tttccgtctg     240

gacgaccaca tcgaacgtct gttctctaac gctgaatcta tgcgtatcat cccgccgctg     300

acccaggacg aagttaaaga aatcgctctg gaactggttg ctaaaaccga actgcgtgaa     360

gcagtagttt ctgtttctat cacccgtggt tactcttcta ccccatatac tcgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcaattcag     600

gaaacccacg accgtggttt cgagctgccg ctgctgctgg acggtgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgatga agttctgggt     840

tgctcaaccg gtggtggtgt ttggccgttc gtttctgttg acggtaaccc gatctctgac     900

ggtgttccgg gtccggttac ccagtctatc atccgtcgtt actgggaact gaacgttgaa     960
```

tcttcttctc tgctgacccc ggtacagtac 990

<210> SEQ ID NO 20
<211> LENGTH: 330
<212> TYPE: PRT
<213> ORGANISM: Artificial Sequence
<220> FEATURE:
<223> OTHER INFORMATION: Variant of ATA117

<400> SEQUENCE: 20

Met Ala Phe Ser Ala Asp Thr Ser Glu Ile Val Tyr Thr His Asp Thr
1 5 10 15

Gly Leu Asp Tyr Ile Thr Tyr Ser Asp His Glu Leu Asp Pro Ala Asn
20 25 30

Pro Leu Ala Gly Gly Ala Ala Trp Ile Glu Gly Ala Phe Val Pro Pro
35 40 45

Ser Glu Ala Arg Ile Ser Ile Phe Asp Gln Gly Tyr Leu Thr Ser Asp
50 55 60

Ala Thr Tyr Thr Gly Phe His Val Trp Asn Gly Asn Ala Phe Arg Leu
65 70 75 80

Asp Asp His Ile Glu Arg Leu Phe Ser Asn Ala Glu Ser Met Arg Ile
85 90 95

Ile Pro Pro Leu Thr Gln Asp Glu Val Lys Glu Ile Ala Leu Glu Leu
100 105 110

Val Ala Lys Thr Glu Leu Arg Glu Ala Val Val Ser Val Ser Ile Thr
115 120 125

Arg Gly Tyr Ser Ser Thr Pro Tyr Thr Arg Asp Ile Thr Lys His Arg
130 135 140

Pro Gln Val Tyr Met Tyr Ala Val Pro Tyr Gln Trp Ile Val Pro Phe
145 150 155 160

Asp Arg Ile Arg Asp Gly Val His Ala Met Val Ala Gln Ser Val Arg
165 170 175

Arg Thr Pro Arg Ser Ser Ile Asp Pro Gln Val Lys Asn Phe Gln Trp
180 185 190

Gly Asp Leu Ile Arg Ala Ile Gln Glu Thr His Asp Arg Gly Phe Glu
195 200 205

Leu Pro Leu Leu Leu Asp Gly Asp Gly Leu Leu Ala Glu Gly Pro Gly
210 215 220

Phe Asn Val Val Val Ile Lys Asp Gly Val Val Arg Ser Pro Gly Arg
225 230 235 240

Ala Ala Leu Pro Gly Ile Thr Arg Lys Thr Val Leu Glu Ile Ala Glu
245 250 255

Ser Leu Gly His Glu Ala Ile Leu Ala Asp Ile Thr Leu Ala Glu Leu
260 265 270

Leu Asp Ala Asp Glu Val Leu Gly Cys Ser Thr Gly Gly Gly Val Trp
275 280 285

Pro Phe Val Ser Val Asp Gly Asn Pro Ile Ser Asp Gly Val Pro Gly
290 295 300

Pro Val Thr Gln Ser Ile Ile Arg Arg Tyr Trp Glu Leu Asn Val Glu
305 310 315 320

Ser Ser Ser Leu Leu Thr Pro Val Gln Tyr
325 330

<210> SEQ ID NO 21
<211> LENGTH: 990
<212> TYPE: DNA

<213> ORGANISM: Artificial Sequence
<220> FEATURE:
<223> OTHER INFORMATION: Variant of ATA117

<400> SEQUENCE: 21

```
atggctttct ctgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180

ctgacctctg acgctaccta caccgggttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcaatcgttt ctgtttctat cacccgtggt tactcttcta ccccatatat tcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg acggtgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

<210> SEQ ID NO 22
<211> LENGTH: 330
<212> TYPE: PRT
<213> ORGANISM: Artificial Sequence
<220> FEATURE:
<223> OTHER INFORMATION: Variant of ATA117

<400> SEQUENCE: 22

```
Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160
```

```
Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 23
<211> LENGTH: 990
<212> TYPE: DNA
<213> ORGANISM: Artificial Sequence
<220> FEATURE:
<223> OTHER INFORMATION: Variant of ATA117

<400> SEQUENCE: 23

atggctttct ctgctgacac ctctgaaatc gtttacaccc acgacaccgg tctggactat      60

atcacctact ctgaccacga actggacccg gctaacccgc tggctggtgg tgctgcttgg     120

atcgaaggtg ctttcgttcc gccgtctgaa gctcgtatct ctatcttcga ccagggttac     180

ctgacctctg acgctaccta caccgggttc cacgtttgga acggtaacgc tttccgtctg     240

gacgaccaca tcgaacgtct gttctctaac gctgaatcta tgcgtatcat cccgccgctg     300

acccaggacg aagttaaaga aatcgctctg gaactggttg ctaaaaccga actgcgtgaa     360

gcaatcgttt ctgtttctat cacccgtggt tactcttcta ccccatatac tcgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcaattcag     600

gaaacccacg accgtggttt cgagctgccg ctgctgctgg acggtgacgg tctgctggct     660

gaaggtccgg gttacaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgacga agttctgggt     840

tgctcaaccg gtggtggtgt ttggccgttc gtttctgttg acggtaaccc gatctctgac     900

ggtgttccgg gtccggttac ccagtctatc atccgtcgtt actgggaact gaacgttgaa     960

tcttcttctc tgctgacccc ggtacagtac                                      990
```

```
<210> SEQ ID NO 24
<211> LENGTH: 330
<212> TYPE: PRT
<213> ORGANISM: Artificial Sequence
<220> FEATURE:
<223> OTHER INFORMATION: Variant of ATA117

<400> SEQUENCE: 24

Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Tyr Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 25
<211> LENGTH: 990
<212> TYPE: DNA
<213> ORGANISM: Artificial Sequence
<220> FEATURE:
<223> OTHER INFORMATION: Variant of ATA117
```

<400> SEQUENCE: 25

```
atggctttct ctgctgacac ctctgaaatc gtttacaccc acgacaccgg tctggactat      60
atcacctact ctgaccacga actggacccg gctaacccgc tggctggtgg tgctgcttgg     120
atcgaaggtg ctttcgttcc gccgtctgaa gctcgtatct ctatcttcga ccagggttac     180
ctgcactctg acgctaccta caccgggttc cacgtttgga acggtaacgc tttccgtctg     240
gacgaccaca tcgaacgtct gttctctaac gctgaatcta tgcgtatcat cccgccgctg     300
acccaggacg aagttaaaga aatcgctctg gaactggttg ctaaaaccga actgcgtgaa     360
gcagtagttt ctgtttctat cacccgtggt tactcttcta ccccatatat tcgtgacatc     420
accaaacatc gtccgcaggt ttacatgtac gctgttccgt accagtggat cgtaccgttt     480
gaccgcatcc gtgacggtgt tcacgctatg gttgctcagg ccgttcgtcg tactccgcgt     540
tcttctatcg acccgcaggt taaaaacttc cagtggggtg acctgatccg tgcaattcag     600
gaaacccacg accgtggttt cgagctgccg ctgctgctgg acggtgacgg tctgctggct     660
gaaggtccgg gtttcaacgt tgttgttgtc aaagacggtg ttgttcgttc tccgggtcgt     720
gctgctctgc cgggtatcac ccgtaaaacc gttctggaaa tcgctgaatc tctgggtcac     780
gaagctatcc tggctgacat caccctggct gaactgctgg acgctgacga agttctgggt     840
tgcactaccg gtggtggtgt ttggccgttc gtttctgttg acggtaaccc gatctctgac     900
ggtgttccgg gtccggttac ccagtctatc atccgtcgtt actgggaact gaacgttgaa     960
tcttcttctc tgctgacccc ggtacagtac                                      990
```

<210> SEQ ID NO 26
<211> LENGTH: 330
<212> TYPE: PRT
<213> ORGANISM: Artificial Sequence
<220> FEATURE:
<223> OTHER INFORMATION: Variant of ATA117

<400> SEQUENCE: 26

```
Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Val Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ala Val Arg
                165                 170                 175
```

```
Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Phe Asn Val Val Val Val Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 27
<211> LENGTH: 990
<212> TYPE: DNA
<213> ORGANISM: Artificial Sequence
<220> FEATURE:
<223> OTHER INFORMATION: Variant of ATA117

<400> SEQUENCE: 27

atggctttct ctgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180

ctgacctctg acgctaccta caccgggttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcacatgttt ctgtttctat cacccgtggt tactcttcta ccccatatat tcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg acggtgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990


<210> SEQ ID NO 28
<211> LENGTH: 330
<212> TYPE: PRT
```

<213> ORGANISM: Artificial Sequence
<220> FEATURE:
<223> OTHER INFORMATION: Variant of ATA117

<400> SEQUENCE: 28

```
Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala His Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 29
<211> LENGTH: 990
<212> TYPE: DNA
<213> ORGANISM: Artificial Sequence
<220> FEATURE:
<223> OTHER INFORMATION: Variant of ATA117

<400> SEQUENCE: 29

```
atggctttct ctgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180

ctgacctctg acgctaccta caccacgttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcaatcgttt ctgtttctat cacccgtggt tactcttcta ccccatatat tcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg acggtgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                      990
```

<210> SEQ ID NO 30
<211> LENGTH: 330
<212> TYPE: PRT
<213> ORGANISM: Artificial Sequence
<220> FEATURE:
<223> OTHER INFORMATION: Variant of ATA117

<400> SEQUENCE: 30

```
Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Thr Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190
```

```
Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 31
<211> LENGTH: 990
<212> TYPE: DNA
<213> ORGANISM: Artificial Sequence
<220> FEATURE:
<223> OTHER INFORMATION: Variant of ATA117

<400> SEQUENCE: 31

```
atggctttct ctgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180

ctgacctctg acgctaccta cacctgtttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcaatcgttt ctgtttctat cacccgtggt tactcttcta ccccatatat tcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg acggtgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

<210> SEQ ID NO 32
<211> LENGTH: 330
<212> TYPE: PRT
<213> ORGANISM: Artificial Sequence
<220> FEATURE:
<223> OTHER INFORMATION: Variant of ATA117

<400> SEQUENCE: 32

```
Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Cys Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 33
<211> LENGTH: 990
<212> TYPE: DNA
<213> ORGANISM: Artificial Sequence
<220> FEATURE:
<223> OTHER INFORMATION: Variant of ATA117

<400> SEQUENCE: 33

```
atggctttct ctgctgacac ctctgaaatc gtttacaccc acgacaccgg tctggactat     60

atcacctact ctgaccacga actggacccg gctaacccgc tggctggtgg tgctgcttgg    120
```

atcgaaggtg ctttcgttcc gccgtctgaa gctcgtatct ctatcttcga ccagggttac 180
ctgacctctg acgctaccta caccgctttc cacgtttgga acggtaacgc tttccgtctg 240
gacgaccaca tcgaacgtct gttctctaac gctgaatcta tgcgtatcat cccgccgctg 300
acccaggacg aagttaaaga aatcgctctg gaactggttg ctaaaaccga actgcgtgaa 360
gcaatcgttt ctgtttctat cacccgtggt tactcttcta ccccatatat tcgtgacatc 420
accaaacatc gtccgcaggt ttacatgtac gctgttccgt accagtggat cgtaccgttt 480
gaccgcatcc gtgacggtgt tcacgctatg gttgctcagt ctgttcgtcg tactccgcgt 540
tcttctatcg acccgcaggt taaaaacttc cagtggggtg acctgatccg tgcaattcag 600
gaaacccacg accgtggttt cgagctgccg ctgctgctgg acggtgacgg tctgctggct 660
gaaggtccgg gtttcaacgt tgttgttatc aaagacggtg ttgttcgttc tccgggtcgt 720
gctgctctgc cgggtatcac ccgtaaaacc gttctggaaa tcgctgaatc tctgggtcac 780
gaagctatcc tggctgacat caccctggct gaactgctgg acgctgacga agttctgggt 840
tgctcaaccg gtggtggtgt ttggccgttc gtttctgttg acggtaaccc gatctctgac 900
ggtgttccgg gtccggttac ccagtctatc atccgtcgtt actgggaact gaacgttgaa 960
tcttcttctc tgctgacccc ggtacagtac 990

<210> SEQ ID NO 34
<211> LENGTH: 330
<212> TYPE: PRT
<213> ORGANISM: Artificial Sequence
<220> FEATURE:
<223> OTHER INFORMATION: Variant of ATA117

<400> SEQUENCE: 34

Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Ala Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

```
Leu Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

```
<210> SEQ ID NO 35
<211> LENGTH: 990
<212> TYPE: DNA
<213> ORGANISM: Artificial Sequence
<220> FEATURE:
<223> OTHER INFORMATION: Variant of ATA117

<400> SEQUENCE: 35

atggctttct ctgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180

tatacctctg acgctaccta caccgggttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcaatcgttt ctgtttctat cacccgtggt tactcttcta ccccatatat tcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg acggtgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

```
<210> SEQ ID NO 36
<211> LENGTH: 330
<212> TYPE: PRT
<213> ORGANISM: Artificial Sequence
<220> FEATURE:
<223> OTHER INFORMATION: Variant of ATA117

<400> SEQUENCE: 36
```

```
Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 37
<211> LENGTH: 990
<212> TYPE: DNA
<213> ORGANISM: Artificial Sequence
<220> FEATURE:
<223> OTHER INFORMATION: Variant of ATA117

<400> SEQUENCE: 37

```
atggctttct ctgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180
```

```
ctgtattctg acgctaccta caccgggttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcaatcgttt ctgtttctat cacccgtggt tactcttcta ccccatatat tcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg acggtgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                      990
```

<210> SEQ ID NO 38
<211> LENGTH: 330
<212> TYPE: PRT
<213> ORGANISM: Artificial Sequence
<220> FEATURE:
<223> OTHER INFORMATION: Variant of ATA117

<400> SEQUENCE: 38

```
Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Tyr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220
```

```
Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

```
<210> SEQ ID NO 39
<211> LENGTH: 990
<212> TYPE: DNA
<213> ORGANISM: Artificial Sequence
<220> FEATURE:
<223> OTHER INFORMATION: Variant of ATA117

<400> SEQUENCE: 39

atggctttct ctgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180

ctgacctctg acgctaccta caccgggttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcaatcgttt ctgtttctat cacccgtggt tactcttcta ccccatttat tcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg acggtgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ctggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

```
<210> SEQ ID NO 40
<211> LENGTH: 330
<212> TYPE: PRT
<213> ORGANISM: Artificial Sequence
<220> FEATURE:
<223> OTHER INFORMATION: Variant of ATA117

<400> SEQUENCE: 40

Met Ala Phe Ser Ala Asp Thr Ser Glu Ile Val Tyr Thr His Asp Thr
1               5                   10                  15
```

-continued

```
Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

```
<210> SEQ ID NO 41
<211> LENGTH: 990
<212> TYPE: DNA
<213> ORGANISM: Artificial Sequence
<220> FEATURE:
<223> OTHER INFORMATION: Variant of ATA117

<400> SEQUENCE: 41

atggcattct atgctgacac ctctgaaatc gtttacaccc acgacaccgg tctggactat      60

atcacctact ctgaccacga actggacccg gctaacccgc tggctggtgg tgctgcttgg     120

atcgaaggtg ctttcgttcc gccgtctgaa gctcgtatct ctatcttcga ccagggttac     180

ctgacctctg acgctaccta caccgggttc cacgtttgga acggtaacgc tttccgtctg     240

gacgaccaca tcgaacgtct gttctctaac gcggaatcta tccgtatcat cccgccgctg     300
```

```
acccaggacg aagttaaaga aatcgctctg gaactggttg ctaaaaccga actgcgtgaa    360

gcaatcgttt ctgtttctat cacccgtggt tactcttcta ccccgtatac gcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg actgcgatgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                      990
```

<210> SEQ ID NO 42
<211> LENGTH: 330
<212> TYPE: PRT
<213> ORGANISM: Artificial Sequence
<220> FEATURE:
<223> OTHER INFORMATION: Variant of ATA117

<400> SEQUENCE: 42

```
Met Ala Phe Tyr Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240
```

```
Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 43
<211> LENGTH: 990
<212> TYPE: DNA
<213> ORGANISM: Artificial Sequence
<220> FEATURE:
<223> OTHER INFORMATION: Variant of ATA117

<400> SEQUENCE: 43

atggcattct ctgctgacac ctctgaaatc gtttacaccc acgacaccgg tctggactat     60

atcacctatt cggactacga actggatccg gctaacccgc tggctggtgg tgctgcttgg    120

atcgaaggtg ctttcgttcc gccgtctgaa gctcgtatct ctatcttcga ccagggttac    180

ctgacctctg acgctaccta caccgggttc cacgtttgga acggtaacgc tttccgtctg    240

gacgaccaca tcgaacgtct gttctctaac gcggaatcta tccgtattat cccgccgctg    300

acccaggacg aagttaaaga aatcgctctg gaactggttg ctaaaaccga actgcgtgaa    360

gcaatcgttt ctgtttctat cacccgtggt tactcttcta ccccatatat tcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctaatccg tgcaattcag    600

gaaacccacg accgtggttt cgagctgccg ctgctgctgg actgcgatgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990


<210> SEQ ID NO 44
<211> LENGTH: 330
<212> TYPE: PRT
<213> ORGANISM: Artificial Sequence
<220> FEATURE:
<223> OTHER INFORMATION: Variant of ATA117

<400> SEQUENCE: 44

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30
```

```
Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

```
<210> SEQ ID NO 45
<211> LENGTH: 990
<212> TYPE: DNA
<213> ORGANISM: Artificial Sequence
<220> FEATURE:
<223> OTHER INFORMATION: Variant of ATA117

<400> SEQUENCE: 45

atggctttct cagctgacac ctctgaaatc gtttacaccc acgacaccgg tctggactat      60

atcacctatt cggactacga actggatccg gctaacccgc tggctggtgg tgctgcttgg     120

atcgaaggtg ctttcgttcc gccgtctgaa gctcgtatct ctatcttcga ccagggttac     180

ctgacctctg acgctaccta caccgggttc cacgtttgga acggtaacgc tttccgtctg     240

gacgaccaca tcgaacgtct gttctctaac gcggaatcta tccgtattat cccgccgctg     300

acccaggacg aagttaaaga gatcgctctg gaactggttg ctaaaaccga actgcgtgaa     360
```

```
gcaatcgttt ctgtttctat cacccgtggt tactcttcta ccccgtatac gcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg actgcgatgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

```
<210> SEQ ID NO 46
<211> LENGTH: 330
<212> TYPE: PRT
<213> ORGANISM: Artificial Sequence
<220> FEATURE:
<223> OTHER INFORMATION: Variant of ATA117

<400> SEQUENCE: 46

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255
```

```
Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 47
<211> LENGTH: 990
<212> TYPE: DNA
<213> ORGANISM: Artificial Sequence
<220> FEATURE:
<223> OTHER INFORMATION: Variant of ATA117

<400> SEQUENCE: 47

atggctttct cagctgacac ctctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

ctgacctctg acgctaccta cacctgtttc cacgtttgga acggtaacgc tttccgtctg     240

gacgaccaca tcgaacgtct gttctctaac gcggaatcta tccgtatcat cccgccgctg     300

acccaggacg aagttaaaga gatcgctctg gaactggttg ctaaaaccga actgcgtgaa     360

gcaatcgttt ctgtttctat cacccgtggt tactcttcta ccccatatac gcgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcaattcag     600

gaaacccacg accgtggttt cgagctgccg ctgctgctgg actgcgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgacga agttctgggt     840

tgctcaaccg gtggtggtgt ttggccgttc gtttctgttg acggtaaccc gatctctgac     900

ggtgttccgg gtccggttac ccagtctatc atccgtcgtt actgggaact gaacgttgaa     960

tcttcttctc tgctgacccc ggtacagtac                                      990


<210> SEQ ID NO 48
<211> LENGTH: 330
<212> TYPE: PRT
<213> ORGANISM: Artificial Sequence
<220> FEATURE:
<223> OTHER INFORMATION: Variant of ATA117

<400> SEQUENCE: 48

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45
```

```
Ser Glu Ala Arg Ile Ser Ile Phe Asp Gln Gly Tyr Leu Thr Ser Asp
    50                  55                  60

Ala Thr Tyr Thr Cys Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 49
<211> LENGTH: 990
<212> TYPE: DNA
<213> ORGANISM: Artificial Sequence
<220> FEATURE:
<223> OTHER INFORMATION: Variant of ATA117

<400> SEQUENCE: 49

```
atggctttct cagctgacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

ctgacctctg acgctaccta cacctgtttc cacgtttgga acggtaacgc tttccgtctg     240

gacgaccaca tcgaacgtct gttctctaac gcggaatcta tccgtatcat cccgccgctg     300

acccaggacg aagttaaaga gatcgctctg gaactggttg ctaaaaccga actgcgtgaa     360

gcaatcgttt ctgtttctat cacccgtggt tactcttcta ccccatatac gcgtgacatc     420

accaaacatc gtccgcaggt ttacatgtac gctgttccgt accagtggat cgtaccgttt     480
```

```
gaccgcatcc gtgacggtgt tcacgctatg gttgctcagt ctgttcgtcg tactccgcgt    540

tcttccatcg acccgcaggt taaaaacttc cagtggggtg acctgatccg tgcaattcag    600

gaaacccacg accgtggttt cgagctgccg ctgctgctgg actgcgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

```
<210> SEQ ID NO 50
<211> LENGTH: 330
<212> TYPE: PRT
<213> ORGANISM: Artificial Sequence
<220> FEATURE:
<223> OTHER INFORMATION: Variant of ATA117

<400> SEQUENCE: 50

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Cys Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270
```

```
Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 51
<211> LENGTH: 990
<212> TYPE: DNA
<213> ORGANISM: Artificial Sequence
<220> FEATURE:
<223> OTHER INFORMATION: Variant of ATA117

<400> SEQUENCE: 51

atggctttct cagctgacac ctctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

tatacttctg acgctaccta cacctccttc cacgtttgga acggtaacgc tttccgtctg     240

gacgaccaca tcgaacgtct gttctctaac gcggaatcta tccgtatcat cccgccgctg     300

acccaggacg aagttaaaga gatcgctctg gaactggttg ctaaaaccga actgcgtgaa     360

gcaatcgttt ctgtttctat cacccgtggt tactcttcta ccccattcac acgtgacatc     420

accaaacatc gtccgcaggt ttacatgtac gctattccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcaattcag     600

gaaacccacg accgtggttt cgagctgccg ctgctgctgg actgcgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgacga agttctgggt     840

tgctcaaccg gtggtggtgt ttggccgttc gtttctgttg acggtaaccc gatctctgac     900

ggtgttccgg gtccggttac ccagtctatc atccgtcgtt actgggaact gaacgttgaa     960

tcttcttctc tgctgacccc ggtacagtac                                      990


<210> SEQ ID NO 52
<211> LENGTH: 330
<212> TYPE: PRT
<213> ORGANISM: Artificial Sequence
<220> FEATURE:
<223> OTHER INFORMATION: Variant of ATA117

<400> SEQUENCE: 52

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60
```

```
Ala Thr Tyr Thr Ser Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Thr Arg Asp Ile Thr Lys His Arg
    130                 135                 140

Pro Gln Val Tyr Met Tyr Ala Ile Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 53
<211> LENGTH: 990
<212> TYPE: DNA
<213> ORGANISM: Artificial Sequence
<220> FEATURE:
<223> OTHER INFORMATION: Variant of ATA117

<400> SEQUENCE: 53

```
atggctttct cagctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

tatacttctg acgctaccta cacctgtttc cacgtttgga acggtaacgc tttccgtctg    240

gacgaccaca tcgaacgtct gttctctaac gcggaatcta tccgtatcat cccgccgctg    300

acccaggacg aagttaaaga gatcgctctg gaactggttg ctaaaaccga actgcgtgaa    360

gcagtggttt ctgtttctat cacccgtggt tactcttcta ccccattcac acgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540
```

```
tcttctatcg acccgcaggt taaaaacttc cagtggggtg acctgatccg tgcaattcag    600

gaaacccacg accgtggttt cgagctgccg ctgctgctgg actgcgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990


<210> SEQ ID NO 54
<211> LENGTH: 330
<212> TYPE: PRT
<213> ORGANISM: Artificial Sequence
<220> FEATURE:
<223> OTHER INFORMATION: Variant of ATA117

<400> SEQUENCE: 54

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Cys Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Val Val Ser Val Ser Ile Thr
        115                 120                 125

Arg Gly Tyr Ser Ser Thr Pro Phe Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285
```

```
Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 55
<211> LENGTH: 990
<212> TYPE: DNA
<213> ORGANISM: Artificial Sequence
<220> FEATURE:
<223> OTHER INFORMATION: Variant of ATA117

<400> SEQUENCE: 55

atggctttct cagctgacac ctctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

tatacttctg acgctaccta caccaccttc cacgtttgga acggtaacgc tttccgtctg     240

gacgaccaca tcgaacgtct gttctctaac gcggaatcta tccgtatcat cccgccgctg     300

actcaggacg aagttaaaga gatcgctctg gaactggttg ctaaaaccga actgcgtgaa     360

gcagtggttt ctgtttctat cacccgtggt tactcttcta ccccattcac acgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcaattcag     600

gaaacccacg accgtggttt cgagctgccg ctgctgctgg actgcgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgacga agttctgggt     840

tgctcaaccg gtggtggtgt ttggccgttc gtttctgttg acggtaaccc gatctctgac     900

ggtgttccgg gtccggttac ccagtctatc atccgtcgtt actgggaact gaacgttgaa     960

tcttcttctc tgctgacccc ggtacagtac                                      990


<210> SEQ ID NO 56
<211> LENGTH: 330
<212> TYPE: PRT
<213> ORGANISM: Artificial Sequence
<220> FEATURE:
<223> OTHER INFORMATION: Variant of ATA117

<400> SEQUENCE: 56

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Thr Phe His Val Trp Asn Gly Asn Ala Phe Arg Leu
65                  70                  75                  80
```

```
Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Val Val Ser Val Ser Ile Thr
        115                 120                 125

Arg Gly Tyr Ser Ser Thr Pro Phe Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 57
<211> LENGTH: 990
<212> TYPE: DNA
<213> ORGANISM: Artificial Sequence
<220> FEATURE:
<223> OTHER INFORMATION: Variant of ATA117

<400> SEQUENCE: 57

```
atggctttct cagctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

tatacttctg acgctaccta caccaccttc cacgtttgga acggtaacgc tttccgtctg    240

gacgaccaca tcgaacgtct gttctctaac gcggaatcta tccgtatcat cccgccgctg    300

acccaggacg aagttaaaga gatcgctctg gaactggttg ctaaaaccga actgcgtgaa    360

gcaatcgttt ctgtttctat cacccgtggt tactcttcta ccccattcga gcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg actgcgacgg tctgctggct    660
```

```
gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                      990
```

<210> SEQ ID NO 58
<211> LENGTH: 330
<212> TYPE: PRT
<213> ORGANISM: Artificial Sequence
<220> FEATURE:
<223> OTHER INFORMATION: Variant of ATA117

<400> SEQUENCE: 58

```
Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Thr Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300
```

```
Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 59
<211> LENGTH: 990
<212> TYPE: DNA
<213> ORGANISM: Artificial Sequence
<220> FEATURE:
<223> OTHER INFORMATION: Variant of ATA117

<400> SEQUENCE: 59

atggctttct cagctgacac ctctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

tatacttctg acgctaccta caccaccttc cacgtttgga acggtaacgc tttccgtctg     240

gacgaccaca tcgaacgtct gttctctaac gcggaatcta tccgtatcat cccgccgctg     300

acccaggacg aagttaaaga gatcgctctg gaactggttg ctaaaaccga actgcgtgaa     360

gcacatgttt ctgtttctat cacccgtggt tactcttcta ccccattcga gcgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcaattcag     600

gaaacccacg accgtggttt cgagctgccg ctgctgctgg actgcgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgacga agttctgggt     840

tgctcaaccg gtggtggtgt ttggccgttc gtttctgttg acggtaaccc gatctctgac     900

ggtgttccgg gtccggttac ccagtctatc atccgtcgtt actgggaact gaacgttgaa     960

tcttcttctc tgctgacccc ggtacagtac                                      990


<210> SEQ ID NO 60
<211> LENGTH: 330
<212> TYPE: PRT
<213> ORGANISM: Artificial Sequence
<220> FEATURE:
<223> OTHER INFORMATION: Variant of ATA117

<400> SEQUENCE: 60

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Thr Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95
```

```
Ile Pro Pro Leu Thr Gln Asp Glu Val Lys Glu Ile Ala Leu Glu Leu
            100                 105                 110

Val Ala Lys Thr Glu Leu Arg Glu Ala His Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

```
<210> SEQ ID NO 61
<211> LENGTH: 990
<212> TYPE: DNA
<213> ORGANISM: Artificial Sequence
<220> FEATURE:
<223> OTHER INFORMATION: Variant of ATA117

<400> SEQUENCE: 61

atggctttct cagctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

tatacctctg acgctaccta cacctgtttc cacgtttgga acggtaacgc tttccgtctg    240

gacgaccaca tcgaacgtct gttctctaac gcggaatcta tccgtatcat cccgccgctg    300

acccaggacg aagttaaaga gatcgctctg gaactggttg ctaaaaccga actgcgtgaa    360

gcaatcgttt ctgtttctat cacccgtggt tactcttcta ccccatatac gcgtgacatc    420

accaaacatc gtccgcaggt ttacatgtac gctgttccgt accagtggat cgtaccgtta    480

gaccgcatcc gtgacggtgt tcacttaatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg actgcgacgg tctgctggct    660

gaaggtccgg gtttcaacgt tgttgttatc aaagacggtg ttgttcgttc tccgggtcgt    720
```

```
gctgctctgc cgggtatcac ccgtaaaacc gttctggaaa tcgctgaatc tctgggtcac    780

gaagctatcc tggctgacat caccccggct gaactgctgg acgctgacga agttctgggt    840

tgctcaaccg gtggtggtgt ttggccgttc gtttctgttg acggtaaccc gatctctgac    900

ggtgttccgg gtccggtaac ccagtctatc atccgtcgtt actgggaact gaacgttgaa    960

tcttcttctc tgctgacccc ggtacagtac                                     990
```

```
<210> SEQ ID NO 62
<211> LENGTH: 330
<212> TYPE: PRT
<213> ORGANISM: Artificial Sequence
<220> FEATURE:
<223> OTHER INFORMATION: Variant of ATA117

<400> SEQUENCE: 62

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Cys Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Thr Arg Asp Ile Thr Lys His Arg
    130                 135                 140

Pro Gln Val Tyr Met Tyr Ala Val Pro Tyr Gln Trp Ile Val Pro Leu
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320
```

```
Ser Ser Ser Leu Leu Thr Pro Val Gln Tyr
                325                 330


<210> SEQ ID NO 63
<211> LENGTH: 990
<212> TYPE: DNA
<213> ORGANISM: Artificial Sequence
<220> FEATURE:
<223> OTHER INFORMATION: Variant of ATA117

<400> SEQUENCE: 63

atggctttct cagctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

tatacctctg acgctaccta cacctgtttc cacgtttgga acggtaacgc tttccgtctg    240

gacgaccaca tcgaacgtct gttctctaac gcggaatctc tgcgtatcat cccgccgctg    300

acccaggacg aagttaaaga gatcgctctg gaactggttg ctaaaaccga actgcgtgaa    360

gcaatcgttt ctgtttctat cacccgtggt tactcttcta ccccatatac gcgtgacatc    420

accaaacatc gtccgcaggt ttacatgtac gctgttccgt accagtggat cgtaccgttt    480

gaccgcatcc gtgacggtgt tcacttaatg gttgctcagt ctgttcgtcg tacgccgcgt    540

agctctatcg acccgcaggt taaaaacttc cagtggggtg acctgatccg tgcaattcag    600

gaaacccacg accgtggttt cgagctgccg ctgctgctgg actgcgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccttggct gaactgctgg acgctgacga agttctgggt    840

tgctcaaccg gtggtggtgt ttggccgttc gtttctgttg acggtaaccc gatctctgac    900

ggtgttccgg gtccgttaac ccagtctatc atccgtcgtt actgggaact gaacgttgaa    960

tcttcttctc tgctgacccc ggtacagtac                                     990


<210> SEQ ID NO 64
<211> LENGTH: 330
<212> TYPE: PRT
<213> ORGANISM: Artificial Sequence
<220> FEATURE:
<223> OTHER INFORMATION: Variant of ATA117

<400> SEQUENCE: 64

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Cys Phe His Val Trp Asn Gly Asn Ala Phe Arg Leu
65                  70                  75                  80

Asp Asp His Ile Glu Arg Leu Phe Ser Asn Ala Glu Ser Leu Arg Ile
                85                  90                  95

Ile Pro Pro Leu Thr Gln Asp Glu Val Lys Glu Ile Ala Leu Glu Leu
            100                 105                 110
```

```
Val Ala Lys Thr Glu Leu Arg Glu Ala Ile Val Ser Val Ser Ile Thr
        115                 120                 125

Arg Gly Tyr Ser Ser Thr Pro Tyr Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Leu Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 65
<211> LENGTH: 990
<212> TYPE: DNA
<213> ORGANISM: Artificial Sequence
<220> FEATURE:
<223> OTHER INFORMATION: Variant of ATA117

<400> SEQUENCE: 65

```
atggctttct cagctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

tatacttctg acgctaccta cacctgtttc cacgtttgga acggtaacgc tttccgtctg    240

gacgaccaca tcgaacgtct gttctctaac gcggaatcta tccgtatcat cccgccgctg    300

accctggacg aagttaaaga gatcgctctg gaactggttg ctaaaaccga actgcgtgaa    360

gcaatcgttt ctgtttctat cacccgtggt tactcttcta ccccattcga gcgtgacatc    420

accaaacatc gtccgcaggt ttacatgttc gctattccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg actgcgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840
```

```
tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990


<210> SEQ ID NO 66
<211> LENGTH: 330
<212> TYPE: PRT
<213> ORGANISM: Artificial Sequence
<220> FEATURE:
<223> OTHER INFORMATION: Variant of ATA117

<400> SEQUENCE: 66

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Cys Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Leu Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Phe Ala Ile Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 67
<211> LENGTH: 990
<212> TYPE: DNA
<213> ORGANISM: Artificial Sequence
<220> FEATURE:
<223> OTHER INFORMATION: Variant of ATA117

<400> SEQUENCE: 67

```
atggctttct cagctgacac cccggaaatc gtttacaccc acgacaccgg tctggactat     60

atcacctact ctgactacga actggacccg gctaacccgc tggctggtgg tgctgcttgg    120

atcgaaggtg ctttcgttcc ggcgtctgaa gctcgtatct ctatcttcga ccagggttac    180

tatacttctg acgctaccta caccaccttc cacgtttgga acggtaacgc tttccgtctg    240

ggggaccaca tcgaacgtct gttctctaac gcggaatcta ttcgtttgat cccgccgctg    300

accaaagacg aagttaaaga gatcgctctg gaactggttg ctaaaaccga actgcgtgaa    360

gcaatcgttt ctgtttctat cacccgtggt tactcttcta ccccattcga gcgtgacatc    420

accaaacatc gtccgcaggt ttacatgtat gctgttccgt accagtggat cgtaccgttt    480

gaccgcgtcc gtgacggtgt tcacgctatg gttgctcagt ctgttcgtcg tactccgcgt    540

agctctatcg acccgcaggt taaaaacttc cagtggggtg acctgatccg tgcaattcag    600

gaaacccacg accgtggttt cgagctgccg attctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gtttttgaaa tcgctgaatc tctgggtcac    780

gaagctatcc tggctgacat caccctggct gaactgtatg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 68
<211> LENGTH: 330
<212> TYPE: PRT
<213> ORGANISM: Artificial Sequence
<220> FEATURE:
<223> OTHER INFORMATION: Variant of ATA117

<400> SEQUENCE: 68

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Ala
        35                  40                  45

Ser Glu Ala Arg Ile Ser Ile Phe Asp Gln Gly Tyr Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Lys Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125
```

```
Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Val Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Ile Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Phe Glu Ile Ala Glu
                245                 250                 255

Ser Leu Gly His Glu Ala Ile Leu Ala Asp Ile Thr Leu Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 69
<211> LENGTH: 990
<212> TYPE: DNA
<213> ORGANISM: Artificial Sequence
<220> FEATURE:
<223> OTHER INFORMATION: Variant of ATA117

<400> SEQUENCE: 69

```
atggctttct cagctgacac cccggaaatc gtttacaccc acgacaccgg tctggactat      60

atcacctact ctgactacga actggacccg gctaacccgc tggctggtgg tgctgcttgg     120

atcgaaggtg ctttcgttcc ggcgtctgaa gctcgtatct ctatcttcga ccagggttac     180

tatacttctg acgctaccta caccaccttc cacgtttgga acggtaacgc tttccgtctg     240

ggggaccaca tcgaacgtct gttctctaac gcggaatcta ttcgtattat cccgccgctg     300

acccaggacg aagttaaaga gatcgctctg gaactggttg ctaaaaccga actgcgtgaa     360

gcaatcgttt ctgtttctat cacccgtggt tactcttcta ccccattcga gcgtgacatc     420

accaaacatc gtccgcaggt ttacatgtat gctgttccgt accagtggat cgtaccgttt     480

gaccgcatcc gtgacggtgt tcacctgatg gttgctcagt ctgttcgtcg tactccgcgt     540

agctctatcg acccgcaggt taaaaacttc cagtggggtg acctgatccg tgcaattcag     600

gaaacccacg accgtggttt cgagctgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgctgg acgctgacga agttctgggt     840

tgctcaaccg gtggtggtgt ttggccgttc gtttctgttg acggtaactc tatctctgac     900
```

ggtgttccgg gtccggttac ccagtctatc atccgtcgtt actgggaact gaacgttgaa 960
ccttcttctc tgctgacccc ggtacagtac 990

<210> SEQ ID NO 70
<211> LENGTH: 330
<212> TYPE: PRT
<213> ORGANISM: Artificial Sequence
<220> FEATURE:
<223> OTHER INFORMATION: Variant of ATA117

<400> SEQUENCE: 70

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Ala
        35                  40                  45

Ser Glu Ala Arg Ile Ser Ile Phe Asp Gln Gly Tyr Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 71

<211> LENGTH: 990
<212> TYPE: DNA
<213> ORGANISM: Artificial Sequence
<220> FEATURE:
<223> OTHER INFORMATION: Variant of ATA117

<400> SEQUENCE: 71

```
atggctttct cagctgacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

tatacttctg acgctaccta caccaccttc cacgtttgga acggtaacgc tttccgtctg    240

gacgaccaca tcgaacgtct gttctctaac gcggaatcta tccgtatcat cccgccgctg    300

acccaggacg aagttaaaga gatcgctctg gaactggttg ctaaaaccga actgcgtgaa    360

gcaatcgttt ctgtttctat cacccgtggt tactcttcta ccccattcga gcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg actgcgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

<210> SEQ ID NO 72
<211> LENGTH: 330
<212> TYPE: PRT
<213> ORGANISM: Artificial Sequence
<220> FEATURE:
<223> OTHER INFORMATION: Variant of ATA117

<400> SEQUENCE: 72

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Thr Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140
```

```
Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 73
<211> LENGTH: 990
<212> TYPE: DNA
<213> ORGANISM: Artificial Sequence
<220> FEATURE:
<223> OTHER INFORMATION: Variant of ATA117

<400> SEQUENCE: 73

```
atggctttct cagctgacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

tatacttctg acgctaccta caccaccttc cacgtttgga acggtaacgc tttccgtctg    240

ggggaccaca tcgaacgtct gttctctaac gcggaatctt tgcgtttgat cccgccgctg    300

acccaggacg aagttaaaga gatcgctctg gaactggttg ctaaaaccga actgcgtgaa    360

gcaatcgttt ctgtttctat cacccgtggt tactcttcta ccccattcga gcgtgacatc    420

accaaacatc gtccgcaggt ttacatgtat gctgttccgt accagtggat cgtaccgttt    480

gaccgcatcc gtgacggtgt tcacgctatg gttgctcagt ctgttcgtcg ttccccgcgt    540

agctctatcg acccgcaggt taaaaacttc cagtggggtg acctgatccg tgcaattcag    600

gaaacccacg accgtggttt cgagctgccg ctgctgctgg actgcgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgctgg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990
```

<210> SEQ ID NO 74
<211> LENGTH: 330
<212> TYPE: PRT
<213> ORGANISM: Artificial Sequence
<220> FEATURE:
<223> OTHER INFORMATION: Variant of ATA117

<400> SEQUENCE: 74

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Leu Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Ser Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 75
<211> LENGTH: 990
<212> TYPE: DNA
<213> ORGANISM: Artificial Sequence
<220> FEATURE:
<223> OTHER INFORMATION: Variant of ATA117

<400> SEQUENCE: 75

```
atggctttct cagctgacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaac gcggaatcta ttcgtttgat cccgccgctg    300

acccaggacg aagttaaaga gatcgctctg gaactggttg ctaaaaccga actgcgtgaa    360

gcaatcgttt ctgtttctat cacccgtggt tactcttcta ccccattcga gcgtgacatc    420

accaaacatc gtccgcaggt ttacatgtat gctctgccgt accagtggat cgtaccgttt    480

gaccgcatcc gtgacggtgt tcacgctatg gttgctcagt ctgttcgtcg ttccccgcgt    540

agctctatcg acccgcaggt taaaaacttc cagtggggtg acctgatccg tgcaattcag    600

gaaacccacg accgtggttt cgagctgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gtttttgaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990
```

<210> SEQ ID NO 76
<211> LENGTH: 330
<212> TYPE: PRT
<213> ORGANISM: Artificial Sequence
<220> FEATURE:
<223> OTHER INFORMATION: Variant of ATA117

<400> SEQUENCE: 76

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Leu Pro Tyr Gln Trp Ile Val Pro Phe
145                 150                 155                 160
```

-continued

```
Asp Arg Ile Arg Asp Gly Val His Ala Met Val Ala Gln Ser Val Arg
                165                 170                 175

Arg Ser Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Phe Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 77
<211> LENGTH: 990
<212> TYPE: DNA
<213> ORGANISM: Artificial Sequence
<220> FEATURE:
<223> OTHER INFORMATION: Variant of ATA117

<400> SEQUENCE: 77

atggctttct cagctgacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaac gcggaatctt tgcgtttgat cccgccgctg    300

acccaggacg aagttaaaga gatcgctctg gaactggttg ctaaaaccga actgcgtgaa    360

gcaatcgttt ctgtttctat cacccgtggt tactcttcta ccccattcga gcgtgacatc    420

accaaacatc gtccgcaggt ttacatgtat gctgttccgt accagtggat cgtaccgttt    480

gaccgcatcc gtgacggtgt tcacctgatg gttgctcagt ctgttcgtcg ttccccgcgt    540

agctctatcg acccgcaggt taaaaacttc cagtggggtg acctgatccg tgcaattcag    600

gaaacccacg accgtggttt cgagctgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgctgg acgctgacga agttctgggt    840

tgctcaaccg gtggtggtgt ttggccgttc gttactgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 78
```

<211> LENGTH: 330
<212> TYPE: PRT
<213> ORGANISM: Artificial Sequence
<220> FEATURE:
<223> OTHER INFORMATION: Variant of ATA117

<400> SEQUENCE: 78

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Leu Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Ser Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Leu Asp Ala Asp Glu Val Leu Gly Cys Ser Thr Gly Gly Gly Val Trp
        275                 280                 285

Pro Phe Val Thr Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 79
<211> LENGTH: 990
<212> TYPE: DNA
<213> ORGANISM: Artificial Sequence
<220> FEATURE:
<223> OTHER INFORMATION: Variant of ATA117

<400> SEQUENCE: 79
atggctttct cagctgacac ccctgaaatc gtttacaccc acgacaccgg tctggactat 60
atcacctact ctgactacga actggacccg gctaacccgc tggctggtgg tgctgcttgg 120
atcgaaggtg ctttcgttcc gccgtctgaa gctcgtatct ctatcttcga ccagggtttt 180
tatacttctg acgctaccta caccaccttc cacgtttgga acggtaacgc tttccgtctg 240
ggggaccaca tcgaacgtct gttctctaat gcggaatcta ttcgtttgat cccgccgctg 300
acccaggacg aagttaaaga gatcgctctg gaactggttg ctaaaaccga actgcgtgaa 360
gcgatcgttt ctgtttctat cacccgtggt tactcttcta ccccattcga gcgtgacatc 420
accaaacatc gtccgcaggt ttacatgtat gctgttccgt accagtggat cgtaccgttt 480
gaccgcatcc gtgacggtgt tcacctgatg gttgctcagt cagttcgtcg tacaccgcgt 540
agctctatcg acccgcaggt taaaaacttc cagtggggtg acctgatccg tgcaattcag 600
gaaacccacg accgtggttt cgagctgccg ctgctgctgg actgcgacaa cctgctggct 660
gaaggtccgg gtttcaacgt tgttgttatc aaagacggtg ttgttcgttc tccgggtcgt 720
gctgctctgc cgggtatcac ccgtaaaacc gttctggaaa tcgctgaatc tctgggtcac 780
gaagctatcc tggctgacat caccccggct gaactgtacg acgctgacga agttctgggt 840
tgctcaaccg gtggtggtgt ttggccgttc gtttctgttg acggtaactc tatctctgac 900
ggtgttccgg gtccggttac ccagtctatc atccgtcgtt actgggaact gaacgttgaa 960
ccttcttctc tgctgacccc ggtacagtac 990

<210> SEQ ID NO 80
<211> LENGTH: 330
<212> TYPE: PRT
<213> ORGANISM: Artificial Sequence
<220> FEATURE:
<223> OTHER INFORMATION: Variant of ATA117

<400> SEQUENCE: 80

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175
```

```
Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 81
<211> LENGTH: 990
<212> TYPE: DNA
<213> ORGANISM: Artificial Sequence
<220> FEATURE:
<223> OTHER INFORMATION: Variant of ATA117

<400> SEQUENCE: 81

```
atggctttct cagctgacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaac gcggaatctt tgcgtttgat cccgccgctg    300

acccaggacg aagttaaaga gatcgctctg gaactggttg ctaaaaccga actgcgtgaa    360

gcaatcgttt ctgtttctat cacccgtggt tactcttcta ccccattcga gcgtgacatc    420

accaaacatc gtccgcaggt ttacatgtat gctgttccgt accagtggat cgtaccgttt    480

gaccgcatcc gtgacggtgt tcacctgatg gttgctcagt ctgttcgtcg ttccccgcgt    540

agctctatcg acccgcaggt taaaaacttc cagtggggtg acctgatccg tgcaattcag    600

gaaacccacg accgtggttt cgagctgccg ctgctgctgg actgcgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 82
<211> LENGTH: 330
<212> TYPE: PRT
<213> ORGANISM: Artificial Sequence
<220> FEATURE:
<223> OTHER INFORMATION: Variant of ATA117

<400> SEQUENCE: 82

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Leu Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Ser Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 83
<211> LENGTH: 990
<212> TYPE: DNA
<213> ORGANISM: Artificial Sequence
<220> FEATURE:
<223> OTHER INFORMATION: Variant of ATA117

<400> SEQUENCE: 83

```
atggctttct cagctgacac ccctgaaatc gtttacaccc acgacaccgg tctggactat      60
```

```
atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatcgtta ctgtttctat cacccgtggt tactcttcta ccccattcga gcgtgacatc    420

accaaacatc gtccgcaggt ttacatgtat gctgttccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagctgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990
```

```
<210> SEQ ID NO 84
<211> LENGTH: 330
<212> TYPE: PRT
<213> ORGANISM: Artificial Sequence
<220> FEATURE:
<223> OTHER INFORMATION: Variant of ATA117

<400> SEQUENCE: 84

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190
```

```
Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 85
<211> LENGTH: 990
<212> TYPE: DNA
<213> ORGANISM: Artificial Sequence
<220> FEATURE:
<223> OTHER INFORMATION: Variant of ATA117

<400> SEQUENCE: 85

```
atggctttct cagctgacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatcgttc atgtttctat cacccgtggt tactcttcta ccccattcga gcgtgacatc     420

accaaacatc gtccgcaggt ttacatgtat gctgttccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagctgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990
```

<210> SEQ ID NO 86
<211> LENGTH: 330
<212> TYPE: PRT
<213> ORGANISM: Artificial Sequence
<220> FEATURE:
<223> OTHER INFORMATION: Variant of ATA117

<400> SEQUENCE: 86

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val His Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 87
<211> LENGTH: 990
<212> TYPE: DNA
<213> ORGANISM: Artificial Sequence
<220> FEATURE:
<223> OTHER INFORMATION: Variant of ATA117

<400> SEQUENCE: 87

```
atggctttct cagctgacac ccctgaaatc gtttacaccc acgacaccgg tctggactat      60

atcacctact ctgactacga actggacccg gctaacccgc tggctggtgg tgctgcttgg     120
```

```
atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatcgtta atgtttctat cacccgtggt tactcttcta ccccattcga gcgtgacatc    420

accaaacatc gtccgcaggt ttacatgtat gctgttccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagctgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 88
<211> LENGTH: 330
<212> TYPE: PRT
<213> ORGANISM: Artificial Sequence
<220> FEATURE:
<223> OTHER INFORMATION: Variant of ATA117

<400> SEQUENCE: 88

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Asn Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205
```

```
Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 89
<211> LENGTH: 990
<212> TYPE: DNA
<213> ORGANISM: Artificial Sequence
<220> FEATURE:
<223> OTHER INFORMATION: Variant of ATA117

<400> SEQUENCE: 89

atggctttct cagctgacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatcgttt ctgtttctat cacccgtggt tactcttcta ccccattcga gcgtgacatc     420

accaaacatc gtccgcaggt ttacatgcat gctgttccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagctgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                       990


<210> SEQ ID NO 90
<211> LENGTH: 330
<212> TYPE: PRT
<213> ORGANISM: Artificial Sequence
<220> FEATURE:
<223> OTHER INFORMATION: Variant of ATA117

<400> SEQUENCE: 90

Met Ala Phe Ser Ala Asp Thr Pro Glu Ile Val Tyr Thr His Asp Thr
```

```
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met His Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 91
<211> LENGTH: 990
<212> TYPE: DNA
<213> ORGANISM: Artificial Sequence
<220> FEATURE:
<223> OTHER INFORMATION: Variant of ATA117

<400> SEQUENCE: 91

```
atggctttct cagctgacac ccctgaaatc gtttacaccc acgacaccgg tctggactat     60

ataacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240
```

```
ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggttc atgtttctat cacccgtggt tactcttcta ccccattcga gcgtgacatc    420

accaaacatc gtccgcaggt ttacatgcac gctagcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagctgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 92
<211> LENGTH: 330
<212> TYPE: PRT
<213> ORGANISM: Artificial Sequence
<220> FEATURE:
<223> OTHER INFORMATION: Variant of ATA117

<400> SEQUENCE: 92

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val His Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met His Ala Ser Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220
```

```
Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 93
<211> LENGTH: 990
<212> TYPE: DNA
<213> ORGANISM: Artificial Sequence
<220> FEATURE:
<223> OTHER INFORMATION: Variant of ATA117

<400> SEQUENCE: 93

```
atggctttct cagctgacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgattgtta ccgtttctat cacccgtggt tactcttcta ccccattcga gcgtgacatc    420

accaaacatc gtccgcaggt ttacatgagt gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagctgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 94
<211> LENGTH: 330
<212> TYPE: PRT
<213> ORGANISM: Artificial Sequence
<220> FEATURE:
<223> OTHER INFORMATION: Variant of ATA117

<400> SEQUENCE: 94

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
```

-continued

```
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 95
<211> LENGTH: 990
<212> TYPE: DNA
<213> ORGANISM: Artificial Sequence
<220> FEATURE:
<223> OTHER INFORMATION: Variant of ATA117

<400> SEQUENCE: 95

```
atggctttct cagctgacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300
```

```
acccaggacg aagttaaaga gatcgctctg gaactggttg ctaaaaccga actgcgtgaa    360

gcgatggtta acgtttctat cacccgtggt tactcttcta ccccattcga gcgtgacatc    420

accaaacatc gtccgcaggt ttacatgtat gctgttccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 96
<211> LENGTH: 330
<212> TYPE: PRT
<213> ORGANISM: Artificial Sequence
<220> FEATURE:
<223> OTHER INFORMATION: Variant of ATA117

<400> SEQUENCE: 96

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Asn Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240
```

```
Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

```
<210> SEQ ID NO 97
<211> LENGTH: 990
<212> TYPE: DNA
<213> ORGANISM: Artificial Sequence
<220> FEATURE:
<223> OTHER INFORMATION: Variant of ATA117

<400> SEQUENCE: 97

atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatcgttc atgtttctat cacccgtggt tactcttcta ccccattcga gcgtgacatc     420

accaaacatc gtccgcaggt ttacatgtat gctgttccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagctgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990

<210> SEQ ID NO 98
<211> LENGTH: 330
<212> TYPE: PRT
<213> ORGANISM: Artificial Sequence
<220> FEATURE:
<223> OTHER INFORMATION: Variant of ATA117

<400> SEQUENCE: 98

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
```

```
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val His Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 99
<211> LENGTH: 990
<212> TYPE: DNA
<213> ORGANISM: Artificial Sequence
<220> FEATURE:
<223> OTHER INFORMATION: Variant of ATA117

<400> SEQUENCE: 99

atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta acgtttctat cacccgtggt tactcttcta ccccattcga gcgtgacatc     420
```

```
accaaacatc gtccgcaggt ttacatgtat gctgttccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 100
<211> LENGTH: 330
<212> TYPE: PRT
<213> ORGANISM: Artificial Sequence
<220> FEATURE:
<223> OTHER INFORMATION: Variant of ATA117

<400> SEQUENCE: 100

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Asn Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255
```

```
Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 101
<211> LENGTH: 990
<212> TYPE: DNA
<213> ORGANISM: Artificial Sequence
<220> FEATURE:
<223> OTHER INFORMATION: Variant of ATA117

<400> SEQUENCE: 101

atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta acgtttctat cacccgtggt tactcttcta ccccattcga gcgtgacatc     420

accaaacatc gtccgcaggt ttacatgtat gctgttccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacactac                                      990


<210> SEQ ID NO 102
<211> LENGTH: 330
<212> TYPE: PRT
<213> ORGANISM: Artificial Sequence
<220> FEATURE:
<223> OTHER INFORMATION: Variant of ATA117

<400> SEQUENCE: 102

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
```

```
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Asn Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val His Tyr
                325                 330
```

<210> SEQ ID NO 103
<211> LENGTH: 990
<212> TYPE: DNA
<213> ORGANISM: Artificial Sequence
<220> FEATURE:
<223> OTHER INFORMATION: Variant of ATA117

<400> SEQUENCE: 103

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480
```

```
gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 104
<211> LENGTH: 330
<212> TYPE: PRT
<213> ORGANISM: Artificial Sequence
<220> FEATURE:
<223> OTHER INFORMATION: Variant of ATA117

<400> SEQUENCE: 104

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270
```

```
Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 105
<211> LENGTH: 990
<212> TYPE: DNA
<213> ORGANISM: Artificial Sequence
<220> FEATURE:
<223> OTHER INFORMATION: Variant of ATA117

<400> SEQUENCE: 105

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgttacgat cacccgtggt tactcttcta ccccattcga gaaagacatc    420

accaaacatc gtccgcaagt ttacatgagc gctggcccgt acatgtggat cgtaccgttt    480

gaccgcatcc gtgacggtgt tcacctgatg gttgctcagt ctgttcgtcg tacaccgcgt    540

agctctatcg acccgcaggt taaaaacttc cagtggggtg acctgatccg tgcaattcaa    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 106
<211> LENGTH: 330
<212> TYPE: PRT
<213> ORGANISM: Artificial Sequence
<220> FEATURE:
<223> OTHER INFORMATION: Variant of ATA117

<400> SEQUENCE: 106

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
```

```
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Thr Ile Thr
        115                 120                 125

Arg Gly Tyr Ser Ser Thr Pro Phe Glu Lys Asp Ile Thr Lys His Arg
    130                 135                 140

Pro Gln Val Tyr Met Ser Ala Gly Pro Tyr Met Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 107
<211> LENGTH: 990
<212> TYPE: DNA
<213> ORGANISM: Artificial Sequence
<220> FEATURE:
<223> OTHER INFORMATION: Variant of ATA117

<400> SEQUENCE: 107

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttcgat cacccgtggt tactcttcta ccccattcga gcctgacatc    420

accaaacatc gtccgcgcgt ttacatgagc gcttccccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcaa    600
```

```
gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 108
<211> LENGTH: 330
<212> TYPE: PRT
<213> ORGANISM: Artificial Sequence
<220> FEATURE:
<223> OTHER INFORMATION: Variant of ATA117

<400> SEQUENCE: 108

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Pro Asp Ile Thr Lys His Arg
    130                 135                 140

Pro Arg Val Tyr Met Ser Ala Ser Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285
```

```
Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 109
<211> LENGTH: 990
<212> TYPE: DNA
<213> ORGANISM: Artificial Sequence
<220> FEATURE:
<223> OTHER INFORMATION: Variant of ATA117

<400> SEQUENCE: 109

atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgttacgat cacccgtggt tactcttcta ccccattcga gcgtgacatc     420

accaaacatc gtccgcaggt ttacatgagc gcttgcccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990


<210> SEQ ID NO 110
<211> LENGTH: 330
<212> TYPE: PRT
<213> ORGANISM: Artificial Sequence
<220> FEATURE:
<223> OTHER INFORMATION: Variant of ATA117

<400> SEQUENCE: 110

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
```

```
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Thr Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 111
<211> LENGTH: 990
<212> TYPE: DNA
<213> ORGANISM: Artificial Sequence
<220> FEATURE:
<223> OTHER INFORMATION: Variant of ATA117

<400> SEQUENCE: 111

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgccatc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660
```

```
gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 112
<211> LENGTH: 330
<212> TYPE: PRT
<213> ORGANISM: Artificial Sequence
<220> FEATURE:
<223> OTHER INFORMATION: Variant of ATA117

<400> SEQUENCE: 112

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg His Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300
```

```
Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 113
<211> LENGTH: 990
<212> TYPE: DNA
<213> ORGANISM: Artificial Sequence
<220> FEATURE:
<223> OTHER INFORMATION: Variant of ATA117

<400> SEQUENCE: 113

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt tgctatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990
```

<210> SEQ ID NO 114
<211> LENGTH: 330
<212> TYPE: PRT
<213> ORGANISM: Artificial Sequence
<220> FEATURE:
<223> OTHER INFORMATION: Variant of ATA117

<400> SEQUENCE: 114

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
```

```
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Ala Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 115
<211> LENGTH: 990
<212> TYPE: DNA
<213> ORGANISM: Artificial Sequence
<220> FEATURE:
<223> OTHER INFORMATION: Variant of ATA117

<400> SEQUENCE: 115

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagcagat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780
```

```
gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 116
<211> LENGTH: 330
<212> TYPE: PRT
<213> ORGANISM: Artificial Sequence
<220> FEATURE:
<223> OTHER INFORMATION: Variant of ATA117

<400> SEQUENCE: 116

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Gln Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320
```

```
Pro Ser Ser Leu Leu Thr Pro Val Gln Tyr
                325                 330


<210> SEQ ID NO 117
<211> LENGTH: 990
<212> TYPE: DNA
<213> ORGANISM: Artificial Sequence
<220> FEATURE:
<223> OTHER INFORMATION: Variant of ATA117

<400> SEQUENCE: 117

atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgtttctat cacccgtggt tactcttcta ccccattcga gcgtgacatc     420

accaaacatc gtccgcaggt ttacatgagc gcttgcccgt accagtggat cgtaccgttt     480

gaccgcatcg tggacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990


<210> SEQ ID NO 118
<211> LENGTH: 330
<212> TYPE: PRT
<213> ORGANISM: Artificial Sequence
<220> FEATURE:
<223> OTHER INFORMATION: Variant of ATA117

<400> SEQUENCE: 118

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
```

```
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Val Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 119
<211> LENGTH: 990
<212> TYPE: DNA
<213> ORGANISM: Artificial Sequence
<220> FEATURE:
<223> OTHER INFORMATION: Variant of ATA117

<400> SEQUENCE: 119

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttttatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840
```

```
tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 120
<211> LENGTH: 330
<212> TYPE: PRT
<213> ORGANISM: Artificial Sequence
<220> FEATURE:
<223> OTHER INFORMATION: Variant of ATA117

<400> SEQUENCE: 120

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Phe Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 121
<211> LENGTH: 990
<212> TYPE: DNA
<213> ORGANISM: Artificial Sequence
<220> FEATURE:
<223> OTHER INFORMATION: Variant of ATA117

<400> SEQUENCE: 121

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgttat    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 122
<211> LENGTH: 330
<212> TYPE: PRT
<213> ORGANISM: Artificial Sequence
<220> FEATURE:
<223> OTHER INFORMATION: Variant of ATA117

<400> SEQUENCE: 122

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Tyr Ala Met Val Thr Val Ser Ile Thr
        115                 120                 125

Arg Gly Tyr Ser Ser Thr Pro Phe Glu Arg Asp Ile Thr Lys His Arg
```

```
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 123
<211> LENGTH: 990
<212> TYPE: DNA
<213> ORGANISM: Artificial Sequence
<220> FEATURE:
<223> OTHER INFORMATION: Variant of ATA117

<400> SEQUENCE: 123

atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt acgtgtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960
```

```
ccttcttctc tgctgacccc ggtacagtac                                    990


<210> SEQ ID NO 124
<211> LENGTH: 330
<212> TYPE: PRT
<213> ORGANISM: Artificial Sequence
<220> FEATURE:
<223> OTHER INFORMATION: Variant of ATA117

<400> SEQUENCE: 124

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Val Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 125
<211> LENGTH: 990
```

<212> TYPE: DNA
<213> ORGANISM: Artificial Sequence
<220> FEATURE:
<223> OTHER INFORMATION: Variant of ATA117

<400> SEQUENCE: 125
atggcgttct cagcggacac ccctgaaatc gtttacaccc acgacaccgg tctggactat 60
atcacctact ctgactacga actggacccg gctaacccgc tggctggtgg tgctgcttgg 120
atcgaaggtg ctttcgttcc gccgtctgaa gctcgtatct ctatcttcga ccagggtttt 180
tatacttctg acgctaccta caccaccttc cacgtttgga acggtaacgc tttccgtctg 240
ggggaccaca tcgaacgtct gttctctaat gcggaatcta ttcgtttgat cccgccgctg 300
acccaggacg aagttaaaga gatcgctctg gaactggttg ctaaaaccga actgcgtgaa 360
gcgatggtta ccgtttctat cacccgtggt tactcttcta ccccattcga gcgtgacatc 420
accaaacatc gtccgcaggt ttacatgagc gcttgcccgt accagtggat cgtaccgttt 480
gaccgcatcc ctgacggtgt tcacctgatg gttgctcagt cagttcgtcg tacaccgcgt 540
agctctatcg acccgcaggt taaaaacttc cagtggggtg acctgatccg tgcaattcag 600
gaaacccacg accgtggttt cgagttgccg ctgctgctgg actgcgacaa cctgctggct 660
gaaggtccgg gtttcaacgt tgttgttatc aaagacggtg ttgttcgttc tccgggtcgt 720
gctgctctgc cgggtatcac ccgtaaaacc gttctggaaa tcgctgaatc tctgggtcac 780
gaagctatcc tggctgacat caccccggct gaactgtacg acgctgacga agttctgggt 840
tgctcaaccg gtggtggtgt ttggccgttc gtttctgttg acggtaactc tatctctgac 900
ggtgttccgg gtccggttac ccagtctatc atccgtcgtt actgggaact gaacgttgaa 960
ccttcttctc tgctgacccc ggtacagtac 990

<210> SEQ ID NO 126
<211> LENGTH: 330
<212> TYPE: PRT
<213> ORGANISM: Artificial Sequence
<220> FEATURE:
<223> OTHER INFORMATION: Variant of ATA117

<400> SEQUENCE: 126

Met Ala Phe Ser Ala Asp Thr Pro Glu Ile Val Tyr Thr His Asp Thr
1 5 10 15

Gly Leu Asp Tyr Ile Thr Tyr Ser Asp Tyr Glu Leu Asp Pro Ala Asn
20 25 30

Pro Leu Ala Gly Gly Ala Ala Trp Ile Glu Gly Ala Phe Val Pro Pro
35 40 45

Ser Glu Ala Arg Ile Ser Ile Phe Asp Gln Gly Phe Tyr Thr Ser Asp
50 55 60

Ala Thr Tyr Thr Thr Phe His Val Trp Asn Gly Asn Ala Phe Arg Leu
65 70 75 80

Gly Asp His Ile Glu Arg Leu Phe Ser Asn Ala Glu Ser Ile Arg Leu
85 90 95

Ile Pro Pro Leu Thr Gln Asp Glu Val Lys Glu Ile Ala Leu Glu Leu
100 105 110

Val Ala Lys Thr Glu Leu Arg Glu Ala Met Val Thr Val Ser Ile Thr
115 120 125

Arg Gly Tyr Ser Ser Thr Pro Phe Glu Arg Asp Ile Thr Lys His Arg
130 135 140

Pro Gln Val Tyr Met Ser Ala Cys Pro Tyr Gln Trp Ile Val Pro Phe

```
145                 150                 155                 160

Asp Arg Ile Pro Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 127
<211> LENGTH: 990
<212> TYPE: DNA
<213> ORGANISM: Artificial Sequence
<220> FEATURE:
<223> OTHER INFORMATION: Variant of ATA117

<400> SEQUENCE: 127

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt acacttggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990
```

<210> SEQ ID NO 128
<211> LENGTH: 330
<212> TYPE: PRT
<213> ORGANISM: Artificial Sequence
<220> FEATURE:
<223> OTHER INFORMATION: Variant of ATA117

<400> SEQUENCE: 128

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Thr Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 129
<211> LENGTH: 990
<212> TYPE: DNA
<213> ORGANISM: Artificial Sequence
<220> FEATURE:

<223> OTHER INFORMATION: Variant of ATA117

<400> SEQUENCE: 129

```
atggcgttct cagcggacac ccctgaaatc gtttacaccc acgacaccgg tctggactat     60
atcacctact ctgactacga actggacccg gctaacccgc tggctggtgg tgctgcttgg    120
atcgaaggtg ctttcgttcc gccgtctctg gctcgtatct ctatcttcga ccagggtttt    180
tatacttctg acgctaccta caccaccttc cacgtttgga acggtaacgc tttccgtctg    240
ggggaccaca tcgaacgtct gttctctaat gcggaatcta ttcgtttgat cccgccgctg    300
acccaggacg aagttaaaga gatcgctctg gaactggttg ctaaaaccga actgcgtgaa    360
gcgatggtta ccgtttctat cacccgtggt tactcttcta ccccattcga gcgtgacatc    420
accaaacatc gtccgcaggt ttacatgagc gcttgcccgt accagtggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagttgccg ctgctgctgg actgcgacaa cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat caccccggct gaactgtacg acgctgacga agttctgggt    840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                     990
```

<210> SEQ ID NO 130
<211> LENGTH: 330
<212> TYPE: PRT
<213> ORGANISM: Artificial Sequence
<220> FEATURE:
<223> OTHER INFORMATION: Variant of ATA117

<400> SEQUENCE: 130

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Leu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
```

```
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 131
<211> LENGTH: 990
<212> TYPE: DNA
<213> ORGANISM: Artificial Sequence
<220> FEATURE:
<223> OTHER INFORMATION: Variant of ATA117

<400> SEQUENCE: 131

```
atggcgttct cagcggacac ccctgaaatc gtttacaccc acgacaccgg tattgactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 132
<211> LENGTH: 330

```
<212> TYPE: PRT
<213> ORGANISM: Artificial Sequence
<220> FEATURE:
<223> OTHER INFORMATION: Variant of ATA117

<400> SEQUENCE: 132

Met Ala Phe Ser Ala Asp Thr Pro Glu Ile Val Tyr Thr His Asp Thr
1               5                   10                  15

Gly Ile Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 133
<211> LENGTH: 990
<212> TYPE: DNA
<213> ORGANISM: Artificial Sequence
<220> FEATURE:
<223> OTHER INFORMATION: Variant of ATA117

<400> SEQUENCE: 133
```

```
atggcgttct cagcggacac ccctgaaatc gtttacaccc acgacaccgg tctggactat     60

atcacctact ctcagtacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                    990
```

```
<210> SEQ ID NO 134
<211> LENGTH: 330
<212> TYPE: PRT
<213> ORGANISM: Artificial Sequence
<220> FEATURE:
<223> OTHER INFORMATION: Variant of ATA117

<400> SEQUENCE: 134

Met Ala Phe Ser Ala Asp Thr Pro Glu Ile Val Tyr Thr His Asp Thr
1               5                   10                  15

Gly Leu Asp Tyr Ile Thr Tyr Ser Gln Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
```

```
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 135
<211> LENGTH: 990
<212> TYPE: DNA
<213> ORGANISM: Artificial Sequence
<220> FEATURE:
<223> OTHER INFORMATION: Variant of ATA117

<400> SEQUENCE: 135

```
atggcgttct cagcggacac ccctgaaatc gtttacaccc acgacaccgg tctggactat     60

atcacctact ctgactacga actggacccg gctaacccgc tggctggtgg tgctgcttgg    120

atcggtggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990
```

<210> SEQ ID NO 136
<211> LENGTH: 330
<212> TYPE: PRT
<213> ORGANISM: Artificial Sequence
<220> FEATURE:

<223> OTHER INFORMATION: Variant of ATA117

<400> SEQUENCE: 136

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Gly Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 137
<211> LENGTH: 990
<212> TYPE: DNA
<213> ORGANISM: Artificial Sequence
<220> FEATURE:
<223> OTHER INFORMATION: Variant of ATA117

<400> SEQUENCE: 137

```
atggcgttct cagcggacac ccctgaaatc gtttacaccc acgacaccgg tctggactat     60
```

```
atcacctact ctgactacga actggacccg gctaacccgc tggctggtgg tgctgcttgg    120

atcgaaggtg ctttcgttcc ggattctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990
```

```
<210> SEQ ID NO 138
<211> LENGTH: 330
<212> TYPE: PRT
<213> ORGANISM: Artificial Sequence
<220> FEATURE:
<223> OTHER INFORMATION: Variant of ATA117

<400> SEQUENCE: 138

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Asp
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
```

```
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 139
<211> LENGTH: 990
<212> TYPE: DNA
<213> ORGANISM: Artificial Sequence
<220> FEATURE:
<223> OTHER INFORMATION: Variant of ATA117

<400> SEQUENCE: 139

```
atggcgttct cagcggacac ccctgaaatc gtttacaccc acgacaccgg tctggactat     60

atcacctact ctgactacga actggaccag gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 140
<211> LENGTH: 330
<212> TYPE: PRT
<213> ORGANISM: Artificial Sequence
<220> FEATURE:
<223> OTHER INFORMATION: Variant of ATA117

<400> SEQUENCE: 140

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Gln Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 141
<211> LENGTH: 990
<212> TYPE: DNA
<213> ORGANISM: Artificial Sequence
<220> FEATURE:
<223> OTHER INFORMATION: Variant of ATA117

<400> SEQUENCE: 141

```
atggcgttct cagcggacac ccctgaaatc gtttacaccc acgacaccgg tctggactat      60

atcacctact ctgactacga acctgacccg gctaacccgc tggctggtgg tgctgcttgg     120

atcgaaggtg ctttcgttcc gccgtctgaa gctcgtatct ctatcttcga ccagggtttt     180
```

```
tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990
```

```
<210> SEQ ID NO 142
<211> LENGTH: 330
<212> TYPE: PRT
<213> ORGANISM: Artificial Sequence
<220> FEATURE:
<223> OTHER INFORMATION: Variant of ATA117

<400> SEQUENCE: 142

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Pro Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
```

```
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 143
<211> LENGTH: 990
<212> TYPE: DNA
<213> ORGANISM: Artificial Sequence
<220> FEATURE:
<223> OTHER INFORMATION: Variant of ATA117

<400> SEQUENCE: 143

atggcgttct cagcggacac ccctgaaatc gtttacaccc acgacaccgg tctggactat      60

atcacctact ctgactacga actggacccg gctaacccgc tggctggtgg tgctgcttgg     120

catgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgtttctat cacccgtggt tactcttcta ccccattcga gcgtgacatc     420

accaaacatc gtccgcaggt ttacatgagc gcttgcccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990


<210> SEQ ID NO 144
<211> LENGTH: 330
<212> TYPE: PRT
<213> ORGANISM: Artificial Sequence
<220> FEATURE:
<223> OTHER INFORMATION: Variant of ATA117

<400> SEQUENCE: 144

Met Ala Phe Ser Ala Asp Thr Pro Glu Ile Val Tyr Thr His Asp Thr
1               5                   10                  15
```

```
Gly Leu Asp Tyr Ile Thr Tyr Ser Asp Tyr Glu Leu Asp Pro Ala Asn
            20                  25                  30

Pro Leu Ala Gly Gly Ala Ala Trp His Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 145
<211> LENGTH: 990
<212> TYPE: DNA
<213> ORGANISM: Artificial Sequence
<220> FEATURE:
<223> OTHER INFORMATION: Variant of ATA117

<400> SEQUENCE: 145

```
atggcgttct cagcggacac ccctgaaatc gtttacaccc acgacaccgg tctggactat     60

atcacctact ctgactacga actggacatg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240
```

```
ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 146
<211> LENGTH: 330
<212> TYPE: PRT
<213> ORGANISM: Artificial Sequence
<220> FEATURE:
<223> OTHER INFORMATION: Variant of ATA117

<400> SEQUENCE: 146

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Met Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
```

```
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 147
<211> LENGTH: 990
<212> TYPE: DNA
<213> ORGANISM: Artificial Sequence
<220> FEATURE:
<223> OTHER INFORMATION: Variant of ATA117

<400> SEQUENCE: 147

atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatcc atatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 148
<211> LENGTH: 330
<212> TYPE: PRT
<213> ORGANISM: Artificial Sequence
<220> FEATURE:
<223> OTHER INFORMATION: Variant of ATA117

<400> SEQUENCE: 148

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30
```

```
Pro Leu Ala Gly Gly Ala Ala Trp Ile Glu Gly Ala Phe Val Pro Pro
        35                  40                  45

Ser Glu Ala Arg Ile His Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 149
<211> LENGTH: 990
<212> TYPE: DNA
<213> ORGANISM: Artificial Sequence
<220> FEATURE:
<223> OTHER INFORMATION: Variant of ATA117

<400> SEQUENCE: 149

```
atggcgttct cagcggacac ccctgaaatc gtttacaccc acgacaccgg ttgtgactat     60

atcacctact ctgactacga actggacccg gctaacccgc tggctggtgg tgctgcttgg    120

atcgaaggtg ctttcgttcc gccgtctgaa gctcgtatct ctgtcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360
```

```
gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

```
<210> SEQ ID NO 150
<211> LENGTH: 330
<212> TYPE: PRT
<213> ORGANISM: Artificial Sequence
<220> FEATURE:
<223> OTHER INFORMATION: Variant of ATA117

<400> SEQUENCE: 150

Met Ala Phe Ser Ala Asp Thr Pro Glu Ile Val Tyr Thr His Asp Thr
1               5                   10                  15

Gly Cys Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Val Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
```

```
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 151
<211> LENGTH: 990
<212> TYPE: DNA
<213> ORGANISM: Artificial Sequence
<220> FEATURE:
<223> OTHER INFORMATION: Variant of ATA117

<400> SEQUENCE: 151

```
atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gggttctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgtttctat cacccgtggt tactcttcta ccccattcga gcgtgacatc     420

accaaacatc gtccgcaggt ttacatgagc gcttgcccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990
```

<210> SEQ ID NO 152
<211> LENGTH: 330
<212> TYPE: PRT
<213> ORGANISM: Artificial Sequence
<220> FEATURE:
<223> OTHER INFORMATION: Variant of ATA117

<400> SEQUENCE: 152

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Gly
        35                  40                  45
```

```
Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 153
<211> LENGTH: 990
<212> TYPE: DNA
<213> ORGANISM: Artificial Sequence
<220> FEATURE:
<223> OTHER INFORMATION: Variant of ATA117

<400> SEQUENCE: 153

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc ggtttctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420
```

```
accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 154
<211> LENGTH: 330
<212> TYPE: PRT
<213> ORGANISM: Artificial Sequence
<220> FEATURE:
<223> OTHER INFORMATION: Variant of ATA117

<400> SEQUENCE: 154

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Val
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
```

```
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 155
<211> LENGTH: 990
<212> TYPE: DNA
<213> ORGANISM: Artificial Sequence
<220> FEATURE:
<223> OTHER INFORMATION: Variant of ATA117

<400> SEQUENCE: 155

atggcgttct cagcggacac ccctgaaatc gtttacaccc acgacaccgg tctggactat     60

atcacctact ctgactacga actggacccg gctaacccgc tggctggtgg tgctgcttgg    120

tctgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 156
<211> LENGTH: 330
<212> TYPE: PRT
<213> ORGANISM: Artificial Sequence
<220> FEATURE:
<223> OTHER INFORMATION: Variant of ATA117

<400> SEQUENCE: 156

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ser Glu Gly Ala Phe Val Pro Pro
        35                  40                  45

Ser Glu Ala Arg Ile Ser Ile Phe Asp Gln Gly Phe Tyr Thr Ser Asp
    50                  55                  60
```

```
Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

```
<210> SEQ ID NO 157
<211> LENGTH: 990
<212> TYPE: DNA
<213> ORGANISM: Artificial Sequence
<220> FEATURE:
<223> OTHER INFORMATION: Variant of ATA117

<400> SEQUENCE: 157

atggcgttct cagcggacac ccctgaaatc gtttacaccc acgacaccgg tctggactat     60

atcacctact ctgactacac tctggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540
```

```
agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990
```

<210> SEQ ID NO 158
<211> LENGTH: 330
<212> TYPE: PRT
<213> ORGANISM: Artificial Sequence
<220> FEATURE:
<223> OTHER INFORMATION: Variant of ATA117

<400> SEQUENCE: 158

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Thr Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
```

```
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 159
<211> LENGTH: 990
<212> TYPE: DNA
<213> ORGANISM: Artificial Sequence
<220> FEATURE:
<223> OTHER INFORMATION: Variant of ATA117

<400> SEQUENCE: 159

atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatcc ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgtttctat cacccgtggt tactcttcta ccccattcga gcgtgacatc     420

accaaacatc gtccgcaggt ttacatgagc gcttgcccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990


<210> SEQ ID NO 160
<211> LENGTH: 330
<212> TYPE: PRT
<213> ORGANISM: Artificial Sequence
<220> FEATURE:
<223> OTHER INFORMATION: Variant of ATA117

<400> SEQUENCE: 160

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Pro Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80
```

```
Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 161
<211> LENGTH: 990
<212> TYPE: DNA
<213> ORGANISM: Artificial Sequence
<220> FEATURE:
<223> OTHER INFORMATION: Variant of ATA117

<400> SEQUENCE: 161

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gcagtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600
```

```
gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990


<210> SEQ ID NO 162
<211> LENGTH: 330
<212> TYPE: PRT
<213> ORGANISM: Artificial Sequence
<220> FEATURE:
<223> OTHER INFORMATION: Variant of ATA117

<400> SEQUENCE: 162

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Gln
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
```

```
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 163
<211> LENGTH: 990
<212> TYPE: DNA
<213> ORGANISM: Artificial Sequence
<220> FEATURE:
<223> OTHER INFORMATION: Variant of ATA117

<400> SEQUENCE: 163

```
atggcgttct caaaagacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgttacgat cacccgtggt tactcttcta ccccattcga gcgtgacatc     420

accaaacatc gtccgcaggt ttacatgagc gcttgcccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990
```

<210> SEQ ID NO 164
<211> LENGTH: 330
<212> TYPE: PRT
<213> ORGANISM: Artificial Sequence
<220> FEATURE:
<223> OTHER INFORMATION: Variant of ATA117

<400> SEQUENCE: 164

```
Met Ala Phe Ser Lys Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95
```

```
Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Thr Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 165
<211> LENGTH: 990
<212> TYPE: DNA
<213> ORGANISM: Artificial Sequence
<220> FEATURE:
<223> OTHER INFORMATION: Variant of ATA117

<400> SEQUENCE: 165

atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgacggaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccgg cctgcgtgaa     360

gcgatggtta ccgttacgat cacccgtggt tactcttcta ccccattcga gcgtgacatc     420

accaaacatc gtccgcaggt ttacatgagc gctagcccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720
```

```
gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgccccgg gtccggttac ccagtctatc atccgtcgtt actgggaact gaacgttgaa    960

ccttcttctc tgctgacccc ggtacagtac                                     990


<210> SEQ ID NO 166
<211> LENGTH: 330
<212> TYPE: PRT
<213> ORGANISM: Artificial Sequence
<220> FEATURE:
<223> OTHER INFORMATION: Variant of ATA117

<400> SEQUENCE: 166

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Thr Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Gly Leu Arg Glu Ala Met Val Thr Val Thr Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Ser Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Ala Pro Gly
    290                 295                 300

Pro Val Thr Gln Ser Ile Ile Arg Arg Tyr Trp Glu Leu Asn Val Glu
```

```
305                 310                 315                 320

Pro Ser Ser Leu Leu Thr Pro Val Gln Tyr
                325                 330


<210> SEQ ID NO 167
<211> LENGTH: 990
<212> TYPE: DNA
<213> ORGANISM: Artificial Sequence
<220> FEATURE:
<223> OTHER INFORMATION: Variant of ATA117

<400> SEQUENCE: 167

atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatcc ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgttacgat cacccgtggt tactcttcta ccccattcga gcgtgacatc    420

accaaacatc gtccgcaggt ttacatgagc gctagcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg ctcgtggttt cgagttgccg ctgctgctgg actgcgacaa cctgctggct    660

gaaggtccgg gcttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990


<210> SEQ ID NO 168
<211> LENGTH: 330
<212> TYPE: PRT
<213> ORGANISM: Artificial Sequence
<220> FEATURE:
<223> OTHER INFORMATION: Variant of ATA117

<400> SEQUENCE: 168

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Pro Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110
```

-continued

```
Val Ala Lys Thr Glu Leu Arg Glu Ala Met Val Thr Val Thr Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Ser Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Ala Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

TRANSAMINASE BIOCATALYSTS

1. CROSS REFERENCE TO RELATED APPLICATIONS

The present application is a Continuation of U.S. patent application Ser. No. 16/807,977, filed Mar. 3, 2020, which is a Continuation of U.S. patent application Ser. No. 16/195,227, filed Nov. 19, 2018, now U.S. Pat. No. 10,619,176, which is a Continuation of U.S. patent application Ser. No. 15/915,437, filed Mar. 8, 2018, now U.S. Pat. No. 10,160,985, which is a Divisional of U.S. patent application Ser. No. 15/376,837, filed Dec. 13, 2016, now U.S. Pat. No. 9,944,963, which is a Continuation of U.S. patent application Ser. No. 15/140,809, filed Apr. 28, 2016, now U.S. Pat. No. 9,550,982, which is a Divisional of U.S. patent application Ser. No. 14/818,885, filed Aug. 5, 2015, now U.S. Pat. No. 9,353,355, which is a Divisional of U.S. patent application Ser. No. 14/518,143, filed Oct. 20, 2014, now U.S. Pat. No. 9,133,445, which is a Divisional of U.S. patent application Ser. No. 13/604,323, filed Sep. 5, 2012, now U.S. Pat. No. 8,889,380, which is a Continuation of U.S. patent application Ser. No. 12/714,397, filed Feb. 26, 2010, now U.S. Pat. No. 8,293,507, which claims benefit under 35 U.S.C. § 119(e) of application Ser. No. 61/155,902, filed Feb. 26, 2009, each of which is incorporated by reference the contents of which are incorporated herein by reference in its entirety.

2. TECHNICAL FIELD

The present disclosure relates to transaminase biocatalysts and methods of using the biocatalysts.

3. REFERENCE TO SEQUENCE LISTING, TABLE OR COMPUTER PROGRAM

The official copy of the Sequence Listing is submitted concurrently with the specification as an ASCII formatted text file via EFS-Web, with a file name of 376247-035.txt, creation date of Feb. 26, 2010, with a file size of 367 Kbytes. The Sequence Listing filed via EFS-Web is part of the specification and is herein incorporated by reference.

4. BACKGROUND

Following ingestion of a meal, a group of hormones termed incretins, which include glucagon like peptide-1 (GLP-1) and glucose dependent insulinotropic peptide (GIP), are released. Incretins stimulate insulin release and suppress glucagon release in a glucose dependent manner, delay gastric emptying, and increase satiety. Incretins are rapidly degraded by dipeptidyl peptidase-IV (DPP-4).

Sitagliptin is one of a class of anti-hyperglycemic drugs that inhibits DPP-4. Inhibiting DPP-4 activity and thereby delaying the inactivation of incretins appears to improve islet function by increasing alpha-cell and beta-cell responsiveness to glucose, resulting in improved glucose-dependent insulin secretion and reduced inappropriate glucagon secretion. Because of its anti-hyperglycemic effects, sitagliptin has been approved for use in the treatment of Type 2 diabetes in numerous countries.

The current manufacturing process to produce sitagliptin features asymmetric hydrogenation of an unprotected enamine amide (U.S. Pat. No. 7,468,459, which issued on Dec. 23, 2008, the contents of which are incorporated by reference in their entirety; Shultz et al., 2007, Acc. Chem. Res. 40:1320-1326). Using a rhodium Josiphos-ligand catalyst in methanol at 50° C. and 250 psi provides sitagliptin as the free base with about 97% e.e. Crystallization upgrade of the free base yields sitagliptin with >99.5% e.e. and 84% yield, and subsequent reaction with phosphoric acid affords sitagliptin phosphate monohydrate, the active pharmaceutical ingredient ("API") in JANUVIA®, in about 79% overall yield from the enamine amide substrate.

Further improvements in the manufacturing process for sitagliptin are desirable.

5. SUMMARY

The present disclosure provides polypeptides, polynucleotides encoding the polypeptides and methods of using the polypeptides for the biocatalytic conversion of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (the "ketoamide substrate") to (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (the "product) in presence of an amino group donor. The product, having the USAN of sitagliptin, is the active ingredient in JANUVIA®, which has received marketing approval in many countries for the treatment of Type 2 diabetes.

While naturally occurring transaminases measured by the inventors do not measurably act on the ketoamide substrate, the engineered transaminases of the present disclosure are capable of carrying out the facile conversion of the ketoamide substrate to the product. Thus, in one aspect, the present disclosure relates to improved transaminases capable of converting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one ("the ketoamide substrate") to (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine ("the product") in presence of an amino group donor to levels measurable by an analysis technique, such as HPLC-UV absorbance.

In some embodiments, the improved transaminases of the disclosure are capable of carrying out the conversion of the ketoamide substrate to product with an activity that is least equal to or greater than the activity of the polypeptide of SEQ ID NO:4. In the embodiments herein, the improved transaminases are capable of forming the product in enantiomeric excess of at least 90%, 91%, 92%, 93%, 94%, 95%, 96%, 97%, 98%, or 99% or more.

In some embodiments, the improved transaminases are capable of carrying out the conversion of the ketoamide substrate to product with at least 1.5 times, 2 times, 3 times, 4 times, 5 times, 6 times, 7 times, 8 times, 9 times, 10 times, 15 times, 20 times, 30 times, 40 times, 50 times, 75 times, 100 times, 150 times, 200 times, 300 times, 400 times, 500 times, 1000 times, 1500 times, 2000 times or greater than 2000 times the activity of the polypeptide of SEQ ID NO:4 under defined reaction conditions. In some embodiments, the reaction conditions comprise a temperature of 45° C., and a pH of about 8.5.

In some embodiments, the improved transaminase polypeptides are capable of converting the ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to the product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in the presence of an amino group donor with an activity that is improved over the activity of the transaminase of SEQ ID NO: 2 and comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:4, 68, 70, 72, 74, 76, 78, 80, 82, 84, 86, 88, 90, 92, 94, 96, 98, 100 or 102.

In some embodiments, the improved transaminase polypeptide can comprise an amino acid sequence comprising one or more residue differences as compared to the sequence of SEQ ID NO:2 at the following residue positions corresponding to: X4; X5; X8; X18; X25; X26; X27; X28; X30; X41; X42; X48; X49; X50; X54; X55; X60; X61; X62; X65; X69; X81; X94; X96; X102; X117; X120; X122; X124; X126; X136; X137; X138; X146; X148; X150; X152; X155; X156; X160; X163; X164; X169; X174; X178; X195; X199; X204; X208; X209; X211; X215; X217; X223; X225; X230; X252; X269; X273; X282, X284; X292; X297; X302; X306; X321; and X329. Guidance for the choice of various amino acid residues that can be present at the specified residue positions are provided in the detailed description that follows.

In some embodiments, the improved transaminase polypeptide comprises an amino acid sequence that includes at least one of the following features: residue corresponding to X69 is cysteine (C) or a non-polar, polar, or aliphatic residue; residue corresponding to X122 is a constrained, non-polar or aliphatic residue; residue corresponding to X223 is a constrained residue; and residue corresponding to X284 is a non-polar residue.

In some embodiments, the improved transaminase polypeptide comprises an amino acid sequence that includes at least the following features: residue corresponding to X69 is C or a non-polar, polar, or aliphatic residue, and/or residue corresponding to X284 is a non-polar residue; residue corresponding to X122 is a constrained, non-polar or aliphatic residue; and residue corresponding to X223 is a constrained residue.

In some embodiments, the improved transaminase polypeptide comprises an amino acid sequence that includes at least the following features: residue corresponding to X69 is C or a non-polar, polar, or aliphatic residue; residue corresponding to X122 is a constrained, non-polar or aliphatic residue; and residue corresponding to X223 is a constrained residue.

In some embodiments, the improved transaminase polypeptide comprises an amino acid sequence that includes at least the following features: residue corresponding to X122 is a constrained, non-polar or aliphatic residue; residue corresponding to X223 is a constrained residue; and X284 is a non-polar residue.

In some embodiments, the improved transaminase polypeptide comprises an amino acid sequence that includes at least the following features: residue corresponding to X69 is C or a non-polar, polar or aliphatic residue; residue corresponding to X122 is a constrained, non-polar or aliphatic residue; residue corresponding to X223 is a constrained residue; and residue corresponding to X284 is a non-polar residue.

In some embodiments, the improved transaminase polypeptide comprises an amino acid sequence that includes, in addition to the features described herein for one or more of residue positions X69, X122, X223, and X284, further includes at least the following features: X26 is an aromatic or constrained residue, and/or X62 is an aromatic or polar residue; X65 is an aliphatic residue; X136 is an aromatic residue; X199 is an aliphatic or aromatic residue; and X209 is an aliphatic residue.

In some embodiments, the improved transaminase polypeptide comprises an amino acid sequence that includes, in addition to the features described herein for one or more of residue positions X69, X122, X223, and X284, further includes at least the following features: X61 is an aromatic residue; X62 is an aromatic or polar residue; X65 is an aliphatic residue; X94 is an aliphatic residue; X136 is an aromatic residue; X199 is an aliphatic or aromatic residue; X209 is an aliphatic residue; X215 is a C; and X282 is a polar residue.

In some embodiments, the improved transaminase polypeptide comprises an amino acid sequence that includes, in addition to the features described herein for one or more of residue positions X69, X122, X223, and X284, further includes at least the following features: X8 is a constrained residue; X61 is an aromatic residue; X62 is an aromatic or polar residue; X65 is an aliphatic residue; X81 is a non-polar or small residue; X94 is an aliphatic residue; X136 is an aromatic residue; X199 is an aliphatic or aromatic residue; X209 is an aliphatic residue; X215 is a C; X217 is a polar residue; X269 is a constrained residue; X282 is a polar residue; X297 is a polar residue; and X321 is a constrained residue.

In some embodiments, the improved transaminase polypeptide comprises an amino acid sequence that includes, in addition to the features described herein for one or more of residue positions X69, X122, X223, and X284, further includes at least the following features: X8 is a constrained residue; X60 is an aromatic residue; X61 is an aromatic residue; X62 is an aromatic or polar residue; X65 is an aliphatic residue; X81 is a non-polar residue; X94 is an aliphatic residue; X96 is an aliphatic residue; X124 is a polar or constrained residue; X136 is an aromatic residue; X169 is an aliphatic residue; X199 is an aliphatic or aromatic residue; X209 is an aliphatic residue; X215 is a C; X217 is a polar residue; X269 is a constrained residue; X273 is an aromatic residue; X282 is a polar residue; X297 is a polar residue; and X321 is a constrained residue.

In some embodiments, the improved engineered transaminase polypeptide comprises an amino acid sequence corresponding to the sequence of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

In a further aspect, the present disclosure provides polynucleotides encoding the improved engineered transaminase polypeptides. In some embodiments, the polynucleotides can be part of an expression vector having one or more control sequences for the expression of the transaminase polypeptide. In some embodiments, the polynucleotide can comprise a sequence corresponding to the sequence of SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, or 167.

In another aspect, the present disclosure provides host cells comprising the polynucleotides encoding the engineered transaminases or expression vectors capable of expressing the engineered transaminases. In some embodiments, the host cell can be a bacterial host cells, such as *E. coli*. The host cells can be used for the expression and isolation of the engineered transaminase enzymes described herein, or, alternatively, they can be used directly for the conversion of the ketoamide substrate to product.

In some embodiments, the engineered transaminases, in the form of whole cells, crude extracts, isolated polypeptides, or purified polypeptides, can be used individually or as a combination of different engineered transaminases.

In a further aspect, the improved engineered transaminase polypeptides described herein can be used in a process for transamination of certain amino group acceptors (e.g., a ketone acceptor) in presence of an amino group donor. In some embodiments, the transaminases can be used in a process for preparing a compound of structural formula (I):

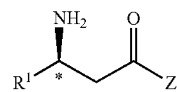

(I)

having the indicated stereochemical configuration at the stereogenic center marked with an *; in an enantiomeric excess of at least 70% over the opposite enantiomer, wherein Z is $OR^2$ or $NR^2R^3$;

$R^1$ is $C_{1-8}$ alkyl, aryl, heteroaryl, aryl-$C_{1-2}$ alkyl, or heteroaryl-$C_{1-2}$ alkyl;

$R^2$ and $R^3$ are each independently hydrogen, $C_{1-8}$ alkyl, aryl, or aryl-$C_{1-2}$ alkyl; or $R^2$ and $R^3$ together with the nitrogen atom to which they are attached form a 4- to 7-membered heterocyclic ring system optionally containing an additional heteroatom selected from O, S, NH, and $NC_{1-4}$ alkyl, the heterocyclic ring being unsubstituted or substituted with one to three substituents independently selected from oxo, hydroxy, halogen, $C_{1-4}$ alkoxy, and $C_{1-4}$ alkyl, wherein alkyl and alkoxy are unsubstituted or substituted with one to five fluorines; and the heterocyclic ring system being optionally fused with a 5- to 6-membered saturated or aromatic carbocyclic ring system or a 5- to 6-membered saturated or aromatic heterocyclic ring system containing one to two heteroatoms selected from O, S, and $NC_{0-4}$ alkyl, the fused ring system being unsubstituted or substituted with one to two substituents selected from hydroxy, amino, fluorine, $C_{1-4}$ alkyl, $C_{1-4}$ alkoxy, and trifluoromethyl, wherein the process comprises the step of contacting a prochiral ketone of structural formula (II):

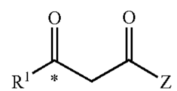

(II)

with an improved engineered transaminase polypeptide disclosed above in the presence of an amino group donor in a suitable organic solvent under suitable reaction conditions for the conversion of the compound of formula (II) to the compound of formula (I).

In some embodiments, the improved engineered transaminase polypeptides described herein can be used in a process for preparing a compound of structural formula (1):

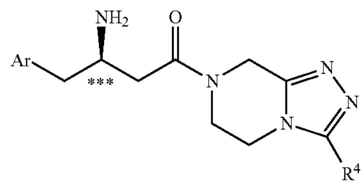

(1)

having the (R)-configuration at the stereogenic center marked with an ***, in an enantiomeric excess of at least 70% over the enantiomer having the opposite (S)-configuration; wherein Ar is phenyl which is unsubstituted or substituted with one to five substituents independently selected from the group consisting of fluorine, trifluoromethyl, and trifluoromethoxy; and $R^4$ is hydrogen or $C_{1-4}$ alkyl unsubstituted or substituted with one to five fluorines wherein, the process comprises the step of contacting a prochiral ketone of structural formula (2):

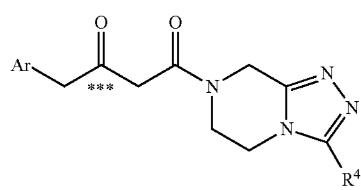

(2)

with an improved engineered transaminase polypeptide disclosed herein in the presence of an amino group donor in a suitable organic solvent under suitable reaction conditions for the conversion of the compound of formula (2) to the compound of formula (1). In some embodiments of the process, the Ar of formula (2) is 2,5-difluorophenyl or 2,4,5-trifluorophenyl, and $R^4$ is trifluoromethyl. In some embodiments of the process, the Ar of formula (2) is 2,4,5-trifluorophenyl.

In some embodiments, the improved engineered transaminase polypeptides can be used in a process for preparing a compound of formula (1a), (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine, in enantiomeric excess:

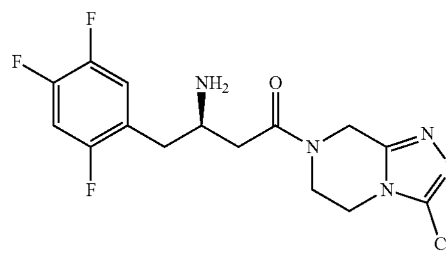

(1a)

In these embodiments, the process comprises the step of contacting a prochiral ketone of structural formula (2a), 4-oxo-4-[3-(trifluoromethyl)-5,6-dihydro[1,2,4]triazolo[4,3-a]pyrazin-7(8H)-yl]-1-(2,4,5-trifluorophenyl)butan-2-one):

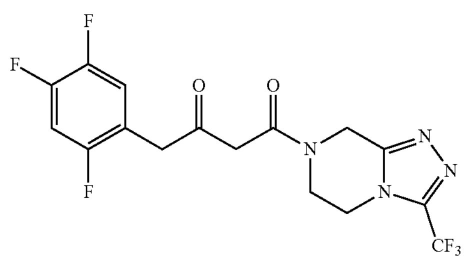

with an improved transaminase polypeptide disclosed herein in the presence of an amino group donor in a suitable organic solvent under suitable reaction conditions for the conversion of the compound of formula (2a) to the compound of formula (1a).

In some embodiments of the above processes, the compound of formula (I), the compound of formula (1) or the compound of formula (1a) is produced in at least 70%, 80%, 90%, 91%, 92%, 93%, 94%, 95%, 96%, 97%, 98%, 99% or more enantiomeric excess. In some embodiments of the processes, the compound of formula (I), the compound of formula (I) or the compound of formula (1a) is produced in at least 99% enantiomeric excess.

In some embodiments of the above processes where the choice of the amino group donor results in a carbonyl by-product that has a vapor pressure higher than water (e.g., a low boiling co-product such as a volatile organic carbonyl compound), the process can be carried out wherein the carbonyl by-product is removed by sparging the reaction solution with a non-reactive gas (e.g., nitrogen) or by applying a vacuum to lower the reaction pressure and removing the carbonyl by-product present in the gas phase.

The improved engineered transaminase polypeptides useful for the above processes can comprise an amino acid sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

In a further aspect, the present disclosure provides processes for preparing (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine using the engineered transaminases disclosed herein. In some embodiments, the process comprises contacting a ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one in presence of an amino group donor with an engineered transaminase polypeptide described herein under reaction conditions suitable for converting the ketoamide substrate to product (2R)-4-oxo-4-[3-(trifluoromethyl)-5,6-dihydro[1,2,4]triaxolo[4,3-a]pyraxin-7(8H)-yl]-1-(2,4,5-trifluorophenyl)butan-2-amine.

In some embodiments, the process is capable of forming the product (2R)-4-oxo-4-[3-(trifluoromethyl)-5,6-dihydro[1,2,4]triaxolo[4,3-a]pyraxin-7(8H)-yl]-1-(2,4,5-trifluorophenyl)butan-2-amine in at least 90% enantiomeric excess.

In some embodiments, the process is capable of forming the product (2R)-4-oxo-4-[3-(trifluoromethyl)-5,6-dihydro[1,2,4]triaxolo[4,3-a]pyraxin-7(8H)-yl]-1-(2,4,5-trifluorophenyl)butan-2-amine in at least 99% enantiomeric excess.

In some embodiments, the process for converting ketoamide substrate 4-oxo-4-[3-(trifluoromethyl)-5,6-dihydro[1,2,4]triaxolo[4,3-a]pyraxin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine comprises contacting the ketoamide substrate at about 50 g/L with about 5 g/L of a transaminase described herein under reaction conditions of pH 8.5 and 45° C. in presence of 1 M isopropylamine, wherein at least 90% of the ketoamide substrate is converted to product in 24 hrs. In some embodiments, the transaminase polypeptide capable of carrying out the foregoing reaction comprises an amino acid sequence corresponding to SEQ ID NO: 80, 86, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

6. DETAILED DESCRIPTION

The present disclosure provides highly stereoselective and efficient biocatalysts capable of mediating transformations involving transamination of certain amino group acceptors, e.g., the synthesis of sitagliptin. The biocatalysts are engineered transaminase polypeptides that can convert the substrate of formula (2a), 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (the "ketoamide substrate"), to the product of formula (1a) (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (the "product) in presence of an amino group donor of formula (3), as follows:

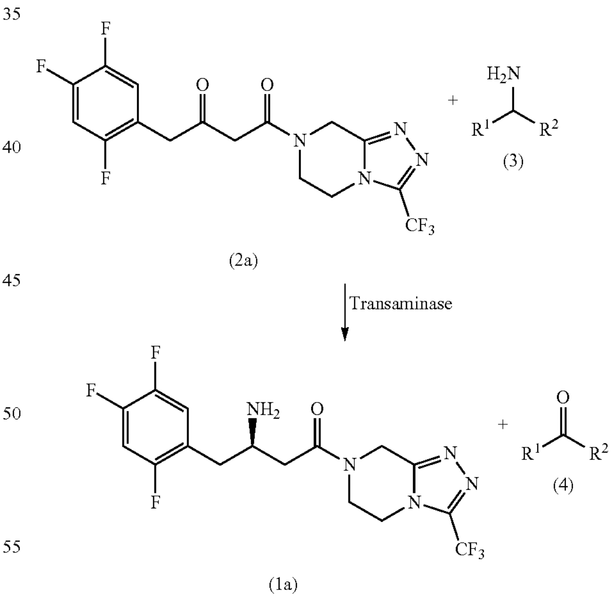

In certain embodiments, the engineered transaminases are derived from the naturally occurring transaminase of *Arthrobacter* sp KNK168, which is an R-selective pyridoxal 5'-phosphate dependent enzyme that can catalyze the reversible transfer of an amino group between an amino group donor and an amino group acceptor, typically a prochiral ketone (see, e.g., Iwasaki et al., 2006, Appl. Microbiol. Biotechnol. 69: 499-505; and U.S. Pat. No. 7,169,592, each of which is hereby incorporated by reference herein). The R-stereoselective transamination activity of the naturally occurring transaminase from *Arthrobacter* sp. KNK168 has been demonstrated on 3,4-dimethoxyphenylacetone, but the naturally occurring enzyme and the transaminase of SEQ ID NO:2 do not display measurable activity for the ketoamide substrate (2a), 4-oxo-4-[3-(trifluoromethyl)-5,6-dihydro[1,2,4]triazolo[4,3-a]pyrazin-7(8H)-yl]-1-(2,4,5-trifluorophenyl)butan-2-one. The transaminase of SEQ ID NO:2 differs from the naturally occurring enzyme from *Arthrobacter* sp. KNK168 in having a substitution of isoleucine (I) at residue position X306 with valine (V). To overcome these shortcomings, the transaminase of SEQ ID NO:2 has been engineered to mediate the efficient conversion of the ketoamide substrate of formula (2a) to the product of formula (1a) in the presence of an amino group donor, such as isopropylamine. The conversion can be carried out under mild conditions with high % conversion and stereoselectivity, making the process applicable to high volume production of sitagliptin.

6.1 Abbreviations and Definitions

For the purposes of the descriptions herein, the abbreviations used for the genetically encoded amino acids are conventional and are as follows:

| Amino Acid | Three-Letter Abbreviation | One-Letter Abbreviation |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When the three-letter abbreviations are used, unless specifically preceded by an "L" or a "D" or clear from the context in which the abbreviation is used, the amino acid may be in either the L- or D-configuration about α-carbon (Cα). For example, whereas "Ala" designates alanine without specifying the configuration about the α carbon, "D-Ala" and "L-Ala" designate D-alanine and L-alanine, respectively. When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When peptide sequences are presented as a string of one-letter or three-letter abbreviations (or mixtures thereof), the sequences are presented in the N→C direction in accordance with common convention.

The technical and scientific terms used in the descriptions herein will have the meanings commonly understood by one of ordinary skill in the art, unless specifically defined otherwise. Accordingly, the following terms are intended to have the following meanings.

"Aminotransferase" and "transaminase" are used interchangeably herein to refer to a polypeptide having an enzymatic capability of transferring an amino group ($NH_2$) and a hydrogen atom from a primary amine (3) to an acceptor carbonyl compound (2), converting the amine donor into its corresponding carbonyl compound (4) and the acceptor into its corresponding primary amine (1):

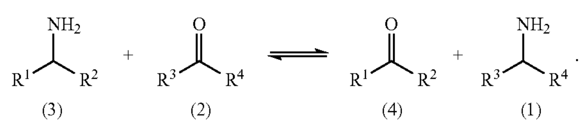

In the embodiments herein, the transaminase polypeptides are capable of enantioselectively converting the compound of formula (2a) to the compound of formula (1a) in the presence of an amino group donor of formula (3).

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Substrate" as used herein refers to an amino group acceptor, such as a ketone, that accepts the amino group from an amino group donor in a reaction mediated by a transaminase. In the context of the present disclosure, substrate for the transaminase includes, among others, the compound of formula (II), the compound of formula (2) and the compound of formula (2a), as further described herein. A "ketoamide substrate" specifically refers to the compound of formula (2a), 4-oxo-4-[3-(trifluoromethyl)-5,6-dihydro[1,2,4]triazolo[4,3-a]pyrazin-7(8H)-yl]-1-(2,4,5-trifluorophenyl)butan-2-one.

"Amino group donor" refers to an amino compound which is capable of donating an amino group to an acceptor carbonyl compound (i.e., an amino group acceptor), thereby becoming a carbonyl by-product. Amino group donors are molecules of general formula (3), (3)

$$\mathrm{R^1{-}CH(NH_2){-}R^2}$$

in which each of $R^1$, $R^2$, when taken independently, is an alkyl, an alkylaryl group, or aryl group which is unsubstituted or substituted with one or more enzymatically non-inhibiting groups. $R^1$ can be the same or different from $R^2$ in structure or chirality. The groups $R^1$ and $R^2$, taken together, may form a ring that is unsubstituted, substituted, or fused to other rings. Typical amino group donors that can be used with the invention include chiral and achiral amino acids, and chiral and achiral amines.

"Chiral amine" refers to amines of general formula $R^1$—$CH(NH_2)$—$R^2$ wherein $R^1$ and $R^2$ are nonidentical and is employed herein in its broadest sense, including a wide variety of aliphatic and alicyclic compounds of different, and mixed, functional types, characterized by the presence of a primary amino group bound to a secondary carbon atom which, in addition to a hydrogen atom, carries either (i) a divalent group forming a chiral cyclic structure, or (ii) two substituents (other than hydrogen) differing from each other in structure or chirality. Divalent groups forming a chiral cyclic structure include, for example, 2-methylbutane-1,4-diyl, pentane-1,4-diyl, hexane-1,4-diyl, hexane-1,5-diyl, 2-methylpentane-1,5-diyl. The two different substituents on the secondary carbon atom ($R^1$ and $R^2$ above) also can vary widely and include alkyl, aralkyl, aryl, halo, hydroxy, lower alkyl, lower alkoxy, lower alkylthio, cycloalkyl, carboxy, carboalkoxy, carbamoyl, mono- and di-(lower alkyl) substituted carbamoyl, trifluoromethyl, phenyl, nitro, amino, mono- and di-(lower alkyl) substituted amino, alkylsulfonyl, arylsulfonyl, alkylcarboxamido, arylcarboxamido, etc., as well as alkyl, aralkyl, or aryl substituted by the foregoing.

"Carbonyl by-product" refers to the carbonyl compound formed from the amino group donor when the amino group on the amino group donor is transferred to the amino group acceptor in a transamination reaction. The carbonyl by-product has the general structure of formula (4):

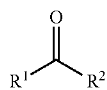

(4)

wherein $R^1$ and $R^2$ are defined above for the amino group donor.

"Pyridoxal-phosphate", "PLP", "pyridoxal-5'-phosphate", "PYP", and "P5P" are used interchangeably herein to refer to the compound that acts as a coenzyme in transaminase reactions. In some embodiments, pyridoxal phosphate is defined by the structure 1-(4'-formyl-3'-hydroxy-2'-methyl-5'-pyridyl)methoxyphosphonic acid, CAS number [54-47-7]. Pyridoxal-5'-phosphate is produced in vivo by phosphorylation and oxidation of pyridoxol (also known as pyridoxine or Vitamin B6). In transamination reactions using transaminase enzymes, the amino group of the amino group donor is transferred to the coenzyme to produce a keto byproduct, while pyridoxal-5'-phosphate is converted to pyridoxamine phosphate. Pyridoxal-5'-phosphate is regenerated by reaction with a different keto compound (the amino group acceptor). The transfer of the amino group from pyridoxamine phosphate to the amino acceptor produces a chiral amine and regenerates the coenzyme. The pyridoxal-5'-phosphate of the current invention can be replaced by other members of the vitamin $B_6$ family, including, among others, pyridoxal (PL), pyridoxamine (PM), and their phosphorylated counterparts; pyridoxine phosphate (PNP), and pyridoxamine phosphate (PMP).

"Coding sequence" refers to that portion of a nucleic acid (e.g., a gene) that encodes an amino acid sequence of a protein.

"Naturally occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity," "percent identity," and "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see e.g., Altschul et al., 1990, J. Mol. Biol. 215: 403-410 and Altschul et al., 1977, Nucleic Acids Res. 3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915).

Numerous other algorithms are available that function similarly to BLAST in providing percent identity for two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelrys, Madison WI), using default parameters provided.

"Reference sequence" refers to a defined sequence to which another (e.g., altered) sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity.

The term "reference sequence" is not intended to be limited to wild-type sequences, and can include engineered or altered sequences. For example, in some embodiments, a "reference sequence" can be a previously engineered or altered amino acid sequence. For instance, a "reference sequence based on SEQ ID NO:2 having a glycine residue at position X284" refers to a reference sequence corresponding to SEQ ID NO:2 with a glycine residue at X284 (the un-altered version of SEQ ID NO:2 has alanine at X284).

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent sequence identity, at least 89 percent sequence identity, at least 95 percent sequence identity, and even at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered transaminase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess.

"Highly stereoselective" refers to a chemical or enzymatic reaction that is capable of converting a substrate (e.g., formula (2a)) to its corresponding product (e.g., formula (1a)) with at least about 85% stereoisomeric excess.

"Improved enzyme property" refers to any enzyme property made better or more desirable for a particular purpose as compared to that property found in a reference enzyme. For the engineered transaminase polypeptides described herein, the comparison is generally made to the wild-type transaminase enzyme, although in some embodiments, the reference transaminase can be another improved engineered transaminase. Enzyme properties for which improvement can be made include, but are not limited to, enzymatic activity (which can be expressed in terms of percent conversion of the substrate in a period of time), thermal stability, solvent stability, pH activity profile, coenzyme requirements, refractoriness to inhibitors (e.g., product inhibition), stereospecificity, and stereoselectivity (including enantioselectivity).

"Increased enzymatic activity" or "increased activity" refers to an improved property of an engineered enzyme, which can be represented by an increase in specific activity (e.g., product produced/time/weight protein) or an increase in percent conversion of the substrate to the product (e.g., percent conversion of starting amount of substrate to product in a specified time period using a specified amount of transaminase) as compared to a reference enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.5 times the enzymatic activity of the corresponding wild-type or engineered enzyme, to as much as 2 times, 5 times, 10 times, 20 times, 25 times, 50 times, 75 times, 100 times, or more enzymatic activity than the naturally occurring enzyme (e.g., a transaminase) or another engineered enzyme from which the enzymes exhibiting increased activity were derived. In specific embodiments, the engineered transaminase enzymes of the present disclosure exhibit improved enzymatic activity in the range of 1.5 to 50 times, 1.5 to 100 times or greater than that of the parent transaminase enzyme (i.e., the wild-type or engineered transaminase from which they were derived). It is understood by the skilled artisan that the activity of any enzyme is diffusion limited such that the catalytic turnover rate cannot exceed the diffusion rate of the substrate, including any required coenzymes. The theoretical maximum of the diffusion limit is generally about $10^8$ to $10^9$ ($M^{-1}$ $s^{-1}$). Hence, any improvements in the enzyme activity of the transaminase will have an upper limit related to the diffusion rate of the substrates acted on by the transaminase enzyme. Transaminase activity can be measured by any one of standard assays used for measuring transaminases, such as change in substrate or product concentration, or change in concentration of the amino group donor. Comparisons of enzyme activities are made using a defined preparation of enzyme, a defined assay under a set condition, and one or more defined substrates, as further described in detail herein. Generally, when enzymes in cell lysates are compared, the numbers of cells and the amount of protein assayed are determined as well as use of identical expression systems and identical host cells to minimize variations in amount of enzyme produced by the host cells and present in the lysates.

"Conversion" refers to the enzymatic transformation of a substrate to the corresponding product. "Percent conversion" refers to the percent of the substrate that is converted to the product within a period of time under specified conditions. Thus, for example, the "enzymatic activity" or "activity" of a transaminase polypeptide can be expressed as "percent conversion" of the substrate to the product.

"Thermostable" or "thermal stable" are used interchangeably to refer to a polypeptide that is resistant to inactivation when exposed to a set of temperature conditions (e.g., 40-80° C.) for a period of time (e.g., 0.5-24 hrs) compared to the untreated enzyme, thus retaining a certain level of residual activity (more than 60% to 80% for example) after exposure to elevated temperatures.

"Solvent stable" refers to a polypeptide that maintains similar activity (more than e.g., 60% to 80%) after exposure to varying concentrations (e.g., 5-99%) of solvent, (e.g., isopropyl alcohol, dimethylsulfoxide, tetrahydrofuran, 2-methyltetrahydrofuran, acetone, toluene, butylacetate, methyl tert-butylether, acetonitrile, etc.) for a period of time (e.g., 0.5-24 hrs) compared to the untreated enzyme.

"pH stable" refers to a polypeptide that maintains similar activity (more than e.g., 60% to 80%) after exposure to low or high pH (e.g., 4.5-6 or 8-12) for a period of time (e.g., 0.5-24 hrs) compared to the untreated enzyme.

"Thermo- and solvent stable" refers to a polypeptide that is both thermostable and solvent stable.

"Derived from" as used herein in the context of engineered enzymes identifies the originating enzyme, and/or the gene encoding such enzyme, upon which the engineering was based. For example, the engineered transaminase enzyme of SEQ ID NO: 4 was obtained by mutating the transaminase of SEQ ID NO:2. Thus, this engineered transaminase enzyme of SEQ ID NO:4 is "derived from" the polypeptide of SEQ ID NO:2

"Amino acid" or "residue" as used in context of the polypeptides disclosed herein refers to the specific monomer at a sequence position (e.g., P8 indicates that the "amino acid" or "residue" at position 8 of SEQ ID NO: 2 is a proline.)

"Hydrophilic amino acid or residue" refers to an amino acid or residue having a side chain exhibiting a hydrophobicity of less than zero according to the normalized consensus hydrophobicity scale of Eisenberg et al., 1984, J. Mol. Biol. 179:125-142. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R).

"Acidic amino acid or residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic amino acid or residue" refers to a hydrophilic amino acid or residue having a side chain exhibiting a pKa value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar amino acid or residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Hydrophobic amino acid or residue" refers to an amino acid or residue having a side chain exhibiting a hydrophobicity of greater than zero according to the normalized consensus hydrophobicity scale of Eisenberg et al., 1984, J. Mol. Biol. 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic amino acid or residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue" (see below).

"Constrained amino acid or residue" refers to an amino acid or residue that has a constrained geometry. Herein, constrained residues include L-Pro (P) and L-His (H). Histidine has a constrained geometry because it has a relatively small imidazole ring. Proline has a constrained geometry because it also has a five membered ring.

"Non-polar amino acid or residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic amino acid or residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Cysteine" or L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Small amino acid or residue" refers to an amino acid or residue having a side chain that is composed of a total of three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Hydroxyl-containing amino acid or residue" refers to an amino acid containing a hydroxyl (—OH) moiety. Genetically-encoded hydroxyl-containing amino acids include L-Ser (S) L-Thr (T) and L-Tyr (Y).

"Amino acid difference" or "residue difference" refers to a change in the residue at a specified position of a polypeptide sequence when compared to a reference sequence. For example, a residue difference at position X8, where the reference sequence has a serine, refers to a change of the residue at position X8 to any residue other than serine. As disclosed herein, an enzyme can include one or more residue differences relative to a reference sequence, where multiple residue differences typically are indicated by a list of the specified positions where changes are made relative to the reference sequence (e.g., "one or more residue differences as compared to SEQ ID NO:2 at the following residue positions: X4; X8; X26; X48; X60; X61; X62; X65; X81; X94; X96; X102; X124; X136; X137; X150; X152; X160; X163; X169; X174; X178; X195; X199; X208; X209; X211; X215; X217; X225; X230; X252; X269; X273; X282; X292; X297; X306; X321; and X329.").

"Conservative" amino acid substitutions or mutations refer to the interchangeability of residues having similar side chains, and thus typically involves substitution of the amino acid in the polypeptide with amino acids within the same or similar defined class of amino acids. However, as used herein, in some embodiments, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. The table below shows exemplary conservative substitutions.

TABLE 1

| Residue | Possible Conservative Mutations |
|---|---|
| A, L, V, I | Other aliphatic (A, L, V, I) |
| | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S, T | Other polar |
| Y, W, F | Other aromatic (Y, W, F) |
| C | None |

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g., proline for glycine) (b) the charge or hydrophobicity, or (c) the bulk of the side chain.

"Deletion" refers to modification of the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, up to 20% of the total number of amino acids, or up to 30% of the total number of amino acids making up the polypeptide while retaining enzymatic activity and/or retaining the improved properties of an engineered transaminase enzyme. Deletions can be directed to the internal portions and/or terminal portions of the polypeptide. In various embodiments, the deletion can comprise a continuous segment or can be discontinuous.

"Insertion" refers to modification of the polypeptide by addition of one or more amino acids to the reference polypeptide. In some embodiments, the improved engineered transaminase enzymes comprise insertions of one or more amino acids to the naturally occurring transaminase polypeptide as well as insertions of one or more amino acids to other improved transaminase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length transaminase polypeptide, for example the polypeptide of SEQ ID NO:4.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved transaminase enzymes may be present within a cell, present in the cellular medium, or prepared in various forms, such as lysates or isolated preparations. As such, in some embodiments, the improved transaminase enzyme can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure transaminase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved transaminases polypeptide is a substantially pure polypeptide composition.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The $T_m$ values for polynucleotides can be calculated using known methods for predicting melting temperatures (see, e.g., Baldino et al., Methods Enzymology 168:761-777; Bolton et al., 1962, Proc. Natl. Acad. Sci. USA 48:1390; Bresslauer et ah, 1986, Proc. Natl. Acad. Sci USA 83:8893-8897; Freier et ah, 1986, Proc. Natl. Acad. Sci USA 83:9373-9377; Kierzek et ah, Biochemistry 25:7840-7846; Rychlik et ah, 1990, Nucleic Acids Res 18:6409-6412 (erratum, 1991, Nucleic Acids Res 19:698); Sambrook et ah, supra); Suggs et ah, 1981, In Developmental Biology Using Purified Genes (Brown et ah, eds.), pp. 683-693, Academic Press; and Wetmur, 1991, Crit Rev Biochem Mol Biol 26:227-259. All publications incorporate herein by reference). In some embodiments, the polynucleotide encodes the polypeptide disclosed herein and hybridizes under defined conditions, such as moderately stringent or highly stringent conditions, to the complement of a sequence encoding an engineered transaminase enzyme of the present disclosure.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA; with greater than about 90% identity to target-polynucleotide. Exemplary moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the transaminases enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; CodonW, John Peden, University of Nottingham; Mclnerney, J. O, 1998, Bioinformatics 14:372-73; Stenico et al., 1994, Nucleic Acids Res. 222437-46; Wright, F., 1990, Gene 87:23-29). Codon usage tables are available for a growing list of organisms (see for example, Wada et al., 1992, Nucleic Acids Res. 20:2111-2118; Nakamura et al., 2000, Nucl. Acids Res. 28:292; Duret, et al., supra; Henaut and Danchin, "*Escherichia coli* and *Salmonella,*" 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (EST), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, Methods Enzymol. 266:259-281; Tiwari et al., 1997, Comput. Appl. Biosci. 13:263-270).

"Control sequence" is defined herein to include all components, which are necessary or advantageous for the expression of a polynucleotide and/or polypeptide of the present disclosure. Each control sequence may be native or foreign to the polynucleotide of interest. Such control sequences include, but are not limited to, a leader, polyadenylation sequence, propeptide sequence, promoter, signal peptide sequence, and transcription terminator.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" is a nucleic acid sequence that is recognized by a host cell for expression of a polynucleotide of interest, such as a coding sequence. The control sequence may comprise an appropriate promoter sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

6.2 Detailed Description of Embodiments

In the embodiments herein, the engineered transaminases are improved in their capability of stereoselectively converting ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine as compared to the transaminase of SEQ ID NO:2. Transaminases, including those described herein, typically contain a coenzyme, pyridoxal phosphate (PLP), which participates in the transamination reaction. PLP can be provided by the host cell in which the polypeptide is synthesized, or provided by adding PLP to a solution of the polypeptide. While the transaminase is described with respect to the amino acid sequence, it will be understood by those skilled in the art that the active polypeptide contains PLP or a suitable analog as a coenzyme.

In some embodiments, the improvement in enzyme activity is with respect to another engineered transaminase, such as the polypeptide of SEQ ID NO:4. The improved activity on the ketoamide substrate can be manifested by an increase in the amount of substrate converted to product (e.g., percent conversion) by the engineered enzyme relative to a reference enzyme (e.g., the wild-type) under defined conditions. The improved activity can include an increased rate of product formation resulting in an increase in conversion of ketoamide substrate to product in a defined time under a defined condition. The increase in activity (e.g., increased percent conversion and/or conversion rate) may also be characterized by conversion of substrate to the same amount of product with a lower amount of enzyme. The amount of product can be assessed by a variety of techniques, for example, separation of the reaction mixture (e.g., by chromatography) and detection of the separated product by UV absorbance or tandem mass spectroscopy (MS/MS) (see, e.g., Example 4). An exemplary method of UV detection of product uses an incident wavelength of 210 nm and a path length of 1.0 cm, which has a detection limit for sitagliptin of about 5 μg/mL. UV detection of product generally follows separation of the reaction mixture by chromatography, particularly HPLC in a reverse phase chromatographic medium, for example Agilent Eclipse XDB-C8 column (4.6×150 mm, 5 μm), using an eluent of 45:55 10 mM $NH_4Ac$/MeCN at a flow rate of 1.5 ml/min and a column temperature 40° C. In some embodiments, the UV detection uses an incident wavelength of 268 nm, which has a detection limit similar to the detection limit at 210 nm.

In some embodiments, the improvement in enzyme activity is equal to or greater than the activity of the polypeptide of SEQ ID NO:4 under defined reaction condition, such as provided in Example 6 or 7. An exemplary defined reaction condition for comparison to the activity of SEQ ID NO:2 or SEQ ID NO:4 is about 2 g/L ketoamide substrate, about 0.5 M isopropylamine, about 22° C., about pH 7.5, about 5% DMSO, about 100 μM PLP, and about 20 mg/mL of transaminase polypeptide, as given below in the description of reaction conditions for the transaminases listed in Table 2. Defined reaction conditions for comparison to certain engineered transaminases are also provided in the description for the transaminases listed on Table 2, and in the corresponding descriptions in Examples 7 to 11. In some embodiments, the engineered transaminases have at least 1.5 times, 2 times, 3 times, 4 times, 5 times, 6 times, 7 times, 8 times, 9 times, 10 times, 15 times, 20 times, 30 times, 40 times, 50 times, 75 times, 100 times, 150 times, 200 times, 300 times, 400 times, 500 times, 1000 times, 1500 times, 2000 times or greater than 2000 times the activity of the polypeptide of SEQ ID NO:4 under the defined reaction condition. Given that the transaminase enzyme of SEQ ID NO:2 does not act measurably on the ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one, an engineered transaminase with activity equal to or greater than SEQ ID NO:4 in converting the ketoamide substrate to the corresponding product is improved over the enzyme represented by SEQ ID NO:2.

In some embodiments, the improved enzymatic activity is also associated with other improvements in enzyme property. In some embodiments, the improvement in enzyme property is with respect to thermal stability, such as at 45° C. or higher.

In some embodiments, the improved enzymatic activity is also associated with improvements in solvent stability, such as in about 25 to about 40% or about 25 to about 50% dimethylsulfoxide (DMSO). In some embodiments, the improved transaminase is resistance to inactivation by a reaction component, such as the amino group donor. In some embodiments, the engineered transaminases are stable to 1 M or up to 2 M isopropylamine.

In some embodiments, the improved transaminase polypeptide is also capable of converting ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine with at least 70%, 80%, 85%, 90%, 91%, 92%, 93%, 94%, 95%, 96%, 97%, 98%, or 99% or greater enantiomeric excess (e.e.).

In some embodiments, the engineered transaminase polypeptides of the present disclosure are capable of converting the ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to the product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine with an activity that is equal to or greater than the activity of the polypeptide of SEQ ID NO:4 in the presence of an amino group donor, particularly isopropylamine, and comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:4.

In some embodiments, the engineered transaminase polypeptides of the present disclosure are capable of converting the ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to the product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in the presence of an amino group donor, particularly isopropylamine, with an activity that is equal to or greater than the polypeptide of SEQ ID NO:4 and comprises an amino acid sequence that is at least 80%, 85%, 86%, 87%, 88%, 89%, 90%, 91%, 92%, 93%, 94%, 95%, 96%, 97%, 98%, 99% or more identical to a reference sequence listed in Table 2, for example, SEQ ID NO: 68, 70, 72, 74, 76, 78, 80, 82, 84, 86, 88, 90, 92, 94, 96, 98, 100 or 102, as further described below.

In some embodiments, the engineered transaminase polypeptides comprise an amino acid sequence that has one or more residue differences as compared to a transaminase reference sequence. The residue differences can be non-conservative substitutions, conservative substitutions, or a combination of non-conservative and conservative substitutions. With respect to the residue differences and the descriptions of residue positions, the transaminases provided herein can be described in reference to the amino acid sequence of the naturally occurring transaminase of *Arthrobacter* sp KNK168 or the transaminase of SEQ ID NO:2, or an engineered transaminase, such as the polypeptide of SEQ ID NO:4. For the descriptions herein, the amino acid residue position in the reference sequence is determined in the transaminase beginning from the initiating methionine (M) residue (i.e., M represents residue position 1), although it will be understood by the skilled artisan that this initiating methionine residue may be removed by biological processing machinery, such as in a host cell or in vitro translation system, to generate a mature protein lacking the initiating methionine residue.

The polypeptide sequence position at which a particular amino acid or amino acid change ("residue difference") is present is sometimes described herein as "Xn", or "position n", where n refers to the residue position with respect to the reference sequence.

A specific substitution mutation, which is a replacement of the specific residue in a reference sequence with a different specified residue may be denoted by the conventional notation "X(number)Y", where X is the single letter identifier of the residue in the reference sequence, "number" is the residue position in the reference sequence, and Y is the single letter identifier of the residue substitution in the engineered sequence.

In some embodiments, the residue differences can occur at one or more of the following residue positions: X4; X5; X8; X18; X25; X26; X27; X28; X30; X41; X42; X48; X49; X50; X54; X55; X60; X61; X62; X65; X69; X81; X94; X96; X102; X117; X120; X122; X124; X126; X136; X137; X138; X146; X148; X150; X152; X155; X156; X160; X163; X164; X169; X174; X178; X195; X199; X204; X208; X209; X211; X215; X217; X223; X225; X230; X252; X269; X273; X282; X284; X292; X297; X302; X306; X321; and X329. In some embodiments, the residue differences or combinations thereof, are associated with the improved enzyme properties. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at residue positions other than those specific positions denoted by "Xn" listed above. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other amino acid residue positions. In some embodiments, the residue differences at other residue positions comprise substitutions with conservative amino acid residues.

In the embodiments herein, the residue differences as compared to SEQ ID NO:2 at residue positions affecting substrate binding on the transaminase allows accommodation of the ketoamide substrate of structural formula (I), further described below, in particular the ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one. Without being bound by theory, at least two regions, a first substrate binding region and a second substrate binding region, interact with different structural elements of the ketoamide substrate. The first binding region comprises residue positions X62, X136, X137, X195, X199, X208, X209, X223, X225, and X282, while the second binding region comprises residue positions X69, X122, and X284. Accordingly, the transaminase polypeptides herein have one or more residue differences at residue positions comprising X62, X69, X122, X136, X137, X195, X199, X208, X209, X223, X225, X282, and X284. In some embodiments, the transaminase polypeptides herein have at least two or more, three or more, four or more, five or more, or six or more residue differences at the specified residue positions associated with substrate binding.

In some embodiments, the residue differences as compared to SEQ ID NO:2 are at one or more of residue positions forming a first substrate binding region comprised of residue positions X62, X136, X137, X195, X199, X208, X209, X223, X225, and X282. Accordingly, in some embodiments, the engineered transaminase comprises an amino acid sequence that includes at least one residue difference as compared to SEQ ID NO:2 at residue positions X62, X136, X137, X195, X199, X208, X209, X223, X225, and X282.

In some embodiments, the residue differences as compared to SEQ ID NO:2 are at one or more of residue positions forming a second substrate binding region comprised of residue positions X69, X122, and X284. Accordingly, in some embodiments, the engineered transaminase comprises an amino acid sequence that includes at least one residue difference as compared to SEQ ID NO:2 at residue positions X69, X122, and X284.

In some embodiments, the engineered transaminase comprises an amino acid sequence that includes residue differences at the first binding region in combination with residue differences at the second binding region. Accordingly, in some embodiments, the engineered transaminase comprises an amino acid sequence that includes one or more residue difference as compared to SEQ ID NO:2 at residue positions X62, X136, X137, X195, X199, X208, X209, X223, X225, and X282 in combination with one or more residue difference as compared to SEQ ID NO:2 at residue positions X69, X122, and X284.

In some embodiments of the engineered transaminases of the disclosure, the amino acid residues at a residue position can be can be defined in terms of the amino acid "features" (e.g., type or property of amino acids) that can appear at that position. Thus, in some embodiments the amino acid residues at the positions specified above can be selected from the following features: X4 is an aromatic residue; X5 is a basic residue; X8 is a constrained residue; X18 is a cysteine (C) or an aliphatic residue; X25 is a polar residue; X26 is an aromatic or constrained residue; X27 is a polar residue; X28 is a constrained residue; X30 is polar or non-polar residue; X41 is a constrained or polar residue; X42 is non-polar residue; X48 is a polar, acidic, aliphatic or non-polar residue; X49 is a polar residue; X50 is an aliphatic residue; X54 is a constrained residue; X55 is an aliphatic residue; X60 is an aromatic residue; X61 is an aromatic residue; X62 is an aromatic or polar residue; X65 is an aliphatic residue; X69 is a cysteine (C) or non-polar, polar, or aliphatic residue; X81 is a non-polar residue; X94 is an aliphatic residue; X96 is an aliphatic residue; X102 is an aliphatic or basic residue; X117 is a non-polar residue; X120 is an aromatic residue; X122 is a constrained, non-polar or aliphatic residue; X124 is a polar or constrained residue; X126 is a polar residue; X136 is an aromatic residue; X137 is a polar or aliphatic residue; X138 is a basic or constrained residue; X146 is a basic residue; X148 is an aliphatic or aromatic residue; X150 is aromatic, constrained or polar residue; X152 is cysteine (C), non-polar, aliphatic, or polar residue; X155 is non-polar or polar residue; X156 is a polar residue; X160 is an aliphatic residue; X163 is an aliphatic or constrained residue; X164 is an aliphatic or constrained residue; X169 is an aliphatic residue; X174 is an aliphatic residue; X178 is a polar residue; X195 is an aromatic or polar residue; X199 is an aliphatic or aromatic residue; X204 is an aliphatic residue; X208 is cysteine (C) or a constrained, non-polar, aromatic, polar, or basic residue; X209 is an aliphatic residue; X211 is an aliphatic residue; X215 is a cysteine (C); X217 is a polar residue; X223 is a constrained residue; X225 is an aromatic residue; X230 is an aliphatic residue; X252 is an aromatic or aliphatic residue; X269 is a constrained residue; X273 is an aromatic residue; X282 is a polar residue; X284 is a non-polar residue; X292 is a polar residue; X297 is a polar residue; X302 is an aliphatic residue; X306 is an aliphatic residue; X321 is a constrained residue, and X329 is a constrained or aromatic residue. In some embodiments, where the amino acid residue at the corresponding residue position of the reference sequence (e.g., SEQ ID NO:2) are encompassed within the category of amino acids described for the specified position, a different amino acid within that amino acid category can be used in light of the guidance provided herein.

In some embodiments, the amino acid residue at the residue positions specified above can be selected from the following features: X4 is Y, F, or W, particularly Y; X5 is K or R, particularly K; X8 is H or P, particularly P; X18 is C, A, V, or I, particularly C or I; X25 is N, Q, S, or T, particularly Q; X26 is F, W, H or P, particularly H; X27 is N, Q, S, or T, particularly T; X28 is P or H, particularly P; X30 is N, Q, S, T, G, M, A, V, F or I, particularly Q or M; X41 is P, H, N, Q, S, or T, particularly H or S; X42 is G, M, A, V, F or I, particularly G; X48 is N, Q, S, T, D, E, G, M, A, V, F, or I, particularly Q, D, V, G, or A; X49 is N, Q, or T, particularly T; X50 is A, V, F or I, particularly F; X54 is P or H; X55 is A, V, or F, particularly V; X60 is F or W, particularly F; X61 is Y, F, or W, particularly Y; X62 is S, T, N, Q, Y, F, or W, particularly T, Y or F; X65 is A, L or I, particularly A; X69 is C, G, M, A, L I, S, T, N or Q, particularly G, C, T, A, or S; X81 is G, M, A, V, L, I, particularly G; X94 is A, V, F or I, particularly I or L; X96 is A, V or F, particularly L; X102 is A, V, L, I, K or R, particularly F or K; X117 is G, M, A, V, F or I, particularly G; X120 is Y, W, or F, particularly Y; X122 is G, M, A, V, I, L, P or H, particularly M, I, L, V, or H; X124 is T, N, Q, P, or H, particularly T, H or N; X 126 is N, Q, or T, particularly T; X136 is Y, F or W, particularly Y or F; X137 is S, T, N, Q, A, V, L or I, particularly T or I; X138 is K, P or H, particularly K or P; X146 is K or R, particularly R; X148 is A, V, L I, W, or F, particularly A or F; X150 is F, W, H, P, S, T, N, or Q, particularly F, H, or S; X152 is C, G, M, A, L, I, S, T, N, or Q, particularly G, I, L, S or C; X155 is N, S, T, G, M, A, V, L or I, particularly M, V or T; X156 is N, Q, S, or T, particularly Q; X160 is A, V, L or I, particularly L; X163 is P, H, A, V, or L, particularly H or V; X164 is A, V, L, I, P or H, particularly V or P; X169 is V, L or I, particularly L; X174 is A, V, L or I, particularly A; X178 is S, N, or Q, particularly S; X195 is F, Y, W, S, T, N or Q, particularly F or Q; X199 is A, L, I, Y, F, W, particularly W or I; X204 is A, V, L, or I, particularly A; X208 is H, C, G, K, N, Y, D or S; X209 is V, L or I, particularly L; X211 is A, V, or I, particularly I; X215 is C; X217 is S, T, N or Q, particularly N; X223 is H or P, particularly P; X225 is W or Y, particularly Y; X230 is A, V, or L, particularly V; X252 is A, V, I, Y, F, or W, particularly F; X269 is H or P, particularly P; X273 is Y, F or W, particularly Y; X282 is S, N or Q, particularly S; X284 is G, M, V, L or I, particularly G; X292 is T, N, or Q, particularly T; X297 is S, T, N or Q, particularly S; X302 is A, L, or I, particularly A; X306 is A, L or I, particularly L; X321 is H or P, particularly P; and X329 is H, P, Y, F, or W, particularly H.

In some embodiments, the engineered transaminase polypeptide comprises an amino acid sequence that includes one or more of the following features: residue corresponding to X69 is cysteine (C) or a non-polar, polar, or aliphatic residue; residue corresponding to X122 is a constrained, non-polar or aliphatic residue; residue corresponding to X223 is a constrained residue; and residue corresponding to X284 is a non-polar residue.

In some embodiments, the engineered transaminase polypeptide comprises an amino acid sequence that includes at least the following features: (1) residue corresponding to X69 is C or a non-polar, aliphatic or polar residue, and/or residue corresponding to X284 is a non-polar residue; (2) residue corresponding to X122 is a constrained, non-polar or aliphatic residue; and (3) residue corresponding to X223 is a constrained residue.

In some embodiments, the engineered transaminase polypeptide comprises an amino acid sequence that includes at least the following features: X69 is C or a non-polar, aliphatic or polar residue; X122 is a constrained, non-polar or aliphatic residue; and X223 is a constrained residue.

In some embodiments, the engineered transaminase polypeptide comprises an amino acid sequence that includes at least the following features: X69 is C, G, M, A, L, I, S, T, N or Q, particularly G, C, T, A, or S; X122 is G, M, A, V, L, I, P or H, particularly M, I, V, L, or H; and X223 is H or P, particularly P.

In some embodiments, the engineered transaminase polypeptide comprises an amino acid sequence that includes at least the following features: X122 is a constrained, non-polar or aliphatic residue; X223 is a constrained residue; and X284 is a non-polar residue.

In some embodiments, the engineered transaminase polypeptide comprises an amino acid sequence that includes at least the following features: X122 is G, M, A, V, L, I, P or H, particularly M, I, V, L or H; X223 is H or P, particularly P; and X284 is G, M, V, L or I, particularly G.

In some embodiments, the engineered transaminase polypeptide comprises an amino acid sequence that includes at least the following features: X69 is C or a non-polar, polar or aliphatic residue; X122 is a constrained, non-polar or aliphatic residue; X223 is a constrained residue; and X284 is a non-polar residue.

In some embodiments, the engineered transaminase polypeptide comprises an amino acid sequence that includes at least the following features: X69 is C, G, M, A, L, I, S, T, N or Q, particularly G, C, T, A, or S; X122 is G, M, A, V, L, I, P or H, particularly M, I, V, L, or H; X223 is H or P, particularly P; and X284 is G, M, A, V, L or I, particularly G.

In some embodiments, the engineered transaminase polypeptide comprises an amino acid sequence that includes at least the following features: X69 is C or T; X122 is M or I; X223 is P; and X284 is G.

In some embodiments, the engineered transaminase polypeptides with one or more of the specified features or combinations of features at residue positions X69, X122, X223, and X284, can additionally have one or more residue differences as compared to SEQ ID NO:2 at the following residue positions: X4; X5; X8; X18; X25; X26; X27; X28; X30; X41; X42; X48; X49; X50; X54; X55; X60; X61; X62; X65; X81; X94; X96; X102; X117; X120; X124; X126; X136; X137; X138; X146; X148; X150; X152; X155; X156; X160; X163; X164; X169; X174; X178; X195; X199; X204; X208; X209; X211; X215; X217; X225; X230; X252; X269; X273; X282, X292; X297; X302; X306; X321; and X329. In additions to residue positions X69, X122, X223, and X284, these other residue positions are associated with effects on various properties of the transaminase polypeptide, and thus can have residue differences as compared to SEQ ID NO:2 to effect desirable changes in enzyme properties.

As noted above, residue positions X62, X136, X137, X195, X199, X208, X209, X225, and X282 along with residue positions X69, X122, X223, and X284, are associated with binding of the substrate to the enzyme, and thus the transaminase polypeptide can have residue differences at these recited positions as compared to SEQ ID NO:2 to effect desirable changes in enzyme activity.

Residue positions X4, X5, X8, X26, X48, X60, X65, X81, X96, X102, X124, X160, X163, X169, X174, X178, X211, X217, X225, X230, X252, X269, X273, X292, X297, X306, X321, X329 are also associated with additional increases in enzyme activity, and thus the transaminase polypeptide can have residue differences at these recited positions as compared to SEQ ID NO:2 to effect additional desirable changes in enzyme activity, for example increase in efficiency of conversion at high substrate loading conditions.

Residue positions X18, X25, X27, X28, X30, X41, X42, X49, X50, X54, X55, X117, X120, X126, X138, X146, X148, X150, X152, X155, X156, X164, X204, X302 are associated also with increases in thermostability and/or solvent stability, such as DMSO, and thus the transaminase polypeptide can have residue differences at these recited positions as compared to SEQ ID NO:2 to effect desirable changes in thermostability and/or solvent stability.

Residue positions X61, X94, X215 are associated also with the ability to carry out the reaction at high concentrations of amino donor isopropylamine, and thus the transaminase polypeptide can have residue differences at these recited positions as compared to SEQ ID NO:2 to effect increase in efficiency of conversion at high (e.g., 1-2 M) concentrations of isopropylamine.

It is to be understood that the residue differences from SEQ ID NO:2 at residue positions associated with the various properties of the enzymes can be used in various combinations to form transaminase polypeptides having desirable enzymatic characteristics, for example combination of increases in enzyme activity, solvent and temperate stability, and utilization of amino donor. Exemplary combinations are described herein.

In some embodiments, the amino acid residues for the specified residue positions can be selected according to the descriptions above. For example, the amino acid residues can be selected based on the following features: X4 is an aromatic residue; X5 is a basic residue; X8 is a constrained residue; X18 is a cysteine (C) or an aliphatic residue; X25 is a polar residue; X26 is an aromatic or constrained residue; X27 is a polar residue; X28 is a constrained residue; X30 is a polar or non-polar residue; X41 is a constrained or polar residue; X42 is a non-polar residue; X48 is a polar, acidic, aliphatic or non-polar residue; X49 is a polar residue; X50 is an aliphatic residue; X54 is a constrained residue; X55 is an aliphatic residue; X60 is an aromatic residue; X61 is an aromatic residue; X62 is an aromatic or polar residue; X65 is an aliphatic residue; X81 is a non-polar residue; X94 is an aliphatic residue; X96 is an aliphatic residue; X102 is an aliphatic or basic residue; X117 is a non-polar residue; X120 is an aromatic residue; X124 is a polar or constrained residue; X126 is a polar residue; X136 is an aromatic residue; X137 is a polar or aliphatic residue; X138 is a basic or constrained residue; X146 is a basic residue; X148 is an aliphatic or aromatic residue; X150 is an aromatic, constrained or polar residue; X152 is a cysteine (C), non-polar, aliphatic, or polar residue; X155 is a non-polar or polar residue; X156 is a polar residue; X160 is an aliphatic residue; X163 is an aliphatic or constrained residue; X164 is an aliphatic or constrained residue; X169 is an aliphatic residue; X174 is an aliphatic residue; X178 is a polar residue; X195 is an aromatic or polar residue; X199 is an aliphatic or aromatic residue; X204 is an aliphatic residue; X208 is a cysteine (C) or a constrained, non-polar, aromatic, polar, or basic residue; X209 is an aliphatic residue; X211 is an aliphatic residue; X215 is C; X217 is a polar residue; X225 is an aromatic residue; X230 is an aliphatic residue; X252 is an aromatic or aliphatic residue; X269 is a constrained residue; X273 is an aromatic residue; X282 is a polar residue; X292 is a polar residue; X297 is a polar residue; X302 is an aliphatic residue; X306 is an aliphatic residue; X321 is a constrained residue; and X329 is a constrained or aromatic residue. Specific amino acid residues that can be used at these residue positions are described above.

In some embodiments, the engineered transaminase having the features at one or more residue positions X69, X122, X223, and X284 as described above, can have additionally one or more of the following features: X26 is an aromatic or constrained residue; X61 is an aromatic residue; X62 is an aromatic or polar residue; X65 is an aliphatic residue; X94 is an aliphatic residue; X136 is an aromatic residue; X137 is a polar or aliphatic residue; X199 is an aliphatic or aromatic residue; X209 is an aliphatic residue; X215 is C; and X282 is a polar residue.

In some embodiments, in addition to the preceding features, the transaminase amino acid sequence can include additionally one or more of the following features: X8 is a constrained residue; X60 is an aromatic residue; X81 is a non-polar or small residue; X96 is an aliphatic residue;

X124 is a polar or constrained residue; X169 is an aliphatic residue; X217 is a polar residue; X269 is a constrained residue; X273 is an aromatic residue; X297 is a polar residue; and X321 is a constrained residue.

In some embodiments, in addition to the preceding features, the transaminase amino acid sequence can include additionally one or more of the following features: X4 is an aromatic residue; X48 is a polar, acidic, aliphatic or non-polar residue; X102 is an aliphatic or basic residue; X150 is aromatic, constrained or polar residue; X152 is C or a non-polar, aliphatic or polar residue; X160 is an aliphatic residue; X163 is an aliphatic or constrained residue; X174 is an aliphatic residue; X178 is a polar residue; X195 is an aromatic or polar residue; X208 is C or a constrained, non-polar, aromatic, polar, or basic residue; X211 is an aliphatic residue; X225 is an aromatic residue; X230 is an aliphatic residue; X252 is an aromatic or aliphatic residue; X292 is a polar residue; X306 is an aliphatic residue; and X329 is a constrained or aromatic residue.

In some embodiments, the engineered transaminase having the features at one or more or combinations of features at residue positions X69, X122, X223, and X284 as described above, includes at least the following additional features: X26 is an aromatic or constrained residue, and/or X62 is an aromatic or polar residue; X65 is an aliphatic residue; X136 is an aromatic residue; X199 is an aliphatic or aromatic residue; and X209 is an aliphatic residue.

In some embodiments, the engineered transaminase having the features at one or more residue positions X69, X122, X223, and X284 as described above, includes at least the following additional features: X61 is an aromatic residue; X62 is an aromatic or polar residue; X65 is an aliphatic residue; X94 is an aliphatic residue; X136 is an aromatic residue; X199 is an aliphatic or aromatic residue; X209 is an aliphatic residue; X215 is C, and X282 is a polar residue.

In some embodiments, the engineered transaminase having the features at one or more residue positions X69, X122, X223, and X284 as described above, includes at least the following additional features: X8 is a constrained residue; X61 is an aromatic residue; X62 is an aromatic or polar residue; X65 is an aliphatic residue; X81 is a non-polar or small residue; X94 is an aliphatic residue; X136 is an aromatic residue; X199 is an aliphatic or aromatic residue; X209 is an aliphatic residue; X215 is a C; X217 is a polar residue; X269 is a constrained residue; X282 is a polar residue X297 is a polar residue; and X321 is a constrained residue.

In some embodiments, the engineered transaminase having the features at one or more residue positions X69, X122, X223, and X284 as described above, includes at least the following additional features: X8 is a constrained residue; X60 is an aromatic residue; X61 is an aromatic residue; X62 is an aromatic or polar residue; X65 is an aliphatic residue; X81 is a non-polar residue; X94 is an aliphatic residue; X96 is an aliphatic residue; X124 is a polar or constrained residue; X136 is an aromatic residue; X169 is an aliphatic residue; X199 is an aliphatic or aromatic residue; X209 is an aliphatic residue; X215 is C; X217 is a polar residue; X269 is a constrained residue; X273 is an aromatic residue. X282 is a polar residue; X297 is a polar residue; and X321 is a constrained residue.

In some embodiments, the engineered transaminase having the features at one or more residue positions X69, X122, X223, and X284 as described above, includes at least the following additional features: X8 is a constrained residue; X60 is an aromatic residue; X61 is an aromatic residue; X62 is an aromatic or polar residue; X65 is an aliphatic residue; X81 is a non-polar residue; X94 is an aliphatic residue; X96 is an aliphatic residue; X124 is a polar or constrained residue; X126 is a polar residue; X136 is an aromatic residue; X150 is an aromatic, constrained or polar residue; X152 is a cysteine (C), non-polar, aliphatic, or polar residue; X169 is an aliphatic residue; X199 is an aliphatic or aromatic residue; X209 is an aliphatic residue; X215 is C; X217 is a polar residue; X269 is a constrained residue; X273 is an aromatic residue. X282 is a polar residue; X297 is a polar residue; and X321 is a constrained residue.

In some embodiments, the engineered transaminase having the features at one or more residue positions X69, X122, X223, and X284 as described above, includes at least the following additional features: X26 is P, H, F, or W, particularly H, and/or X62 is S, T, N, Q, Y, F, or W, particularly T or F; X65 is A, L or I, particularly A; X136 is Y, F or W, particularly Y or F; X199 is A, L, I, Y, F, or W, particularly W or I; and X209 is V, L or I, particularly L.

In some embodiments, the engineered transaminase having the features at one or more residue positions X69, X122, X223, and X284 as described above, includes at least the following additional features: X61 is Y, F, or W, particularly Y; X62 is S, T, N, Q, Y, F, or W, particularly T or F; X65 is A, L or I, particularly A; X94 is A, V, L or I, particularly I or L; X136 is Y, F, or W, particularly Y or F; X199 is A, L, I, Y, F, or W, particularly W or I; X209 is V, L or I, particularly L; X215 is C; and X282 is S, N or Q, particularly S.

In some embodiments, the engineered transaminase having the features at one or more residue positions X69, X122, X223, and X284 as described above, includes at least the following additional features: X8 is H or P, particularly P; X61 is Y, F, or W, particularly Y; X62 is S, T, N Q, Y, F, or W, particularly T or F; X65 is A, L or I, particularly A; X81 is G, M, A, V, L or I, particularly G; X94 is A, V, L or I, particularly I or L; X136 is Y, F, or W, particularly Y or F; X199 is A, L, I, Y, F, or W, particularly W or I; X209 is V, L or I, particularly L; X215 is C; X217 is S, T, N, or Q, particularly N; X269 is H or P, particularly P; X282 is S, N or Q, particularly S. X297 is S, T, N or Q, particularly S; and X321 is H or P, particularly P.

In some embodiments, the engineered transaminase having the features at one or more residue positions X69, X122, X223, and X284 as described above, includes at least the following additional features: X8 is H or P, particularly P; X60 is F or W, particularly F; X61 is Y, F, or W, particularly Y; X62 is Y, F, W, S, T, N or Q, particularly T or F; X65 is A, L or I, particularly A; X81 is G, M, A, V, L or I, particularly G; X94 is A, V, L or I, particularly I or L; X96 is A, V or L, particularly L; X124 is P, H, T, N, or Q, particularly T, H or N; X136 is Y, F or W, particularly Y or F; X169 is V, L, or I, particularly L; X199 is Y, F, W, A, L or I, particularly W or I; X209 is V, L or I, particularly L; X215 is C; X217 is S, T, N or Q, particularly N; X269 is H or P, particularly P; X273 is Y, F, or W, particularly Y; X282 is S, N or Q, particularly S; X297 is S, T, N or Q, particularly S; and X321 is H or P, particularly P.

In some embodiments, the engineered transaminase having the features at one or more residue positions X69, X122, X223, and X284 as described above, includes at least the following additional features: X8 is H or P, particularly P; X60 is F or W, particularly F; X61 is Y, F, or W, particularly Y; X62 is Y, F, W, S, T, N or Q, particularly T or F; X65 is A, L or I, particularly A; X81 is G, M, A, V, L or I, particularly G; X94 is A, V, L or I, particularly I or L; X96 is A, V or L, particularly L; X124 is P, H, T, N, or Q, particularly T, H or N; X 126 is N, Q, or T, particularly T;

X136 is Y, F or W, particularly Y or F; X150 is F, W, H, P, S, T, N, or Q, particularly F, H, or S; X152 is C, G, M, A, L, I, S, T, N, or Q, particularly G, I, L, S or C; X169 is V, L, or I, particularly L; X199 is Y, F, W, A, L or I, particularly W or I; X209 is V, L or I, particularly L; X215 is C; X217 is S, T, N or Q, particularly N; X269 is H or P, particularly P; X273 is Y, F, or W, particularly Y; X282 is S, N or Q, particularly S; X297 is S, T, N or Q, particularly S; and X321 is H or P, particularly P.

In some embodiments, the engineered transaminases comprise an amino acid sequence that includes at least the following features: X122 is a constrained, non-polar or aliphatic residue, particularly M, I, L, V, or H; X223 is a constrained residue, particularly P; X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference amino acid sequence based on SEQ ID NO:2 having the features described for the preceding specified residue positions (i.e. X122; X223; and X284) (e.g., SEQ ID NO:8 or 10), with the proviso that the engineered transaminase polypeptide comprises polypeptide comprises an amino acid sequence that includes at least the features described for the specified residues.

In some embodiments, the engineered transaminases comprise an amino acid sequence that includes at least the following features: X69 is C or a non-polar, aliphatic or polar residue, particularly G, C, T, A, or S; X122 is a constrained, non-polar or aliphatic residue, particularly M, I, L, V, or H; X223 is a constrained residue, particularly P; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (i.e., X69; X122; X223; and X284)(e.g., SEQ ID NO:4), with the proviso that the engineered transaminase polypeptide comprises polypeptide comprises an amino acid sequence having at least the features described for the specified residues.

In some embodiments, the engineered transaminases comprise an amino acid sequence that includes at least the following features: X65 is an aliphatic residue, particularly A; X69 is C or a non-polar, aliphatic or polar residue, particularly G, C, T, A, or S; X122 is a constrained, non-polar or aliphatic residue, particularly M, I, L, V, or H; and X223 is a constrained residue, particularly P. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for the preceding specified residue positions (e.g., SEQ ID NO:6), with the proviso that the engineered transaminase polypeptide comprises polypeptide comprises an amino acid sequence that includes at least the features described for the specified residues. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:6.

In some embodiments, the engineered transaminases comprise an amino acid sequence that includes at least the following features: X122 is a constrained, non-polar or aliphatic residue, particularly M, I, L, V, or H; X174 is an aliphatic residue, particularly A; X223 is a constrained residue, particularly P; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO: 12), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO: 12.

In some embodiments, the engineered transaminases comprise an amino acid sequence that includes the following features: In some embodiments, the engineered transaminases comprise an amino acid sequence that includes at least the following features: X26 is an aromatic or constrained residue, particularly H; X65 is an aliphatic residue, particularly A; X69 is C or a non-polar, aliphatic or polar residue, particularly G, C, T, A, or S; X122 is a constrained, non-polar or aliphatic residue, particularly M, I, L, V, or H; X223 is a constrained residue, particularly P; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO: 14), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO: 14.

In some embodiments, the engineered transaminases comprise an amino acid sequence that includes the following features: In some embodiments, the engineered transaminases comprise an amino acid sequence that includes at least the following features: X26 is an aromatic or constrained residue, particularly H; X62 is an aromatic or polar residue, particularly T, Y or F; X65 is an aliphatic residue, particularly A; X69 is C or a non-polar, aliphatic or polar residue, particularly G, C, T, A, or S; X122 is a constrained, non-polar or aliphatic residue, particularly M, I, L, V, or H; X178 is a polar residue, particularly S; X199 is an aliphatic or aromatic residue, particularly W or I, particularly X223 is a constrained residue, particularly P; X225 is an aromatic residue, particularly Y, X282 is a polar residue, particularly S; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO: 16), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO: 16.

In some embodiments, the engineered transaminases comprise an amino acid sequence that includes the following features: In some embodiments, the engineered transaminases comprise an amino acid sequence that includes at least the following features: X26 is an aromatic or constrained residue, particularly H; X62 is an aromatic or polar residue, particularly T, Y or F; X65 is an aliphatic residue, particularly A; X69 is C or a non-polar, aliphatic or polar residue, particularly G, C, T, A, or S; X122 is a constrained, non-polar or aliphatic residue, particularly M, I, L, V, or H; X136 is an aromatic residue, particularly Y or F; X199 is an aliphatic or aromatic residue, particularly W or I; X209 is an aliphatic residue, particularly L; X223 is a constrained residue, particularly P; X225 is an aromatic residue, particularly Y, X282 is a polar residue, particularly S; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO: 18), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO: 18.

In some embodiments, the engineered transaminases comprise an amino acid sequence that includes the following features: In some embodiments, the engineered transaminases comprise an amino acid sequence that includes at least the following features: X26 is an aromatic or constrained residue, particularly H; X62 is an aromatic or polar residue, particularly T, Y or F; X65 is an aliphatic residue, particularly A; X69 is C or a non-polar, aliphatic or polar residue, particularly G, C, T, A, or S; X122 is a constrained, non-polar or aliphatic residue, particularly M, I, L, V, or H; X136 is an aromatic residue, particularly Y or F; X137 is a polar or aliphatic residue, particularly T or I; X199 is an aliphatic or aromatic residue, particularly W or I; X209 is an aliphatic residue, particularly L; X223 is a constrained residue, particularly P; X282 is a polar residue, particularly S; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions.

In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:20, 22, 28, 30, 32, 34, 38 or 40), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:20, 22, 28, 30, 32, 34, 38 or 40.

In some embodiments, the engineered transaminases comprise an amino acid sequence that includes the following features: In some embodiments, the engineered transaminases comprise an amino acid sequence that includes at least the following features: X26 is an aromatic or constrained residue, particularly H; X62 is an aromatic or polar residue, particularly T, Y or F; X65 is an aliphatic residue, particularly A; X69 is C or a non-polar, aliphatic or polar residue, particularly G, C, T, A, or S; X122 is a constrained, non-polar or aliphatic residue, particularly M, I, L, V, or H; X136 is an aromatic residue, particularly Y or F; X137 is a polar or aliphatic residue, particularly T or I; X199 is an aliphatic or aromatic residue, particularly W or I; X209 is an aliphatic residue, particularly L; X223 is a constrained residue, particularly P; X225 is an aromatic residue, particularly Y, X282 is a polar residue, particularly S; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:24), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:24.

In some embodiments, the engineered transaminases comprise an amino acid sequence that includes the following features: In some embodiments, the engineered transaminases comprise an amino acid sequence that includes at least the following features: X26 is an aromatic or constrained residue, particularly H; X65 is an aliphatic residue, particularly A; X69 is C or a non-polar, aliphatic or polar residue, particularly G, C, T, A, or S; X122 is a constrained, non-polar or aliphatic residue, particularly M, I, L, V, or H; X136 is an aromatic residue, particularly Y or F; X137 is a polar or aliphatic residue, particularly T or I; X174 is an aliphatic residue, particularly A; X199 is an aliphatic or aromatic residue, particularly W or I; X209 is an aliphatic residue, particularly L; X223 is a constrained residue, particularly P; X230 is an aliphatic residue, particularly V; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions.

In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:26), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:26.

In some embodiments, the engineered transaminases comprise an amino acid sequence that includes the following features: In some embodiments, the engineered transaminases comprise an amino acid sequence that includes at least the following features: X26 is an aromatic or constrained residue, particularly H; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X122 is a constrained, non-polar or aliphatic residue, particularly M, I, L, V, or H; X136 is an aromatic residue, particularly Y or F; X137 is a polar or aliphatic residue, particularly T or I; X199 is an aliphatic or aromatic residue, particularly W or I; X209 is an aliphatic residue, particularly L; X223 is a constrained residue, particularly P; X282 is a polar residue, particularly S; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:36), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:36.

In some embodiments, the engineered transaminases comprise an amino acid sequence that includes the following features: In some embodiments, the engineered transaminases comprise an amino acid sequence that includes at least the following features: X4 is an aromatic residue, particularly Y; X26 is an aromatic or constrained residue, particularly H; X62 is an aromatic or polar residue, particularly T, Y or F; X65 is an aliphatic residue, particularly A; X69 is C or a non-polar, aliphatic or polar residue, particularly G, C, T, A, or S; X94 is an aliphatic residue, particularly I or L; X122 is a constrained, non-polar or aliphatic residue, particularly M, I, L, V, or H; X136 is an aromatic residue, particularly Y or F; X137 is a polar or aliphatic residue, particularly T or I; X199 is an aliphatic or aromatic residue, particularly W or I; X209 is an aliphatic residue, particularly F; X215 is C; X223 is a constrained residue, particularly P; X282 is a polar residue, particularly S; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions.

In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:42), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:42.

In some embodiments, the engineered transaminase comprises an amino acid sequence that includes the following features: X62 is an aromatic or polar residue, particularly T, Y or F; X65 is an aliphatic residue, particularly A; X69 is C or a non-polar, aliphatic or polar residue, particularly G, C, T, A, or S; X94 is an aliphatic residue, particularly I or L; X122 is a constrained, non-polar or aliphatic residue, particularly M, I, L, V, or H; X136 is an aromatic residue, particularly Y or F; X137 is a polar or aliphatic residue, particularly T or I; X199 is an aliphatic or aromatic residue, particularly W or I; X209 is an aliphatic residue, particularly F; X215 is a C; X223 is a constrained residue, particularly P; X282 is a polar residue, particularly S; and X284 is a non-polar residue, particularly G.

In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO: 44, 46, or 48), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:44, 46, or 48.

In some embodiments, the engineered transaminase comprises an amino acid sequence that includes the following features: X8 is a constrained residue, particularly P; X62 is an aromatic or polar residue, particularly T, Y or F; X65 is an aliphatic residue, particularly A; X69 is C or a non-polar, aliphatic or polar residue, particularly G, C, T, A, or S; X94 is an aliphatic residue, particularly I or L; X122 is a constrained, non-polar or aliphatic residue, particularly M, I, L, V, or H; X136 is an aromatic residue, particularly Y or F; X137 is a polar or aliphatic residue, particularly T or I; X199 is an aliphatic or aromatic residue, particularly W or I; X209 is an aliphatic residue, particularly L; X215 is a cysteine (C); X223 is a constrained residue, particularly P; X282 is a polar residue, particularly S; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO: 50), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:50.

In some embodiments, the engineered transaminase comprises an amino acid sequence that includes the following features: X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X94 is an aliphatic residue, particularly I or L; X122 is a constrained, non-polar or aliphatic residue, particularly M, I, L, V, or H; X136 is an aromatic residue, particularly Y or F; X137 is a polar or aliphatic residue, particularly T or I; X152 is C, non-polar, aliphatic, or polar residue, particularly G, I, L, S or C; X199 is an aliphatic or aromatic residue, particularly W or I; X209 is an aliphatic residue, particularly L; X215 is a C; X223 is a constrained residue, particularly P; X282 is a polar residue, particularly S; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO: 52), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:52.

In some embodiments, the engineered transaminase comprises an amino acid sequence that includes the following features: X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X94 is an aliphatic residue, particularly I or L; X122 is a constrained, non-polar or aliphatic residue, particularly M, I, L, V, or H; X136 is an aromatic residue, particularly Y or F; X137 is a polar or aliphatic residue, particularly T or I; X199 is an aliphatic or aromatic residue, particularly W or I; X209 is an aliphatic residue, particularly L; X215 is a C; X223 is a constrained residue, particularly P; X282 is a polar residue, particularly S; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO: 54 or 56), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:54 or 56.

In some embodiments, the engineered transaminase comprises an amino acid sequence that includes the following features: X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X94 is an aliphatic residue, particularly I or L; X122 is a constrained, non-polar or aliphatic residue, particularly M, I, L, V, or H; X136 is an aromatic residue, particularly Y or F; X199 is an aliphatic or aromatic residue, particularly W or I; X209 is an aliphatic residue, particularly L; X215 is a C; X223 is a constrained residue, particularly P; X282 is a polar residue, particularly S; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO: 58 or 60), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:58 or 60.

In some embodiments, the engineered transaminase comprises an amino acid sequence that includes the following features: X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X94 is an aliphatic residue, particularly I or L; X122 is a constrained, non-polar or aliphatic residue, particularly M, I, L, V, or H; X136 is an aromatic residue, particularly Y or F; X137 is a polar or aliphatic residue, particularly T or I; X160 is an aliphatic residue, particularly L; X169 is an aliphatic residue, particularly L; X199 is an aliphatic or aromatic residue, particularly W or I; X209 is an aliphatic residue, particularly L; X215 is C; X223 is a constrained residue, particularly P; X269 is a constrained residue, particularly P; X282 is a polar residue, particularly S; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:62), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:62.

In some embodiments, the engineered transaminase comprises an amino acid sequence that includes the following features: X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X94 is an aliphatic residue, particularly I or L; X122 is a constrained, non-polar or aliphatic residue, particularly M, I, L, V, or H; X136 is an aromatic residue, particularly Y or F; X137 is a polar or aliphatic residue, particularly T or I; X169 is an aliphatic residue, particularly L; X199 is an aliphatic or aromatic residue, particularly W or I; X209 is an aliphatic residue, particularly L; X215 is C; X223 is a constrained residue, particularly P; X282 is a polar residue, particularly S; X284 is a non-polar residue, particularly G; and X306 is an aliphatic residue, particularly L. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:64), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:64.

In some embodiments, the engineered transaminase comprises an amino acid sequence that includes the following features: X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X94 is an aliphatic residue, particularly I or L; X102 is an aliphatic or basic residue, particularly L or K; X122 is a constrained, non-polar or aliphatic residue, particularly M, I, L, V, or H; X136 is an aromatic residue, particularly Y or F; X150 is aromatic, constrained or polar residue, particularly F, H, or S; X152 is C, non-polar, aliphatic, or polar residue, particularly G, I, F, S or C; X199 is an aliphatic or aromatic residue, particularly W or I; X209 is an aliphatic residue, particularly F; X215 is a C; X223 is a constrained residue, particularly P; X282 is a polar residue, particularly S; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:66), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:66.

In some embodiments, the engineered transaminase comprises an amino acid sequence that includes the following features: X8 is a constrained residue, particularly is P; X48 is a polar, acidic, aliphatic or non-polar residue, particularly D, V, G, Q or A; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X81 is a non-polar residue, particularly G; X94 is an aliphatic residue, particularly I or F; X96 is an aliphatic residue, particularly F; X102 is an aliphatic or basic residue, particularly F or K; X122 is a constrained, non-polar or aliphatic residue, particularly M, I, L, V, or H; X136 is an aromatic residue, particularly Y or F; X163 is an aliphatic or constrained residue, particularly H or V; X199 is an aliphatic or aromatic residue, particularly W or I; X209 is an aliphatic residue, particularly L; X211 is an aliphatic residue, particularly I; X215 is a C; X217 is a polar residue, particularly N; X223 is a constrained residue, particularly P; X252 is an aromatic or aliphatic residue, particularly F; X273 is an aromatic residue, particularly Y; X282 is a polar residue, particularly S; and X284 is a non-polar residue, particularly G; and X321 is a constrained residue, particularly P. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:68), with the proviso that the engineered transaminase polypeptide comprises polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:68.

In some embodiments, the engineered transaminase comprises an amino acid sequence that includes the following features: X8 is a constrained residue, particularly is P; X48 is a polar, acidic, aliphatic or non-polar residue, particularly A; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X81 is a non-polar residue, particularly G; X94 is an aliphatic residue, particularly I or L; X122 is a constrained, non-polar or aliphatic residue, particularly M, I, L, V, or H; X136 is an aromatic residue, particularly Y or F; X169 is an aliphatic residue, particularly L; X199 is an aliphatic or aromatic residue, particularly W or I; X209 is an aliphatic residue, particularly L; X215 is C; X217 is a polar residue, particularly N; X223 is a constrained residue, particularly P; X269 is a constrained residue, particularly P; X282 is a polar residue, particularly S; X284 is a non-polar residue, particularly G; X297 is a polar residue, particularly S; and X321 is a constrained residue, particularly P. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:70), with the proviso that the engineered transaminase polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:70.

In some embodiments, the engineered transaminase comprises an amino acid sequence that includes the following features: X8 is a constrained residue, particularly is P; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X94 is an aliphatic residue, particularly I or L; X122 is a constrained, non-polar or aliphatic residue, particularly M, I, L, V, or H; X136 is an aromatic residue, particularly Y or F; X199 is an aliphatic or aromatic residue, particularly W or I; X209 is an aliphatic residue, particularly L; X215 is C; X223 is a constrained residue, particularly P; X282 is a polar residue, particularly S; and X284 is a non-polar residue, particularly G. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions.

In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:72), with the proviso that the engineered transaminase polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:72.

In some embodiments, the engineered transaminase comprises an amino acid sequence that includes the following features: X8 is a constrained residue, particularly is P; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X81 is a non-polar residue, particularly G; X94 is an aliphatic residue, particularly I or L; X96 is an aliphatic residue, particularly L; X122 is a constrained, non-polar or aliphatic residue, particularly M, I, L, V, or H; X136 is an aromatic residue, particularly Y or F; X178 is a polar residue, particularly S; X199 is an aliphatic or aromatic residue, particularly W or I; X209 is an aliphatic residue, particularly L; X215 is C; X223 is a constrained residue, particularly P; X269 is a constrained residue, particularly P; X282 is a polar residue, particularly S; X284 is a non-polar residue, particularly G; X297 is a polar residue, particularly S; and X321 is a constrained residue, particularly P. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:74), with the proviso that the engineered transaminase polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:74.

In some embodiments, the engineered transaminase comprises an amino acid sequence that includes the following features: X8 is a constrained residue, particularly is P; X60 is an aromatic residue, particularly F; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X81 is a non-polar residue, particularly G; X94 is an aliphatic residue, particularly I or L; X96 is an aliphatic residue, particularly L; X122 is a constrained, non-polar or aliphatic residue, particularly M, I, L, V, or H; X136 is an aromatic residue, particularly Y or F; X152 is C or a non-polar, aliphatic, or polar residue, particularly G, I, L, S or C; X178 is a polar residue, particularly S; X199 is an aliphatic or aromatic residue, particularly W or I; X209 is an aliphatic residue, particularly L; X215 is C; X217 is a polar residue, particularly N; X223 is a constrained residue, particularly P; X252 is an aromatic or aliphatic residue, particularly F; X269 is a constrained residue, particularly P; X273 is an aromatic residue, particularly Y; X282 is a polar residue, particularly S; and X284 is a non-polar residue, particularly G; X297 is a polar residue, particularly S; and X321 is a constrained residue, particularly P. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:76), with the proviso that the engineered transaminase polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:76.

In some embodiments, the engineered transaminase comprises an amino acid sequence that includes the following features: X8 is a constrained residue, particularly is P; X60 is an aromatic residue, particularly F; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X81 is a non-polar residue, particularly G; X94 is an aliphatic residue, particularly I or L; X96 is an aliphatic residue, particularly L; X122 is a constrained, non-polar or aliphatic residue, particularly M, I, L, V, or H; X136 is an aromatic residue, particularly Y or F; X169 is an aliphatic residue, particularly L; X178 is a polar residue, particularly S; X199 is an aliphatic or aromatic residue, particularly W or I; X209 is an aliphatic residue, particularly L; X215 is C; X217 is a polar residue, particularly N; X223 is a constrained residue, particularly P; X269 is a constrained residue, particularly P; X282 is a polar residue, particularly S; and X284 is a non-polar residue, particularly G; X292 is a polar residue, particularly T; X297 is a polar residue, particularly S; and X321 is a constrained residue, particularly P. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:78), with the proviso that the engineered transaminase polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:78.

In some embodiments, the engineered transaminase comprises an amino acid sequence that includes the following features: X8 is a constrained residue, particularly is P; X60 is an aromatic residue, particularly F; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X81 is a non-polar residue, particularly G; X94 is an aliphatic residue, particularly I or L; X96 is an aliphatic residue, particularly L; X122 is a constrained, non-polar or aliphatic residue, particularly M, I, L, V, or H; X136 is an aromatic residue, particularly Y or F; X169 is an aliphatic residue, particularly L; X199 is an aliphatic or aromatic residue, particularly W or I; X209 is an aliphatic residue, particularly L; X215 is C; X217 is a polar residue, particularly N; X223 is a constrained residue, particularly P; X269 is a constrained residue, particularly P; X273 is an aromatic residue, particularly Y; X282 is a polar residue, particularly S; and X284 is a non-polar residue, particularly G; X297 is a polar residue, particularly S; and X321 is a constrained residue, particularly P. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions.

In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:80), with the proviso that the engineered transaminase polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:80.

In some embodiments, the engineered transaminase comprises an amino acid sequence that includes the following features: X8 is a constrained residue, particularly is P; X60 is an aromatic residue, particularly F; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X81 is a non-polar residue, particularly G; X94 is an aliphatic residue, particularly I or L; X96 is an aliphatic residue, particularly L; X122 is a constrained, non-polar or aliphatic residue, particularly M, I, L, V, or H; X136 is an aromatic residue, particularly Y or F; X169 is an aliphatic residue, particularly L; X178 is a polar residue, particularly S; X199 is an aliphatic or aromatic residue, particularly W or I; X209 is an aliphatic residue, particularly L; X215 is C; X223 is a constrained residue, particularly P; X269 is a constrained residue, particularly P; X273 is an aromatic residue, particularly Y; X282 is a polar residue, particularly S; and X284 is a non-polar residue, particularly G; X297 is a polar residue, particularly S; and X321 is a constrained residue, particularly P. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:82), with the proviso that the engineered transaminase polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:82

In some embodiments, the engineered transaminase comprises an amino acid sequence that includes the following features: X8 is a constrained residue, particularly is P; X60 is an aromatic residue, particularly F; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X81 is a non-polar residue, particularly G; X94 is an aliphatic residue, particularly I or L; X96 is an aliphatic residue, particularly L; X122 is a constrained, non-polar or aliphatic residue, particularly M, I, L, V, or H; X124 is a polar or constrained residue, particularly T, H or N; X136 is an aromatic residue, particularly Y or F; X169 is an aliphatic residue, particularly L; X199 is an aliphatic or aromatic residue, particularly W or I; X209 is an aliphatic residue, particularly L; X215 is C; X217 is a polar residue, particularly N; X223 is a constrained residue, particularly P; X269 is a constrained residue, particularly P; X273 is an aromatic residue, particularly Y; X282 is a polar residue, particularly S; and X284 is a non-polar residue, particularly G; X297 is a polar residue, particularly S; and X321 is a constrained residue, particularly P. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:84, 86, 88, 96, 98, or 100), with the proviso that the engineered transaminase polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:84, 86, 88, 96, 98, or 100.

In some embodiments, the engineered transaminase comprises an amino acid sequence that includes the following features: X8 is a constrained residue, particularly is P; X60 is an aromatic residue, particularly F; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X81 is a non-polar residue, particularly G; X94 is an aliphatic residue, particularly I or L; X96 is an aliphatic residue, particularly L; X122 is a constrained, non-polar or aliphatic residue, particularly M, I, L, V, or H; X136 is an aromatic residue, particularly Y or F; X150 is aromatic, constrained or polar residue, particularly F, H, or S; X169 is an aliphatic residue, particularly L; X199 is an aliphatic or aromatic residue, particularly W or I; X209 is an aliphatic residue, particularly L; X215 is C; X217 is a polar residue, particularly N; X223 is a constrained residue, particularly P; X269 is a constrained residue, particularly P; X273 is an aromatic residue, particularly Y; X282 is a polar residue, particularly S; and X284 is a non-polar residue, particularly G; X297 is a polar residue, particularly S; and X321 is a constrained residue, particularly P. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:90), with the proviso that the engineered transaminase polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:90.

In some embodiments, the engineered transaminase comprises an amino acid sequence that includes the following features: X8 is a constrained residue, particularly is P; X60 is an aromatic residue, particularly F; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X81 is a non-polar residue, particularly G; X94 is an aliphatic residue, particularly I or L; X122 is a constrained, non-polar or aliphatic residue, particularly M, I, L, V, or H; X124 is a polar or constrained residue, particularly T, H or N; X136 is an aromatic residue, particularly Y or F; X150 is aromatic, constrained or polar residue, particularly F, H, or S; X152 is C or a non-polar, aliphatic, or polar residue, particularly G, I, L, S or C; X169 is an aliphatic residue, particularly L; X199 is an aliphatic or aromatic residue, particularly W or I; X209 is an aliphatic residue, particularly L; X215 is a C; X217 is a polar residue, particularly N; X223 is a constrained residue, particularly P; X269 is a constrained residue, particularly P; X273 is an aromatic residue, particularly Y; X282 is a polar residue, particularly S; and X284 is a non-polar residue, particularly G; X297 is a polar residue, particularly S; and X321 is a constrained residue, particularly P. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:92), with the proviso that the engineered transaminase polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:92.

In some embodiments, the engineered transaminase comprises an amino acid sequence that includes the following features: X8 is a constrained residue, particularly is P; X60 is an aromatic residue, particularly F; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X81 is a non-polar residue, particularly G; X94 is an aliphatic residue, particularly I or L; X96 is an aliphatic residue, particularly L; X122 is a constrained, non-polar or aliphatic residue, particularly M, I, L, V, or H; X124 is a polar or constrained residue, particularly T, H or N; X136 is an aromatic residue, particularly Y or F; X150 is aromatic, constrained or polar residue, particularly F, H, or S; X152 is C or a non-polar, aliphatic, or polar residue, particularly G, I, L, S or C; X169 is an aliphatic residue, particularly L; X199 is an aliphatic or aromatic residue, particularly W or I; X209 is an aliphatic residue, particularly L; X215 is a C; X217 is a polar residue, particularly N; X223 is a constrained residue, particularly P; X269 is a constrained residue, particularly P; X273 is an aromatic residue, particularly Y; X282 is a polar residue, particularly S; and X284 is a non-polar residue, particularly G; X297 is a polar residue, particularly S; and X321 is a constrained residue, particularly P. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO:94), with the proviso that the engineered transaminase polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO:94.

In some embodiments, the engineered transaminase comprises an amino acid sequence that includes the following features: X8 is a constrained residue, particularly is P; X60 is an aromatic residue, particularly F; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X81 is a non-polar residue, particularly G; X94 is an aliphatic residue, particularly I or L; X96 is an aliphatic residue, particularly L; X122 is a constrained, non-polar or aliphatic residue, particularly M, I, L, V, or H; X124 is a polar or constrained residue, particularly T, H or N; X136 is an aromatic residue, particularly Y or F; X169 is an aliphatic residue, particularly L; X199 is an aliphatic or aromatic residue, particularly W or I; X209 is an aliphatic residue, particularly L; X215 is C; X217 is a polar residue, particularly N; X223 is a constrained residue, particularly P; X269 is a constrained residue, particularly P; X273 is an aromatic residue, particularly Y; X282 is a polar residue, particularly S; and X284 is a non-polar residue, particularly G; X297 is a polar residue, particularly S; X321 is a constrained residue, particularly P; and X329 is a constrained or aromatic residue, particularly H. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO: 102), with the proviso that the engineered transaminase polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO: 102.

In some embodiments, the engineered transaminase comprises an amino acid sequence that includes the following features: X8 is a constrained residue, particularly is P; X60 is an aromatic residue, particularly F; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X81 is a non-polar residue, particularly G; X94 is an aliphatic residue, particularly I or L; X96 is an aliphatic residue, particularly L; X122 is a constrained, non-polar or aliphatic residue, particularly M, I, L, V, or H; X124 is a polar or constrained residue, particularly T, H or N; X136 is an aromatic residue, particularly Y or F; X150 is aromatic, constrained or polar residue, particularly S; X152 is cysteine (C), non-polar, aliphatic, or polar residue, particularly G, I, L, S or C; X169 is an aliphatic residue, particularly L; X199 is an aliphatic or aromatic residue, particularly W or I; X209 is an aliphatic residue, particularly L; X215 is C; X217 is a polar residue, particularly N; X223 is a constrained residue, particularly P; X269 is a constrained residue, particularly P; X273 is an aromatic residue, particularly Y; X282 is a polar residue, particularly S; X284 is a non-polar residue, particularly G; X297 is a polar residue, particularly S; and X321 is a constrained residue, particularly P. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO: 110), with the proviso that the engineered transaminase polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO: 110.

In some embodiments, the engineered transaminase comprises an amino acid sequence that includes the following features: X8 is a constrained residue, particularly is P; X49 is a polar residue, particularly T; X60 is an aromatic residue, particularly F; X61 is an aromatic residue, particularly Y; X62 is an aromatic or polar residue, particularly T, Y or F; X65 is an aliphatic residue, particularly A; X69 is C or a non-polar, aliphatic or polar residue, particularly G, C, T, A, or S; X81 is a non-polar residue, particularly G; X94 is an aliphatic residue, particularly I or L; X96 is an aliphatic residue, particularly L; X117 is a non-polar residue, particularly G; X122 is a constrained, non-polar or aliphatic residue, particularly M, I, L, V, or H; X124 is a polar or constrained residue, particularly T, H or N; X126 is a polar residue, particularly T; X136 is an aromatic residue, particularly Y or F; X150 is aromatic, constrained or polar residue, particularly S; X152 is cysteine (C), non-polar, aliphatic, or polar residue, particularly G, I, L, S or C; X169 is an aliphatic residue, particularly L; X199 is an aliphatic or aromatic residue, particularly W or I; X209 is an aliphatic residue, particularly L; X215 is C; X217 is a polar residue, particularly N; X223 is a constrained residue, particularly P; X269 is a constrained residue, particularly P; X273 is an aromatic residue, particularly Y; X282 is a polar residue, particularly S; X284 is a non-polar residue, particularly G; X297 is a polar residue, particularly S; X302 is an aliphatic residue, particularly A; and X321 is a constrained residue, particularly P. In some embodiments, the transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence based on SEQ ID NO:2 having the features described for preceding specified residue positions (e.g., SEQ ID NO: 166), with the proviso that the engineered transaminase polypeptide comprises an amino acid sequence that includes at least the features described for the specified residue positions. In some embodiments, the engineered transaminase polypeptide can comprise an amino acid sequence that is at least about 80%, 85%, 86%, 87%, 88%, 89%, 90%, 91%, 92%, 93%, 94%, 95%, 96%, 97%, 98%, 99% identical to a reference sequence of SEQ ID NO: 166.

Table 2 below provides exemplary engineered transaminase polypeptides, with each row listing two SEQ ID NOs, the odd number referring to the nucleotide sequence encoding the amino acid sequence provided by the even number. The residue differences are based on comparison to reference sequence of SEQ ID NO:2, a transaminase derived from *Arthrobacter* sp KNK168 and differs from the naturally occurring enzyme in having a substitution of isoleucine (I) at residue position X306 with valine (V). In the Activity column, the levels of increasing activity (i.e., "+" "++" "+++" etc.) were defined as follows: "+" indicates at least equal to but not greater than 2 times the activity of SEQ ID NO:4 (assay conditions: 2 g/L ketoamide substrate, 0.5 M isopropylamine, 22° C., pH 7.5, 5% DMSO, 100 μM PLP); "++" indicates about 50-to-100 times greater than the activity of SEQ ID NO:4 (assay conditions: 2 g/L ketoamide substrate, 0.5 M isopropylamine, 22° C., pH 7.5, 5% MeOH, 100 μM PLP); "+++" indicates about 1.1 to about 5 times greater than the activity of SEQ ID NO:22 (assay conditions: 5-10 g/L ketoamide substrate, 0.5-1 M isopropylamine, 22-30° C., pH 7.5, 5% MeOH, 100 μM PLP); "++++" indicates about 1.1 to 5 times greater than the activity of SEQ ID NO:48 (assay conditions: 10-40 g/L ketoamide substrate, 1 M isopropylamine, 30-45° C., pH 8.5, 10% MeOH, 100 μM PLP); "+++++" indicates about 1.1 to 5 times or greater than the activity of SEQ ID NO:58 (assay conditions: 40-100 g/L ketoamide substrate, 1 M isopropylamine, 45° C., pH 8.5, 10% MeOH-25% DMSO, 250 μM PLP); "++++++" indicates about 1.1 to 5 times or greater than the activity of SEQ ID NO: 104 (assay conditions: 40-100 g/L ketoamide substrate, 1 M isopropylamine, 45° C., pH 8.5, 50% DMSO, 1000 μM PLP). Exemplary assay conditions for measuring activity using methanol and DMSO are described in Examples 6-11.

TABLE 2

| SEQ ID NO | Residue differences relative to SEQ ID NO:2 | No. Residue Differences | Activity |
|---|---|---|---|
| 1/2 | — | — | -- |
| 3/4 | V69G; F122V; S223P; A284G | 4 | + |
| 5/6 | V65A; V69G; F122I; S223P | 4 | + |
| 7/8 | F122L; S223P; A284G | 3 | + |
| 9/10 | F122I; S223P; A284G | 3 | + |
| 11/12 | F122L; S174A; S223P; A284G | 4 | + |
| 13/14 | Y26H; V65A; V69G; F122I; S223P; A284G | 6 | + |
| 15/16 | Y26H; H62T; V65A; V69G; F122I; T178S; V199W; S223P; F225Y; T282S; A284G | 11 | ++ |
| 17/18 | Y26H; H62F; V65A; V69G; F122V; G136Y; V199I; A209L; S223P; F225Y; T282S; A284G | 12 | ++ |
| 19/20 | Y26H; H62T; V65A; V69G; F122V; G136Y; E137T; V199I; A209L; S223P; T282S; A284G | 12 | ++ |
| 21/22 | Y26H; H62T; V65A; V69G; F122I; G136Y; E137I; V199I; A209L; S223P; T282S; A284G | 12 | ++ |
| 23/24 | Y26H; H62T; V65A; V69G; F122I; G136Y; E137T; V199I; A209L; S223P; F225Y; T282S; A284G | 13 | ++ |
| 25/26 | Y26H; V65A; V69G; F122V; G136Y; E137I; S174A; V199I; A209L; S223P; 1230V; A284G | 12 | ++ |
| 27/28 | Y26H; H62T; V65A; V69G; F122H; G136Y; E137I; V199I; A209L; S223P; T282S; A284G | 12 | +++ |

TABLE 2-continued

| SEQ ID NO | Residue differences relative to SEQ ID NO:2 | No. Residue Differences | Activity |
|---|---|---|---|
| 29/30 | Y26H; H62T; V65A; V69T; F122I; G136Y; E137I; V199I; A209L; S223P; T282S; A284G | 12 | +++ |
| 31/32 | Y26H; H62T; V65A; V69C; F122I; G136Y; E137I; V199I; A209L; S223P; T282S; A284G | 12 | +++ |
| 33/34 | Y26H; H62T; V65A; V69A; F122I; G136Y; E137I; V199I; A209L; S223P; T282S; A284G | 12 | +++ |
| 35/36 | Y26H; L61Y; H62T; V65A; V69G; F122I; G136Y; E137I; V199I; A209L; S223P; T282S; A284G | 13 | +++ |
| 37/38 | Y26H; H62Y; V65A; V69G; F122I; G136Y; E137I; V199I; A209L; S223P; T282S; A284G | 12 | +++ |
| 39/40 | Y26H; H62T; V65A; V69G; F122I; G136F; E137I; V199I; A209L; S223P; T282S; A284G | 12 | +++ |
| 41/42 | S4Y; Y26H; H62T; V65A; V69G; M94I; F122I; G136Y; E137T; V199I; A209L; G215C; S223P; T282S; A284G | 15 | +++ |
| 43/44 | H62T; V65A; V69G; M94I; F122I; G136Y; E137I; V199I; A209L; G215C; S223P; T282S; A284G | 13 | +++ |
| 45/46 | H62T; V65A; V69G; M94I; F122I; G136Y; E137T; V199I; A209L; G215C; S223P; T282S; A284G | 13 | +++ |
| 47/48 | H62T; V65A; V69C; M94I; F122I; G136Y; E137T; V199I; A209L; G215C; S223P; T282S; A284G | 13 | +++ |
| 49/50 | S8P; H62T; V65A; V69C; M94I; F122I; G136Y; E137T; V199I; A209L; G215C; S223P; T282S; A284G | 14 | ++++ |
| 51/52 | L61Y; H62T; V65A; V69S; M94I; F122I; G136F; E137T; V152I; V199I; A209L; G215C; S223P; T282S; A284G | 15 | ++++ |
| 53/54 | L61Y; H62T; V65A; V69C; M94I; F122V; G136F; E137T; V199I; A209L; G215C; S223P; T282S; A284G | 14 | ++++ |
| 55/56 | L61Y; H62T; V65A; V69T; M94I; F122V; G136F; E137T; V199I; A209L; G215C; S223P; T282S; A284G | 14 | ++++ |
| 57/58 | L61Y; H62T; V65A; V69T; M94I; F122I; G136F; V199I; A209L; G215C; S223P; T282S; A284G | 13 | ++++ |
| 59/60 | L61Y; H62T; V65A; V69T; M94I; F122H; G136F; V199I; A209L; G215C; S223P; T282S; A284G | 13 | ++++ |
| 61/62 | L61Y; H62T; V65A; V69C; M94I; F122I; G136Y; E137T; F160L; A169L; V199I; A209L; G215C; S223P; L269P; T282S; A284G | 17 | ++++ |
| 63/64 | L61Y; H62T; V65A; V69C; M94L; F122I; G136Y; E137T; A169L; V199I; A209L; G215C; S223P; T282S; A284G; V306L | 16 | ++++ |
| 65/66 | L61Y; H62T; V65A; V69C; M94I; Q102L; F122I; G136F; Y150F; V152I; V199I; A209L; G215C; S223P; T282S; A284G | 16 | ++++ |
| 67/68 | S8P; P48A; L61Y; H62T; V65A; V69T; D81G; M94I; I96L; Q102K; F122I; G136F; I163V; V199I; A209L; L211I; G215C; G217N; S223P; L252F; L273Y; T282S; A284G; S321P | 24 | +++++ |
| 69/70 | S8P; P48A; L61Y; H62T; V65A; V69T; D81G; M94I; F122I; G136F; A169L; V199I; A209L; G215C; G217N; S223P; L269P; T282S; A284G; P297S; S321P | 21 | +++++ |
| 71/72 | S8P; L61Y; H62T; V65A; V69T; M94I; F122I; G136F; V199I; A209L; G215C; S223P; T282S; A284G | 14 | +++++ |
| 73/74 | S8P; L61Y; H62T; V65A; V69T; D81G; M94L; I96L; F122I; G136F; T178S; V199I; A209L; G215C; S223P; L269P; T282S; A284G; P297S; S321P | 20 | +++++ |
| 75/76 | S8P; Y60F; L61Y; H62T; V65A; V69T; D81G; M94I; I96L; F122I; G136F; V152L; T178S; V199I; A209L; G215C; G217N; S223P; L252F; L269P; L273Y; T282S; A284G; P297S; S321P | 25 | +++++ |
| 77/78 | S8P; Y60F; L61Y; H62T; V65A; V69T; D81G; M94L; I96L; F122I; G136F; A169L; T178S; V199I; A209L; G215C; G217N; S223P; L269P; T282S; A284G; S292T; P297S; S321P | 24 | +++++ |
| 79/80 | S8P; Y60F; L61Y; H62T; V65A; V69T; D81G; M94I; I96L; F122I; G136F; A169L; V199I; A209L; G215C; G217N; S223P; L269P; L273Y; T282S; A284G; P297S; S321P | 23 | +++++ |
| 81/82 | S8P; Y60F; L61Y; H62T; V65A; V69T; D81G; M94L; I96L; F122I; G136F; A169L; T178S; V199I; A209L; G215C; S223P; L269P; L273Y; T282S; A284G; P297S; S321P | 23 | +++++ |
| 83/84 | S8P; Y60F; L61Y; H62T; V65A; V69T; D81G; M94I; I96L; F122I; S124T; G136F; A169L; V199I; A209L; G215C; G217N; S223P; L269P; L273Y; T282S; A284G; P297S; S321P | 24 | +++++ |
| 85/86 | S8P; Y60F; L61Y; H62T; V65A; V69T; D81G; M94I; I96L; F122I; S124H; G136F; A169L; V199I; A209L; G215C; G217N; S223P; L269P; L273Y; T282S; A284G; P297S; S321P | 24 | +++++ |
| 87/88 | S8P; Y60F; L61Y; H62T; V65A; V69T; D81G; M94I; I96L; F122I; S124N; G136F; A169L; V199I; A209L; G215C; G217N; S223P; L269P; L273Y; T282S; A284G; P297S; S321P | 24 | +++++ |
| 89/90 | S8P; Y60F; L61Y; H62T; V65A; V69T; D81G; M94I; I96L; F122I; G136F; Y150H; A169L; V199I; A209L; G215C; G217N; S223P; L269P; L273Y; T282S; A284G; P297S; S321P | 24 | +++++ |

TABLE 2-continued

| SEQ ID NO | Residue differences relative to SEQ ID NO:2 | No. Residue Differences | Activity |
|---|---|---|---|
| 91/92 | S8P; Y60F; L61Y; H62T; V65A; V69T; D81G; M94I; I96L; F122M; S124H; G136F; Y150H; V152S; A169L; V199I; A209L; G215C; G217N; S223P; L269P; L273Y; T282S; A284G; P297S; S321P | 26 | +++++ |
| 93/94 | S8P; Y60F; L61Y; H62T; V65A; V69T; D81G; M94I; I96L; F122I; S124T; G136F; Y150S; V152C; A169L; V199I; A209L; G215C; G217N; S223P; L269P; L273Y; T282S; A284G; P297S; S321P | 26 | +++++ |
| 95/96 | S8P; Y60F; L61Y; H62T; V65A; V69T; D81G; M94I; I96L; F122M; S124N; G136F; A169L; V199I; A209L; G215C; G217N; S223P; L269P; L273Y; T282S; A284G; P297S; S321P | 24 | +++++ |
| 97/98 | S8P; Y60F; L61Y; H62T; V65A; V69T; D81G; M94I; I96L; F122I; S124H; G136F; A169L; V199I; A209L; G215C; G217N; S223P; L269P; L273Y; T282S; A284G; P297S; S321P | 24 | +++++ |
| 99/100 | S8P; Y60F; L61Y; H62T; V65A; V69T; D81G; M94I; I96L; F122M; S124N; G136F; A169L; V199I; A209L; G215C; G217N; S223P; L269P; L273Y; T282S; A284G; P297S; S321P | 24 | +++++ |
| 101/102 | S8P; Y60F; L61Y; H62T; V65A; V69T; D81G; M94I; I96L; F122M; S124N; G136F; A169L; V199I; A209L; G215C; G217N; S223P; L269P; L273Y; T282S; A284G; P297S; S321P; Q329H | 25 | +++++ |
| 103/104 | S8P; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 26 | +++++ |
| 105/106 | S8P; Y60F; L61Y; H62T; V65A; V69T; D81G; M94I; I96L; F122M; S124T; S126T; G136F; R138K; Y150S; V152G; Q155M; A169L; V199I; A209L; G215C; G217N; S223P; L269P; L273Y; T282S; A284G; P297S; S321P | 29 | +++++ |
| 107/108 | S8P; Y60F; L61Y; H62T; V65A; V69T; D81G; M94I; I96L; F122M; S124T; G136F; R138P; Q146R; Y150S; V152S; A169L; V199I; A209L; G215C; G217N; S223P; L269P; L273Y; T282S; A284G; P297S; S321P | 28 | +++++ |
| 109/110 | S8P; Y60F; L61Y; H62T; V65A; V69T; D81G; M94I; I96L; F122M; S124T; S126T; G136F; Y150S; V152C; A169L; V199I; A209L; G215C; G217N; S223P; L269P; L273Y; T282S; A284G; P297S; S321P | 27 | ++++++ |
| 111/112 | S8P; Y60F; L61Y; H62T; V65A; V69T; D81G; M94I; I96L; F122M; S124T; G136F; Y150S; V152C; I163H; A169L; /V199I; A209L; G215C; G217N; S223P; L269P; L273Y; T282S; A284G; P297S; S321P | 27 | ++++++ |
| 113/114 | S8P; Y60F; L61Y; H62T; V65A; V69T; D81G; M94I; I96L; F122M; S124T; G136F; Y148A; Y150S; V152C; A169L; V199I; A209L; G215C; G217N; S223P; L269P; L273Y; T282S; A284G; P297S; S321P | 27 | ++++++ |
| 115/116 | S8P; Y60F; L61Y; H62T; V65A; V69T; D81G; M94I; I96L; F122M; S124T; G136F; Y150S; V152C; W156Q; A169L; V199I; A209L; G215C; G217N; S223P; L269P; L273Y; T282S; A284G; P297S; S321P | 27 | ++++++ |
| 117/118 | S8P; Y60F; L61Y; H62T; V65A; V69T; D81G; M94I; I96L; F122M; S124T; G136F; Y150S; V152C; R164V; A169L; V199I; A209L; G215C; G217N; S223P; L269P; L273Y; T282S; A284G; P297S; S321P | 27 | ++++++ |
| 119/120 | S8P; Y60F; L61Y; H62T; V65A; V69T; D81G; M94I; I96L; F122M; S124T; G136F; Y148F; Y150S; V152C; A169L; V199I; A209L; G215C; G217N; S223P; L269P; L273Y; T282S; A284G; P297S; S321P | 27 | ++++++ |
| 121/122 | S8P; Y60F; L61Y; H62T; V65A; V69T; D81G; M94I; I96L; E120Y; F122M; S124T; G136F; Y150S; V152C; A169L; V199I; A209L; G215C; G217N; S223P; L269P; L273Y; T282S; A284G; P297S; S321P | 27 | ++++++ |
| 123/124 | S8P; Y60F; L61Y; H62T; V65A; V69T; D81G; M94I; I96L; F122M; S124T; G136F; Y150S; V152C; Q155V; A169L; V199I; A209L; G215C; G217N; S223P; L269P; L273Y; T282S; A284G; P297S; S321P | 27 | ++++++ |
| 125/126 | S8P; Y60F; L61Y; H62T; V65A; V69T; D81G; M94I; I96L; F122M; S124T; G136F; Y150S; V152C; R164P; A169L; V199I; A209L; G215C; G217N; S223P; L269P; L273Y; T282S; A284G; P297S; S321P | 27 | ++++++ |
| 127/128 | S8P; Y60F; L61Y; H62T; V65A; V69T; D81G; M94I; I96L; F122M; S124T; G136F; Y150S; V152C; Q155T; A169L; V199I; A209L; G215C; G217N; S223P; L269P; L273Y; T282S; A284G; P297S; S321P | 27 | ++++++ |

TABLE 2-continued

| SEQ ID NO | Residue differences relative to SEQ ID NO:2 | No. Residue Differences | Activity |
|---|---|---|---|
| 129/130 | S8P; E5OL; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 27 | ++++++ |
| 131/132 | S8P; L18I; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 27 | ++++++ |
| 133/134 | S8P; D25Q; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 27 | ++++++ |
| 135/136 | S8P; E42G; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 27 | ++++++ |
| 137/138 | S8P; P48D; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 27 | ++++++ |
| 139/140 | S8P; P30Q; Y60F; L61Y; H62T; V65A; V69T; D81G; M94I; I96L; F122M; S124T; G136F; Y150S; V152C; A169L; V199I; A209L; G215C; G217N ;S223P; L269P; L273Y; T282S; A284G; P297S; S321P | 27 | ++++++ |
| 141/142 | S8P; L28P; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 27 | ++++++ |
| 143/144 | S8P; I41H; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 27 | ++++++ |
| 145/146 | S8P; P30M; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 27 | ++++++ |
| 147/148 | S8P; S54H; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 27 | ++++++ |
| 149/150 | S8P; L18C; I55V; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 28 | ++++++ |
| 151/152 | S8P; P48G; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 27 | ++++++ |
| 153/154 | S8P; P48V; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 27 | ++++++ |
| 155/156 | S8P; I41S; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 27 | ++++++ |
| 157/158 | S8P; E27T; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 27 | ++++++ |
| 159/160 | S8P; S54P; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 27 | ++++++ |
| 161/162 | S8P; P48Q; Y60F; L61Y; H62T; V65A; V69T; D81G; M94I; I96L; F122M; S124T; G136F; Y150S; V152C; A169L; V199I; A209L; G215C; G217N; S223P; L269P; L273Y; T282S; A284G; P297S; S321P | 27 | ++++++ |
| 163/164 | ASK; S8P; Y60F; L61Y; H62T; V65A; V69T; D81G; M94I; I96L; F122M; S124T; S126T; G136F; Y150S; V152C; A169L; V199I; A209L; G215C; G217N; S223P; L269P; L273Y; T282S; A284G; P297S; S321P | 28 | ++++++ |
| 165/166 | S8P; S49T; Y60F; L61Y; H62T; V65A; V69T; D81G; M94I; I96L; El 17G; F122M; S124T; S126T G136F; Y150S; V152S; A169L; V199I; A209L; G215C; G217N; S223P; L269P; L273Y; T282S; A284G; P297S; V302A; S321P | 30 | ++++++ |

TABLE 2-continued

| SEQ ID NO | Residue differences relative to SEQ ID NO:2 | No. Residue Differences | Activity |
|---|---|---|---|
| 167/168 | S8P; S54P; Y60F; L61Y; H62T; V65A; V69T; D81G; M94I; I96L; F122M; S124T; S126T; G136F; Y150S; V152S; A169L; V199I; D204A; A209L; G215C; G217N; S223P; L269P; L273Y; T282S; A284G; P297S; S321P | 29 | ++++++ |

As noted above, in some embodiments, the improved transaminase polypeptide comprises an amino acid sequence that is at least about 80%, 85%, 86%, 87%, 88%, 89%, 90%, 91%, 92%, 93%, 94%, 95%, 96%, 97%, 98%, 99% or more identical to a reference sequence of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168. In some embodiments, the improved transaminase polypeptides can have 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences as compared to the transaminase represented by SEQ ID NO:2. In some embodiments, the number of residue differences can be 1, 2, 3, 4, 5, 6, 7, 8, 9, 10, 11, 12, 14, 15, 16, 18, 20, 22, 24, 26, 30, 35, 40, 45, 50, 55, or 60 differences as compared to SEQ ID NO:2.

In some embodiments, the improved transaminase polypeptide comprises an amino acid sequence that is at least about 80%, 85%, 86%, 87%, 88%, 89%, 90%, 91%, 92%, 93%, 94%, 95%, 96%, 97%, 98%, or 99% identical to a reference sequence based on SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168, with the proviso that the improved transaminase amino acid sequence comprises any one of the set of residue differences contained in any one of the polypeptide sequences listed in Table 2 as compared to SEQ ID NO:2. In some embodiments, the improved transaminase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other amino acid residue positions as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at other residue positions. In some embodiments, the residue differences at other residue positions comprise substitutions with conservative amino acid residues.

In some embodiments, the improved transaminase polypeptides capable of converting the ketoamide substrate, 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in the presence of an amino group donor to levels of product detectable by HPLC-UV at 210 nm comprises an amino acid sequence corresponding to the sequence of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

In some embodiments, the engineered transaminase polypeptide is capable of converting the ketoamide substrate to product with 50 to 100 times or greater activity than the polypeptide of SEQ ID NO:4. In some embodiments, the engineered transaminase polypeptide capable of converting the ketoamide substrate to product with 50 to 100 times or greater activity than the polypeptide of SEQ ID NO:4 comprises an amino acid sequence corresponding to SEQ ID NO: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

In some embodiments, the engineered transaminase polypeptide is capable of converting the ketoamide substrate to product with about 1.1 to 5 times or greater activity than the polypeptide of SEQ ID NO:22. In some embodiments, the engineered transaminase polypeptide capable of converting the ketoamide substrate to product with about 1.1 to 5 times or greater activity than the polypeptide of SEQ ID NO:22 comprises an amino acid sequence corresponding to the sequence of SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

In some embodiments, the engineered transaminase polypeptide is capable of converting the ketoamide substrate to product with about 1.1-to-5-times or greater activity than the polypeptide of SEQ ID NO:48. In some embodiments, the engineered transaminase polypeptide capable of converting the ketoamide substrate to product with about 1.1-to-5-times or greater activity than the polypeptide of SEQ ID NO:48 comprises a sequence corresponding to the sequence of SEQ ID NO: 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

In some embodiments, the engineered transaminase polypeptide is capable of converting the ketoamide substrate to product with about 1.1 to 5 times or greater activity than the polypeptide of SEQ ID NO:58. In some embodiments, the engineered transaminase polypeptide capable of converting the ketoamide substrate to product with about 1.1 to 5 times or greater activity than the polypeptide of SEQ ID NO:58 comprises an amino acid sequence corresponding to the sequence of SEQ ID NO: 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

As noted above, in some embodiments, the improved transaminase polypeptide is also capable of converting keto-amide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine with at least 70%, 80%, 85%, 90%, 91%, 92%, 93%, 94%, 95%, 96%, 97%, 98%, or 99% enantiomeric excess. Exemplary transaminase polypeptides with the specified levels of enantioselectivity can comprise an amino acid sequence corresponding to SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

In some embodiments, the improved engineered transaminase polypeptides can comprise deletions of the engineered transaminase polypeptides described herein. Thus, for each and every embodiment of the transaminase polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the transaminase polypeptides, as long as the functional activity of the transaminase activity is maintained. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 amino acid residues. In some embodiments, the number of deletions can be 1, 2, 3, 4, 5, 6, 7, 8, 9, 10, 11, 12, 14, 15, 16, 18, 20, 22, 24, 26, 30, 35, 40, 45, 50, 55, or 60 amino acids. In some embodiments, the deletions can comprise deletions of 1, 2, 3, 4, 5, 6, 7, 8, 9, 10, 11, 12, 13, 14, 15, 16, 18, 20, 22, 24, 26, 28, or 30 amino acid residues.

As described herein, the transaminase polypeptides of the disclosure can be in the form of fusion polypeptides in which the transaminase polypeptides are fused to other polypeptides, such as, by way of example and not limitation, antibody tags (e.g., myc epitope), purifications sequences (e.g., His tags for binding to metals), and cell localization signals (e.g., secretion signals). Thus, the transaminase polypeptides can be used with or without fusions to other polypeptides.

The polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereoisomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (Melle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (InAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutamic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisoleucine (hlle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, *CRC Practical Handbook of Biochemistry and Molecular Biology*, CRC Press, Boca Raton, FL, at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

As described above the various modifications introduced into the naturally occurring polypeptide to generate an engineered transaminase enzyme can be targeted to a specific property of the enzyme.

In another aspect, the present disclosure provides polynucleotides encoding the improved transaminase polypeptides. The polynucleotides may be operatively linked to one or more heterologous regulatory sequences that control gene expression to create a recombinant polynucleotide capable of expressing the transaminase polypeptide. Expression constructs containing a heterologous polynucleotide encoding the engineered transaminase can be introduced into appropriate host cells to express the corresponding transaminase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved transaminase polypeptides disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Table 2.

In some embodiments, the polynucleotides can be selected and/or engineered to comprise codons that are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. Since not all codons need to be replaced to optimize the codon usage of the transaminases (e.g., because the natural sequence can have preferred codons and because use of preferred codons may not be required for all amino acid residues), codon optimized polynucleotides encoding the transaminase polypeptides may contain preferred codons at about 40%, 50%, 60%, 70%, 80%, or greater than 90% of codon positions of the full length coding region.

In some embodiments, the polynucleotide encodes a transaminase polypeptide comprising an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:4, wherein the polypeptide is capable of converting the ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in the presence of an amino group donor with an activity that is improved as compared to the activity of the transaminase of SEQ ID NO:2 derived from *Arthrobacter* sp KNK168.

In some embodiments, the polynucleotide encodes a transaminase polypeptide comprising an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid sequence corresponding to SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, or 102, wherein the polypeptide has one or more improved properties in converting the ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in presence of an amino group donor. In some embodiments, the encoded transaminase polypeptide has an activity that is equal to or greater than the activity of the polypeptide of SEQ ID NO:4.

In some embodiments, the polynucleotide encodes a transaminase polypeptide comprising an amino acid sequence that is at least about 80%, 85%, 86%, 87%, 88%, 89%, 90%, 91%, 92%, 93%, 94%, 95%, 96%, 97%, 98%, or 99% identical to a reference sequence of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

In some embodiments, the polynucleotide encodes a transaminase polypeptide comprising an amino acid sequence that is at least about 80%, 85%, 86%, 87%, 88%, 89%, 90%, 91%, 92%, 93%, 94%, 95%, 96%, 97%, 98%, or 99% identical to a reference sequence based on SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168, with the proviso that the improved transaminase amino acid sequence comprises any one of the set of residue differences contained in any one of the polypeptide sequences listed in Table 2 as compared to SEQ ID NO:2.

In some embodiments, the polynucleotides encoding the improved transaminase polypeptides are selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, or 167.

In some embodiments, the polynucleotides are capable of hybridizing under highly stringent conditions to a polynucleotide comprising SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, or 167, or a complement thereof, where the highly stringently hybridizing polynucleotides encode a transaminase polypeptide capable of converting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in presence of an amino group donor with an activity that is equal to or greater than the polypeptide of SEQ ID NO:4.

In some embodiments, the polynucleotides encode the polypeptides described herein but have about 80% or more sequence identity, about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered transaminase described herein. In some embodiments, the reference polynucleotide is selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, or 167.

An isolated polynucleotide encoding an improved transaminase polypeptide may be manipulated in a variety of ways to provide for expression of the polypeptide. In some embodiments, the polynucleotides encoding the engineered transaminase polypeptides can be provided as expression vectors where one or more control sequences is present to regulate the expression of the polynucleotides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2006.

In some embodiments, the control sequences include among others, promoters, leader sequence, polyadenylation sequence, propeptide sequence, signal peptide sequence, and transcription terminator. For bacterial host cells, suitable promoters for directing transcription of the nucleic acid constructs of the present disclosure, include the promoters obtained from the *E. coli* lac operon, *E. coli* trp operon, bacteriophage A, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proc. Natl Acad. Sci. USA 75: 3727-3731), as well as the tac promoter (DeBoer et al., 1983, Proc. Natl Acad. Sci. USA 80: 21-25).

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (see e.g., WO 96/00787, which is hereby incorporated by reference herein), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, Mol Cell Bio 15:5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence.

The foreign signal peptide coding region may be required where the coding sequence does not naturally contain a signal peptide coding region.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiol Rev 57: 109-137.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (see e.g., WO 95/33836, which is hereby incorporated by reference herein).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the transaminase polypeptide of the present invention would be operably linked with the regulatory sequence.

Thus, in another embodiment, the present disclosure is also directed to a recombinant expression vector comprising a polynucleotide encoding an engineered transaminase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or vims), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus.*

The expression vectors for expressing the transaminases can contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori, or the origins of replication of plasmids pBR322, pUC19, pACYC177 (which plasmid has the P15A ori), or pACYC184 permitting replication in *E. coli*, and pUB110, pE194, pTA1060, or pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, Proc Natl Acad Sci. USA 75:1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present invention are commercially available.

Suitable commercial expression vectors include p3×FLAGTMTM expression vectors from Sigma-Aldrich Chemicals, St. Louis MO, which includes a CMV promoter and hGH polyadenylation site for expression in mammalian host cells and a pBR322 origin of replication and ampicillin resistance markers for amplification in *E. coli*. Other suitable expression vectors are pBluescriptll SK(−) and pBK-CMV, which are commercially available from Stratagene, LaJolla CA, and plasmids which are derived from pBR322 (Gibco BRL), pUC (Gibco BRL), pREP4, pCEP4 (Invitrogen) or pPoly (Lathe et al., 1987, Gene 57:193-201).

In another aspect, the present disclosure provides a host cell comprising a polynucleotide encoding an improved transaminase polypeptide of the present disclosure, the polynucleotide being operatively linked to one or more control sequences for expression of the transaminase enzyme in the host cell. Host cells for use in expressing the transaminase polypeptides encoded by the expression vectors of the present invention are well known in the art and include but are not limited to, bacterial cells, such as *E. coli, Lactobacillus, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the transaminase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

An exemplary host cell is *Escherichia coli* W3110. The expression vector was created by operatively linking a polynucleotide encoding an improved transaminase into the plasmid pCK110900 operatively linked to the lac promoter under control of the lacI repressor. The expression vector also contained the PI5a origin of replication and the chloramphenicol resistance gene. Cells containing the subject polynucleotide in *Escherichia coli* W3110 were isolated by subjecting the cells to chloramphenicol selection.

The improved transaminases and polynucleotides encoding such polypeptides can be prepared using methods commonly used by those skilled in the art. As noted above, the naturally-occurring amino acid sequence and corresponding polynucleotide encoding the wild type transaminase enzyme of *Arthrobacter* sp KNK168, from which the parent sequence SEQ ID NO:2 was derived, is available in U.S. Pat. No. 7,169,592, which is hereby incorporated by reference herein. In some embodiments, the parent polynucleotide sequence is codon optimized to enhance expression of the transaminase in a specified host cell. The polynucleotide sequence designated SEQ ID NO: 1 was the parent sequence utilized as the starting point for most experiments and library construction of engineered transaminases.

The engineered transaminases can be obtained by subjecting the polynucleotide encoding the naturally occurring transaminase to mutagenesis and/or directed evolution methods. An exemplary directed evolution technique is mutagenesis and/or DNA shuffling as described in Stemmer, 1994, Proc Natl Acad Sci USA 91:10747-10751; WO 95/22625; WO 97/0078; WO 97/35966; WO 98/27230; WO 00/42651; WO 01/75767 and U.S. Pat. No. 6,537,746 (each of which is hereby incorporated by reference herein).

Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc Natl Acad Sci USA 93:3525-3529). Mutagenesis and directed evolution techniques useful for the purposes herein are also described in the following references: Ling, et al., 1997, "Approaches to DNA mutagenesis: an overview," Anal. Biochem. 254(2): 157-78; Dale et al., 1996, "Oligonucleotide-directed random mutagenesis using the phosphorothioate method," Methods Mol. Biol. 57:369-74; Smith, 1985, "In vitro mutagenesis," Ann. Rev. Genet. 19:423-462; Botstein et al., 1985, "Strategies and applications of in vitro mutagenesis," Science 229:1193-1201; Carter, 1986, "Site-directed mutagenesis," Biochem. J. 237: 1-7; Kramer et al., 1984, "Point Mismatch Repair," Cell 38:879-887; Wells et al., 1985, "Cassette mutagenesis: an efficient method for generation of multiple mutations at defined sites," Gene 34:315-323; Minshull et al., 1999, "Protein evolution by molecular breeding," Curr Opin Chem Biol 3:284-290; Christians et al., 1999, "Directed evolution of thymidine kinase for AZT phosphorylation using DNA family shuffling," Nature Biotech 17:259-264; Crameri et al., 1998, "DNA shuffling of a family of genes from diverse species accelerates directed evolution," Nature 391:288-291; Crameri et al., 1997, "Molecular evolution of an arsenate detoxification pathway by DNA shuffling," Nature Biotech 15:436-438; Zhang et al., 1997, "Directed evolution of an effective fmctosidase from a galactosidase by DNA shuffling and screening," Proc Natl Acad Sci USA 94:45-4-4509; Crameri et al., 1996, "Improved green fluorescent protein by molecular evolution using DNA shuffling,' Nature Biotech 14:315-319; and Stemmer, 1994, "Rapid evolution of a protein in vitro by DNA shuffling," Nature 370:389-391. All publications are incorporated herein by reference.

In some embodiments, the clones obtained following mutagenesis treatment are screened for transaminases having a desired improved enzyme property. Measuring transaminase enzyme activity from the expression libraries can be performed using the standard techniques, such as separation of the product (e.g., by HPLC) and detection of the product by measuring UV absorbance of the separated substrate and products and/or by detection using tandem mass spectroscopy (e.g., MS/MS). Exemplary assays are described in Example 4 below. The rate of increase in desired product per unit time indicates the relative (enzymatic) activity of the transaminase polypeptide in a fixed amount of the lysate (or a lyophilized powder made therefrom). Where the improved enzyme property desired is thermal stability, enzyme activity may be measured after subjecting the enzyme preparations to a defined temperature and measuring the amount of enzyme activity remaining after heat treatments. Clones containing a polynucleotide encoding the desired transaminases are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides of the invention can be prepared by chemical synthesis using, e.g., the classical phosphoramidite method described by Beaucage et al., 1981, Tet Lett 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, The Great American Gene Company, Ramona, CA, ExpressGen Inc. Chicago, IL, Operon Technologies Inc., Alameda, CA, and many others.

The engineered transaminase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*., are commercially available under the trade name CelLytic BTM from Sigma-Aldrich of St. Louis MO Chromatographic techniques for isolation of the transaminase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art. In some embodiments, the engineered transaminases can be expressed as fusion proteins with purification tags, such as His-tags having affinity for metals, or antibody tags for binding to antibodies, e.g., myc epitope tag.

In some embodiments, affinity techniques may be used to isolate the improved transaminase enzymes. For affinity chromatography purification, any antibody which specifically binds the transaminase polypeptide may be used. For the production of antibodies, various host animals, including but not limited to rabbits, mice, rats, etc., may be immunized by injection with an engineered polypeptide. The polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

In a further aspect, the improved transaminase polypeptides described herein can be used in a process for transamination of certain amino group acceptors (e.g., a ketone acceptor) in presence of an amino group donor. For the description of the compounds herein, the following meanings shall apply.

"Alkyl" is intended to include alkyl groups of the designated length in either a straight or branched configuration. Exemplary of such alkyl groups are methyl, ethyl, propyl, isopropyl, butyl, sec-butyl, tert-butyl, pentyl, isopentyl, hexyl, isohexyl, and the like. The alkyl groups are unsubstituted or substituted with one to three groups independently selected from the group consisting of halogen, hydroxy, carboxy, aminocarbonyl, amino, $C_{1-4}$alkoxy, and $C_{1-4}$ alkylthio.

"Cycloalkyl" is intended to mean cyclic rings of alkanes of five to twelve total carbon atoms, or any number within this range (i.e., cyclopentyl, cyclohexyl, cycloheptyl, etc).

"Halogen" is intended to include the halogen atoms fluorine, chlorine, bromine, and iodine.

"Aryl" is intended to mean an aromatic group, including phenyl and naphthyl. "Aryl" is unsubstituted or substituted with one to five substituents independently selected from fluoro, hydroxy, trifluoromethyl, amino, $C_{1-4}$ alkyl, and $C_{1-4}$ alkoxy.

"Heteroaryl" means an 5- or 6-membered aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include, but are not limited to, pyrrolyl, isoxazolyl, isothiazolyl, pyrazolyl, pyridinyl, oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, and dibenzofuranyl. "Heteroaryl" is unsubstituted or substituted with one to five substituents independently selected from fluoro, hydroxy, trifluoromethyl, amino, $C_{1-4}$ alkyl, and CM alkoxy.

In some embodiments, the transaminases can be used in a process for preparing a compound of structural formula (I):

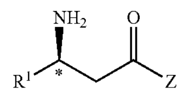

having the indicated stereochemical configuration at the stereogenic center marked with an *; in an enantiomeric excess of at least 70% over the opposite enantiomer, wherein Z is $OR^2$ or $NR^2R^3$;

$R^1$ is $C_{1-8}$ alkyl, aryl, heteroaryl, aryl-$C_{1-2}$ alkyl, or heteroaryl-$C_{1-2}$ alkyl;

$R^2$ and $R^3$ are each independently hydrogen, $C_{1-8}$ alkyl, aryl, or aryl-$C_{1-2}$ alkyl; or $R^2$ and $R^3$ together with the nitrogen atom to which they are attached form a 4- to 7-membered heterocyclic ring system optionally containing an additional heteroatom selected from O, S, NH, and $NC_{0-4}$ alkyl, the heterocyclic ring being unsubstituted or substituted with one to three substituents independently selected from oxo, hydroxy, halogen, $C_{1-4}$ alkoxy, and $C_{1-4}$ alkyl, wherein alkyl and alkoxy are unsubstituted or substituted with one to five fluorines; and the heterocyclic ring system being optionally fused with a 5- to 6-membered saturated or aromatic carbocyclic ring system or a 5- to 6-membered saturated or aromatic heterocyclic ring system containing one to two heteroatoms selected from O, S, and $NC_{0-4}$ alkyl, the fused ring system being unsubstituted or substituted with one to two substituents selected from hydroxy, amino, fluorine, $C_{1-4}$ alkyl, $C_{1-4}$ alkoxy, and trifluoromethyl. In these embodiments, the process comprises the step of contacting a prochiral ketone of structural formula (II):

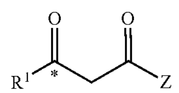

with an improved transaminase polypeptide disclosed herein in the presence of an amino group donor in a suitable organic solvent under suitable reaction conditions for the conversion of the compound of formula (II) to the compound of formula (I).

In some embodiments of the process, the $R^1$ of formula (II) is benzyl, wherein the phenyl group of benzyl is unsubstituted or substituted with one to three substituents selected from the group consisting of fluorine, trifluoromethyl, and trifluoromethoxy.

In some embodiments of the process, the Z of formula (II) is $NR^2R^3$.

In some embodiments of the process, the $NR^2R^3$ of formula (II) is a heterocycle of the structural formula (III):

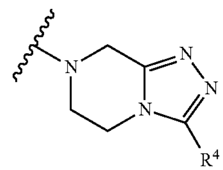

wherein $R^4$ is hydrogen or $C_{1-4}$ alkyl which is unsubstituted or substituted with one to five fluorines.

In some embodiments, the transaminases can be used in a process for preparing a compound of structural formula (1):

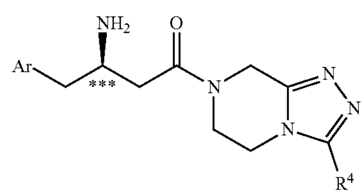

having the (R)-configuration at the stereogenic center marked with an ***, in an enantiomeric excess of at least 70% over the enantiomer having the opposite (S)-configuration; wherein Ar is phenyl which is unsubstituted or substituted with one to five substituents independently selected from the group consisting of fluorine, trifluoromethyl, and trifluoromethoxy; and $R^4$ is hydrogen or $C_{1-4}$ alkyl unsubstituted or substituted with one to five fluorines. In such embodiments, the process comprises the step of contacting a prochiral ketone of structural formula (2):

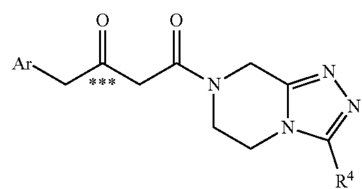

with an improved transaminase polypeptide disclosed herein in the presence of an amino group donor in a suitable organic solvent under suitable reaction conditions for the conversion of the compound of formula (2) to the compound of formula (1).

In some embodiments of the process, the Ar of formula (2) is 2,5-difluorophenyl or 2,4,5-trifluorophenyl, and $R^4$ is trifluoromethyl.

In some embodiments of the process, the Ar of formula (2) is 2,4,5-trifluorophenyl.

In some embodiments, the transaminases can be used in a process for preparing a compound of formula (1a), (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine, in enantiomeric excess:

(Ia)

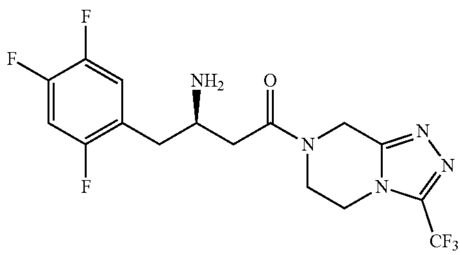

In these embodiments, the process comprises the step of contacting a prochiral ketone of structural formula (2a), 4-oxo-4-[3-(trifluoromethyl)-5,6-dihydro[1,2,4]triazolo[4,3-a]pyrazin-7(8H)-yl]-1-(2,4,5-trifluorophenyl)butan-2-one):

(2a)

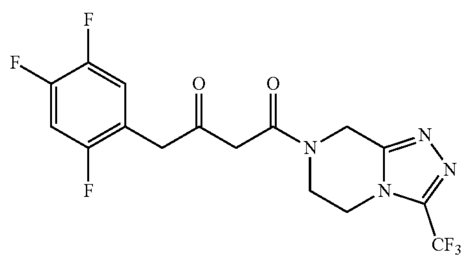

with an improved transaminase polypeptide disclosed herein in the presence of an amino group donor in a suitable organic solvent under suitable reaction conditions for the conversion of the compound of formula (2a) to the compound of formula (1a).

In some embodiments of the processes above, the compound of formula (I), the compound of formula (1) or the compound of formula (1a) is produced in at least 70%, 80%, 90%, 91%, 92%, 93%, 94%, 95%, 96%, 97%, 98%, 99% or more enantiomeric excess.

In some embodiments of the processes, the compound of formula (I), the compound of formula (1) or the compound of formula (1a) is produced in at least 99% enantiomeric excess.

In some embodiments of the process, the improved transaminases are selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

The compound of formula (II), the compound of formula (2), and the compound of formula (2a), along with their synthesis, are described in, among others, U.S. Pat. Nos. 7,326,708 and 7,468,459, the disclosures of which are incorporated herein by reference in their entirety.

As noted above, the transaminase polypeptide herein uses pyridoxal phosphate (PLP) as a coenzyme, which may be bound to the enzyme when prepared, e.g., as provided by the host cell in which the polypeptide is expressed. In some embodiments, PLP, PLP analogs, or precursors to PLP can be added to the media of host cells during expression of the transaminase polypeptide. In some embodiments of the processes, PLP or PLP analogs can be added to a reaction to provide the coenzyme required for enzyme activity. The amount of PLP sufficient for enzyme activity can be determined by one of skill in the art.

In some embodiments, the process comprises contacting or incubating the ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one with an improved transaminase in presence of an amino group donor under suitable reaction conditions to convert the ketoamide substrate to the product (2R)-4-oxo-4-[3-(trifluoromethyl)-5,6-dihydro[1,2,4]triazolo[4,3-a]pyraxin-7(8H)-yl]-1-(2,4,5-trifluorophenyl)butan-2-amine with 50 to 100 times or greater conversion rate and/or activity than that of SEQ ID NO:4.

Exemplary polypeptides comprise an amino acid sequence corresponding to SEQ ID NO: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

In some embodiments, the process comprises contacting or incubating the ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one with an improved transaminase in presence of an amino group donor under suitable reaction conditions to convert the ketoamide substrate to the product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine with 1.1 to 5 times or greater conversion rate and/or activity than that of SEQ ID NO:22.

Exemplary polypeptides comprise an amino acid sequence corresponding to SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

In some embodiments, the process comprises contacting or incubating the ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one with an improved transaminase in presence of an amino group donor under suitable reaction conditions to convert the ketoamide substrate to the product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine with 1.1 to 5 times or greater conversion rate and/or activity than that of SEQ ID NO:48.

Exemplary polypeptides comprise an amino acid sequence corresponding to SEQ ID NO: 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

In some embodiments, the process comprises contacting or incubating the ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one with an improved transaminase in presence of an amino group donor under suitable reaction conditions to convert the ketoamide substrate to the product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine with 1.1 to 5 times or greater conversion rate and/or activity than that of SEQ ID NO:58. Exemplary polypeptides comprise an amino acid sequence corresponding to SEQ ID NO: 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

In some embodiments of the processes above, the reaction condition for carrying out the process can comprise a pH of about 7.0 to about 9.0. In some embodiments, the reaction condition for the process is a pH of about 8.5.

In some embodiments, the reaction condition for carrying out the process can comprise a temperature of about 25° C. to about 50° C. In some embodiments, the reaction condition is a temperature of about 45° C.

In some embodiments, the reaction condition is a pH of about 8.5 and a temperature of about 45° C.

In some embodiments of the process, the organic solvent comprises a polar solvent, such as methanol or DMSO.

In some embodiments, the organic solvent is DMSO, which can be present from about 10% to about 40% volume/volume (v/v); about 25% to about 40% (v/v); 10% to about 50% (v/v) or about 25% to about 50% (v/v) of DMSO. In some embodiments, the DMSO is present at about 30% v/v, 35% v/v, 40% v/v, 45% v/v or about 50% v/v.

As discussed above, the amino group donor used in the process can be a chiral amine or an achiral amine. An achiral amino group donor has the advantage of not being limited in its reaction to a specific stereoisomer, thus requiring less of the amino group donor. Various suitable amino group donors can be used, including, by way of example and not limitation, isopropylamine (also referred to as 2-aminopropane), L, D or DL alanine, phenylalanine, glutamate, glutamine, leucine (or any other suitable α-amino acids), 3-aminobutyric acid (or any other suitable β-amino acids), and methylbenzylamine. In some embodiments, the amino group donor is isopropylamine. In some embodiments, other amino group donors may be used, including, among others, α-phenethylamine (also termed 1-phenylethanamine), and its enantiomers (S)-1-phenylethanamine and (R)-1-phenylethanamine, 2-amino-4-phenylbutane, glycine, L-glutamic acid, L-glutamate, monosodium glutamate, L-aspartic acid, L-lysine, L-ornithine, β-alanine, taurine, n-octylamine, cyclohexylamine, 1,4-butanediamine, 1,6-hexanediamine, 6-aminohexanoic acid, 4-aminobutyric acid, tyramine, and benzyl amine, 2-aminobutane, 2-amino-1-butanol, 1-amino-1-phenylethane, 1-amino-1-(2-methoxy-5-fluorophenyl)ethane, 1-amino-1-phenylpropane, 1-amino-1-(4-hydroxyphenyl)propane, 1-amino-1-(4-bromophenyl)propane, 1-amino-1-(4-nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-2-methylcyclopentane, 1-amino-3-methylcyclopentane, 1-amino-2-methylcyclohexane, 1-amino-1-(2-naphthyl)ethane, 3-methylcyclopentylamine, 2-methylcyclopentylamine, 2-ethylcyclopentylamine, 2-methylcyclohexylamine, 3-methylcyclohexylamine, 1-aminotetralin, 2-aminotetralin, 2-amino-5-methoxytetralin, and 1-aminoindan, including both (R) and (S) single isomers where possible and including all possible salts of the amines.

In some embodiments of the processes above, the step in the process can further comprise removal of the carbonyl by-product formed from the amino group donor when the amino group is transferred to the amino group acceptor. Such removal in situ can reduce the rate of the reverse reaction such that the forward reaction dominates and more substrate is then converted to product.

Removal of the carbonyl by-product can be carried in a number of ways. Where the amino group donor is an amino acid, such as alanine, the carbonyl by product, a keto acid, can be removed by reaction with a peroxide (see, e.g., US 2008/0213845, incorporated herein by reference). Peroxides which can be used include, among others, hydrogen peroxide; peroxyacids (peracids) such as peracetic acid ($CH_3CO_3H$), trifluoroperacetic acid and metachloroperoxybenzoic acid; organic peroxides such as t-butyl peroxide ($(CH_3)_3COOH$), or other selective oxidants such as tetrapropylammonium perruthenate, $MnO_2$, $KMnO_4$, ruthenium tetroxide and related compounds. Alternatively, pyruvate removal can be achieved via its reduction to lactate by employing lactate dehydrogenase to shift equilibrium to the product amine (see, e.g., Koszelewski et al., 2008, Adv. Syn. Catal. 350: 2761-2766). Pyruvate removal can also be achieved via its decarboxylation to carbon dioxide acetaldehyde by employing pyruvate decarboxylase (see, e.g., Höhne et al., 2008, Chem BioChem 9: 363-365).

In some embodiments, where the choice of the amino group donor results in a carbonyl by-product that has a vapor pressure higher than water (e.g., a low boiling co-product such as a volatile organic carbonyl compound), the carbonyl by-product can be removed by sparging the reaction solution with a non-reactive gas or by applying a vacuum to lower the reaction pressure and removing the carbonyl by-product present in the gas phase. A non-reactive gas is any gas that does not react with the reaction components. Various non-reactive gases include nitrogen and noble gases (e.g., inert gases). In some embodiments, the non-reactive gas is nitrogen gas.

In some embodiments, the amino acid donor used in the process is isopropylamine, which forms the carbonyl by-product acetone upon transfer of the amino group to the amino group acceptor. The acetone can be removed by sparging with nitrogen gas or applying a vacuum to the reaction solution and removing the acetone from the gas phase by an acetone trap, such as a condenser or other cold trap. Alternatively, the acetone can be removed by reduction to isopropanol using a ketoreductase.

In some embodiments of the processes above where the carbonyl by-product is removed, the corresponding amino group donor can be added during the transamination reaction to replenish the amino group donor and/or maintain the pH of the reaction. Replenishing the amino group donor also shifts the equilibrium towards product formation, thereby increasing the conversion of substrate to product. Thus, in some embodiments wherein the amino group donor is isopropylamine and the acetone product is removed in situ, isopropylamine can be added to the solution to replenish the amino group donor lost during the acetone removal and to maintain the pH of the reaction (e.g., at about 8.5). Alternatively, in embodiments where an amino acid is used as amino group donor, the keto acid carbonyl by-product can be recycled back to the amino acid by reaction with ammonia and NADH using an appropriate amino acid dehydrogenase enzyme, thereby replenishing the amino group donor.

In some embodiments, the process for converting ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine comprises contacting the ketoamide substrate at about 10 to 50 g/L with about 1 to 20 g/L of a transaminase described herein under reaction conditions of pH 7.5 to 9.0 and a temperature of 30 to 50° C. in presence of isopropylamine of from about 1 M to about 2 M, wherein at least 80%, 85%, 90%, 92%, 94%, 96%, or 98% or more of the ketoamide substrate is converted to product in 24 hrs. In some embodiments, the transaminase polypeptide capable of carrying out the foregoing reaction comprises an amino acid sequence corresponding to SEQ ID NO: 80, 86, 96, 98, 100, 102, 110, or 166.

In some embodiments, the processes above can further comprise the step of isolating the compound of structural formula (I), the compound of structural formula (1), or the compound of structural formula (1a) from the reaction solvent.

In some embodiments, the processes above can further comprise a step of converting the compound of structural formula (1) or the compound of structural formula (1a) into a pharmaceutically acceptable salt by contacting the compound with a pharmaceutically acceptable acid in a suitable reaction solvent. In some embodiments, the pharmaceutically acceptable acid is phosphoric acid and the pharmaceutically acceptable salt is the dihydrogenphosphate salt. In some embodiments, the salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine is the phosphate monohydrate salt, having the following chemical formula:

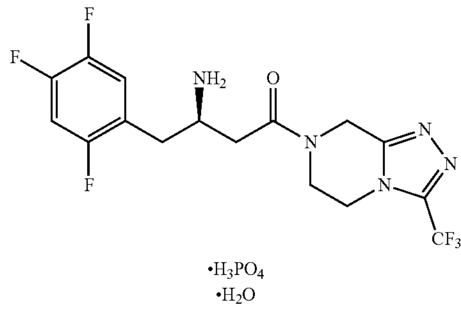 [SMILES: N[C@@H](CC(=O)N1CCn2c(nnc2C(F)(F)F)C1)Cc1cc(F)c(F)cc1F]

In some embodiments, in a process for the preparation of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate (1:1) monohydrate, the improvement in the process comprises a step of converting the compound of formula (1a) to the compound of formula (2a) with a transaminase polypeptide of the disclosure in presence of an amino group donor in a suitable organic solvent under suitable reaction conditions, wherein the compound of formula (1a) is (Ia)

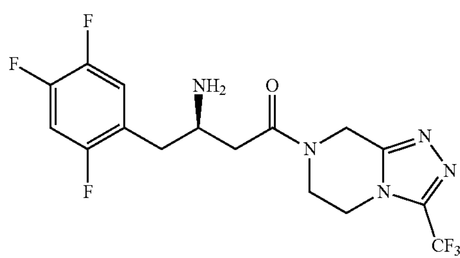

and the compound of formula (2a) is:

(2a)

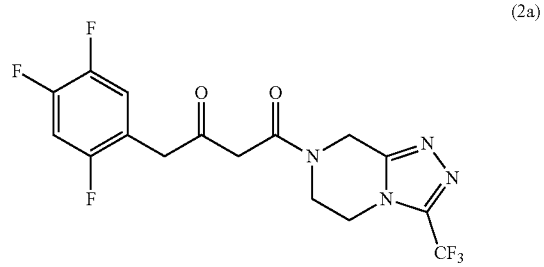 [SMILES: O=C(CC(=O)N1CCn2c(nnc2C(F)(F)F)C1)Cc1cc(F)c(F)cc1F]

In some embodiments of the preparation of the phosphate monohydrate salt, the amino donor is isopropylamine.

Methods for preparing various salts are described in U.S. Pat. Nos. 7,326,708 and 7,468,459, each of which is hereby incorporated by reference herein. An exemplary process for preparing the phosphate monohydrate of sitagliptin is presented in Example 13.

In some embodiments, the processes above can further comprise a step of crystallizing the pharmaceutically acceptable salt from the reaction solvent.

Also provided herein are compositions of the transaminases and substrates/products. In some embodiments, the compositions can comprise the compound of formula (I), the compound of formula (1) or the compound of formula (1a) and an improved transaminase of the disclosure. Any one or more of the improved engineered transaminases can be part of the composition.

In some embodiments, the composition can comprise the compound of formula (II), the compound of formula (2), or the compound of formula (2a) an improved transaminase described herein.

In some embodiments, the compositions can further comprise an amino group donor, e.g., of formula (3). In some embodiments of the compositions, the amino group donor can comprise isopropylamine, alanine, 3-aminobutyric acid, or methylbenzylamine. In some embodiments of the compositions, the amino group donor is an isopropylamine.

7. EXAMPLES

Various features and embodiments of the disclosure are illustrated in the following representative examples, which are intended to be illustrative, and not limiting.

Example 1: Wild-Type Transaminase Gene Acquisition and Construction of Expression Vectors Transaminase (TA) encoding genes were designed for expression in *E. coli.* based on the reported amino acid sequence of the transaminase, and a codon optimization algorithm as described in Example 1 of US application publication 20080248539, which is hereby incorporated by reference herein. Genes were synthesized using oligonucleotides, generally composed of 42 nucleotides, and the gene cloned into the expression vector pCK110700 (depicted as FIG. 1 in US application publication 20050153417, which is hereby incorporated by reference herein) or pCK110900 (depicted as FIG. 3 in US application publication 20060195947, which is hereby incorporated by reference herein) under the control of a lac promoter. This expression vector also contains the PI5a origin of replication and the chloramphenicol resistance gene. Resulting plasmids were transformed into *E. coli.* W3110 using standard methods.

Codon optimized genes and the encoded polypeptides are listed in Table 2, and their sequences provided as SEQ ID NOs: 1 and 2.

Likewise, the genes encoding the engineered transaminases of the present disclosure listed in Table 2 (SEQ ID NOs: 3-168) were cloned into vector pCK110700 or pCK110900 for expression in *E. coli* W3110.

Example 2: Production of Transaminase Powders—Shake Flask Procedure

A single microbial colony of *E. coli* containing a plasmid encoding a transaminase of interest was inoculated into 50 mL Luria Bertani broth containing 30 μg/mL chloramphenicol and 1% glucose. Cells were grown overnight (at least 16 hrs) in an incubator at 30° C. with shaking at 250 rpm. The culture was diluted into 250 mL M9YE (1.0 g/L ammonium chloride, 0.5 g/L of sodium chloride, 6.0 g/L of disodium monohydrogen phosphate, 3.0 g/L of potassium dihydrogen phosphate, 2.0 g/L of Tastone-154 yeast extract, 1 L/L de-ionized water) containing 30 μg/mL chloramphenicol and 100 μM pyridoxine, in a 1 liter flask to an optical density at 600 nm (OD600) of 0.2 and allowed to grow at 30° C. Expression of the transaminase gene was induced by addition of isopropyl β D-thiogalactoside (IPTG) to a final concentration of 1 mM when the OD600 of the culture is 0.6 to 0.8 and incubation was then continued overnight (at least 16 hrs). Cells were harvested by centrifugation (5000 rpm, 15 min, 4° C.) and the supernatant discarded. The cell pellet was resuspended with an equal volume of cold (4° C.) 100 mM triethanolamine (chloride) buffer, pH 7.5 containing 100 or 500 μM pyridoxal 5'-phosphate (PLP), and harvested by centrifugation as above. The washed cells were resuspended in two volumes of the cold triethanolamine (chloride) buffer containing PLP and passed through a French Press twice at 12,000 psi while maintained at 4° C. Cell debris was removed by centrifugation (9000 rpm, 45 min., 4° C.). The clear lysate supernatant was collected and stored at −20° C. Lyophilization of frozen clear lysate provides a dry powder of crude transaminase enzyme. Alternatively, the cell pellet (before or after washing) may be stored at 4° C. or 80° C.

Example 3: Production of Transaminase—Fermentation Procedure

A single microbial colony of *E. coli*. containing a plasmid with the transaminase gene of interest was inoculated into 2 mL M9YE broth (1.0 g/L ammonium chloride, 0.5 g/L of sodium chloride, 6.0 g/L of disodium monohydrogen phosphate, 3.0 g/L of potassium dihydrogen phosphate, 2.0 g/L of Tastone-154 yeast extract, 1 L/L de-ionized water) containing 30 μg/ml chloramphenicol and 1% glucose. Cells were grown overnight (at least 12 hrs) in an incubator at 37° C. with shaking at 250 rpm. After overnight growth, 0.5 mL of this culture was diluted into 250 ml M9YE Broth, containing 30 μg/ml chloramphenicol and 1% glucose in 1 liter flask and allowed to grow at 37° C. with shaking at 250 rpm. When the OD600 of the culture is 0.5 to 1.0, the cells were removed from the incubator and either used immediately, or stored at 4° C.

Bench-scale fermentations were carried out at 30° C. in an aerated, agitated 15 L fermentor using 6.0 L of growth medium (0.88 g/L ammonium sulfate, 0.98 g/L of sodium citrate; 12.5 g/L of dipotassium hydrogen phosphate trihydrate, 6.25 g/L of potassium dihydrogen phosphate, 3.3 g/L of Tastone-154 yeast extract, 0.083 g/L ferric ammonium citrate, and 8.3 ml/L of a trace element solution containing 2 g/L of calcium chloride dihydrate, 2.2 g/L of zinc sulfate heptahydrate, 0.5 g/L manganese sulfate monohydrate, 1 g/L cuprous sulfate heptahydrate, 0.1 g/L ammonium molybdate tetrahydrate and 0.02 g/L sodium tetraborate. The vessel was sterilized at 121° C. and 15 PSI for 30 minutes, and 100 μM pyridoxine was added post sterilization. The fermentor was inoculated with a late exponential culture of *E. coli* W3110 containing a plasmid encoding the transaminase gene of interest (grown in a shake flask as described above to a starting $OD_{600}$ of 0.5 to 1.0. The fermentor was agitated at 250-1250 rpm and air was supplied to the fermentation vessel at 0.6-25 L/min to maintain a dissolved oxygen level of 50% saturation or greater. The pH of the culture was maintained at 7.0 by addition of 20% v/v ammonium hydroxide. Growth of the culture was maintained by addition of a feed solution containing 500 g/L Cerelose dextrose, 12 g/L ammonium chloride and 5.1 g/L magnesium sulfate heptahydrate. After the culture reached an $OD_{600}$ of 70+−10, expression of transaminase was induced by addition of isopropyl-β-D-thiogalactoside (IPTG) to a final concentration of 1 mM and fermentation is continued for another 18 hours. The culture was then chilled to 4° C. and maintained at that temperature until harvested. Cells were collected by centrifugation at 5000 G for 40 minutes in a Sorval RC12BP centrifuge at 4° C. Harvested cells were used directly in the following downstream recovery process or they may be stored at 4° C. or frozen at −80° C. until such use.

The cell pellet was resuspended in 2 volumes of 100 mM triethanolamine (chloride) buffer, pH 7.5 containing 100 or 500 μM pyridoxal 5'-phosphate (PLP), at 4° C. to each volume of wet cell paste. The intracellular transaminase was released from the cells by passing the suspension through a homogenizer fitted with a two-stage homogenizing valve assembly using a pressure of 12000 psig. The cell homogenate was cooled to −20° C. immediately after disruption. A solution of 11% w/v polyethyleneimine pH 7.2 was added to the lysate to a final concentration of 0.5% w/v. A solution of 1 M $Na_2SO_4$ was added to the lysate to a final concentration of 100 mM. The lysate was then stirred for 30 minutes. The resulting suspension was clarified by centrifugation at 5000 G in a Sorval RC12BP centrifuge at 4° C. for 30 minutes. The clear supernatant was decanted and concentrated ten-fold using a cellulose ultrafiltration membrane with a molecular weight cut off of 30 kD. The final concentrate was dispensed into shallow containers, frozen at −20° C. and lyophilized to powder. The transaminase powder was stored at −80° C.

Example 4: High-Throughput Screening for Identification of Variants of the *Arthrobacter* sp. KNK168 Transaminase Capable of Stereoselectively Converting Ketoamide Substrate to Sitagliptin Achiral HPLC method to determine conversion of ketoamide substrate to sitagliptin: Enzymatic conversion of ketoamide substrate (prepared as described in U.S. Pat. No. 7,326,708) to sitagliptin was determined using an Agilent 1200 HPLC equipped with an Agilent Eclipse XDB-C8 column (4.6×150 mm, 5 μm), using 45:55 10 mM $NH_4Ac$/MeCN as eluent at a flow rate of 1.5 ml/min and a column temperature 40° C. Retention times: ketoamide substrate: 1.7 min; sitagliptin: 1.4 min. The ketoamide substrate and product in the eluant were determined as the peak area at 210 nm or 286 nm, with a path length of 1 cm. Using these conditions, the limit of detection for sitagliptin was 5 μg/mL.

Generally, an incident wavelength of 210 nm was used for activity measurements for transaminases with activity similar or equal to SEQ ID NO:4.

Chiral HPLC method to determine stereopurity of sitagliptin: Stereoisomeric purity of sitagliptin was determined using an Agilent 1200 HPLC equipped with a Daicel Chiralpak AD-H column (4.6×150 mm, 5 μm) using 60:40:0.1:0.1 EtOH/Heptane/diethylamine/water as the eluent at a flow rate of 0.8 ml/min and a column temperature of 35° C. Retention times: ketoamide substrate: 6.3 min; (S)-enantiomer: 8.4 min; sitagliptin: 10.8 min. The ketoamide substrate and product were determined as the peak area at 210 nm or 268 nm with a path length of 1 cm.

Liquid chromatography-mass spectroscopy (LC/MS) method for detecting low-level conversion of ketoamide substrate to sitagliptin: Low-level enzymatic conversion of ketoamide substrate to sitagliptin was determined using an LC/MS/MS method. Five microliters of sample was loaded into an Eclipse XDB-C8 HPLC column (4.6×150 mm) and eluted isocratically with a 40:60 mobile phase of 0.2% ammonium formate and methanol at 1.0 mL/min. The retention time of sitagliptin was 1.5 minutes at 35° C. Mass spectrometry was used for detection on a Waters Quattro triple quadruple. Q1 was set to pass the M+H ion at 408.1 AMU and Q3 was set to pass the 235.1 daughter ion. The collision cell (Q2) had a collision energy of 17.0 and Argon gas flow of 0.3 mL/min. Ionization was by APCI with a corona discharge of 5 μA, source temperature of 130° C. and probe temperature of 600° C. Desolvation gas flow was 100 L/minute and the cone gas was set to 50 L/minute. Using these conditions the limit of detection for sitagliptin was 71 μg/mL.

Example 5: High-Throughput Screening for Identification of Variants of the *Arthrobacter* sp. KNK168 Transaminase Capable of Stereoselectively Converting Ketoamide Substrate to Sitagliptin The gene encoding transaminase, constructed as described in Example 1, was mutagenized using methods described above and the population of altered DNA molecules was used to transform a suitable *E. coli* host strain. Antibiotic resistant transformants were selected and processed to identify those expressing a transaminase with an improved ability to transaminate the ketoamide substrate stereoselectively to sitagliptin in the presence of a suitable amino group donor (i.e., isopropylamine). Cell selection, growth, induced expression of transaminase variant enzymes and collection of cell pellets were as described below.

Recombinant *E. coli* colonies carrying a gene encoding transaminase were picked using a Q-Bot® robotic colony picker (Genetix USA, Inc., Boston, MA) into 96-well shallow well microtiter plates containing in each well 180 μL LB Broth, 1% glucose and 30 μg/mL chloramphenicol (CAM). Cells were grown overnight at 30° C. with shaking at 200 rpm. A 10 μL aliquot of this culture was then transferred into 96-deep well plates containing 390 μL M9YE broth, 100 μM pyridoxine and 30 μg/mL CAM. After incubation of the deep-well plates at 30° C. with shaking at 250 rpm for 2-3 hrs, recombinant gene expression within the cultured cells was induced by addition of IPTG to a final concentration of 1 mM. The plates were then incubated at 30° C. with shaking at 250 rpm for 18 hrs.

Cells were pelleted by centrifugation (4000 RPM, 10 min, 4° C.), resuspended in 200 μL lysis buffer and lysed by shaking at room temperature for 2 hours. The lysis buffer contained 100 mM triethanolamine (chloride) buffer, pH 7.5 or 8.5, 1 mg/mL lysozyme, 500 μg/mL polymixin B sulfate (PMBS) and 100 to 4000 μM PLP. After sealing the plates with aluminum/polypropylene laminate heat seal tape (Velocity 11, Menlo Park, CA, Cat #06643-001), they were shaken vigorously for 2 hours at room temperature. Cell debris was pelleted by centrifugation (4000 RPM, 10 min., 4° C.) and the clear supernatant assayed directly or stored at 4° C. until use.

For screening in methanol or DMSO at pH 7.5, with early-stage engineered transaminases (i.e., early-stage "evolvants"), a 10 μL aliquot of a solution of ketoamide substrate (40 mg/mL) in methanol or DMSO was added to each well of a Costar® deep well plate, followed by addition of 90 μL of 1.1 M isopropylamine hydrochloride using a Biomek NXp robotic instrument (Beckman Coulter, Fullerton, CA). This was then followed by addition of 100 μL of the recovered lysate supernatant, also performed using the Biomek NXp, to provide a reaction comprising of 2 mg/ml ketoamide substrate, 500 mM isopropyl amine hydrochloride, 50 mM triethanolamine pH 7.5, and 5% methanol or DMSO (v/v). The plates were heat-sealed with aluminum/polypropylene laminate heat seal tape (Velocity 11, Menlo Park, CA, Cat #06643-001) at 175° C. for 2.5 seconds and then shaken overnight (at least 16 hours) at 30° C. Reactions were quenched by the addition of 1 ml acetonitrile using a Phoenix Liquid Handling System (Art Robbins Instruments, Sunnyvale, CA). Plates were resealed, shaken for 5 min, and then centrifuged at 4000 rpm for 10 min. A 200 μL aliquot of the cleared reaction mixture was transferred to a new shallow well polypropylene plate (Costar #3365), sealed and analyzed as described in Example 4.

For screening in 25% DMSO at pH 8.5 with late-stage engineered transaminases (i.e., late-stage "evolvants"), a 50 μL aliquot of a solution of ketoamide substrate (400 mg/mL) in dimethyl sulfoxide (DMSO) was added to each well of a Costar® deep well plate, followed by addition of 50 μL of 4 M isopropylamine hydrochloride using a Biomek NX robotic instrument (Beckman Coulter, Fullerton, CA). This was then followed by addition of 100 μL of the recovered lysate supernatant, also performed using the Biomek NX, to provide a reaction comprising of 100 mg/ml ketoamide substrate, 1 M isopropyl amine hydrochloride, 50 mM triethanolamine pH 8.5, and 25% DMSO (v/v). The plates were heat-sealed with aluminum/polypropylene laminate heat seal tape (Velocity 11, Menlo Park, CA, Cat #06643-001) at 175° C. for 2.5 seconds and then shaken overnight (at least 16 hours) at 45° C. Reactions were quenched by the addition of 1 ml acetonitrile using a Phoenix Liquid Handling System (Art Robbins Instruments, Sunnyvale, CA). Plates were resealed, shaken for 5 min, and then centrifuged at 4000 rpm for 10 min. A 10 μL aliquot of the cleared reaction mixture was transferred to a new shallow well polypropylene plate (Costar #3365) containing 190 μL acetonitrile, sealed and analyzed as described in Example 4.

For screening in 50% DMSO at pH 8.5 with late-stage engineered transaminases (i.e., late-stage "evolvants"), a 100 μL aliquot of a solution of ketoamide substrate (100 mg/mL) in dimethyl sulfoxide (DMSO) was added to each well of a Costar® deep well plate, followed by addition of 50 μL of 4 M isopropylamine hydrochloride using a Biomek NX robotic instrument (Beckman Coulter, Fullerton, CA). This was then followed by addition of 50 μL of the recovered lysate supernatant, also performed using the Biomek NX, to provide a reaction comprising of 50 mg/ml ketoamide substrate, 1 M isopropyl amine hydrochloride, 50 mM triethanolamine pH 8.5, and 50% DMSO (v/v). The plates were heat-sealed with aluminum/polypropylene laminate heat seal tape (Velocity 11, Menlo Park, CA, Cat #06643-001) at 175° C. for 2.5 seconds and then shaken overnight (at least 16 hours) at 45° C. Reactions were quenched by the addition of 1 ml acetonitrile using a Phoenix Liquid Handling System (Art Robbins Instruments, Sunnyvale, CA). Plates were resealed, shaken for 5 min, and then centrifuged at 4000 rpm for 10 min. A 10 μL aliquot of the cleared reaction mixture was transferred to a new shallow well polypropylene plate (Costar #3365) containing 190 μL acetonitrile, sealed and analyzed as described in Example 4.

The transaminase of SEQ ID NO:2, expressed as in Examples 1 and 2 exhibited no detectable activity on the ketoamide substrate using the detection methods of Example 4. Variants of the *Arthrobacter* sp. KNK168 transaminase capable of converting ketoamide substrate to sitagliptin were identified using the approaches and procedures disclosed above. Multiple iterations of these processes, in which one or more improved isolates from one round were used as the starting material for subsequent rounds of mutagenesis and screening, were used to develop or "evolve" *Arthrobacter* sp. KNK168 transaminase variants with an improved ability to reduce ketoamide substrate stereoselectively to sitagliptin.

Example 6: Stereoselective Transamination in Methanol of Ketoamide Substrate by Engineered Transaminases Designated "+" in Table 2 Derived from *Arthrobacter* sp. KNK168 Transaminase Improved transaminases designated "+" in Table 2 derived horn *Arthrobacter* sp. KNK168 transaminase were evaluated at preparative scale in DMSO as follows. A 500 μL solution of transaminase variant (20 mg/mL) in 100 mM triethanolamine-chloride buffer pH 7.5 with 250 μM pyridoxal 5'-phosphate was added to 5 mL reaction vial equipped with a magnetic stir bar. Subsequently, 450 μL of 1.1 M isopropylamine hydrochloride, followed by 50 μL of a solution of ketoamide substrate (40 mg/mL) in DMSO was added to the transaminase solution. The reaction was stirred at 22° C. and monitored by HPLC analysis of samples taken periodically from the reaction mixture (see Example 4 for analytical conditions). Table 2 provides the SEQ ID NO. corresponding to transaminase variants designated "+", the number of amino acid residue differences from the wild-type transaminase, and activity of each toward ketoamide substrate relative to that of the enzyme having the amino acid sequence of SEQ ID NO: 4.

For many engineered transaminases, conversion of ketoamide substrate to sitagliptin can also be achieved using amino group donors such as D-alanine, 3-aminobutyric acid, or α-methylbenzylamine at a suitable concentration.

Example 7: Stereoselective Transamination in Methanol of Ketoamide Substrate by Engineered Transaminases Designated "++" in Table 2 Derived from *Arthrobacter* sp. KNK168

Improved transaminases designated "++" in Table 2 derived from *Arthrobacter* sp. KNK168 variants were evaluated at preparative scale in methanol as follows. A 500 μL solution of transaminase variant (20 mg/mL) in 100 mM triethanolamine-chloride buffer pH 7.5 with 250 μM pyridoxal 5'-phosphate was added to 5 mL reaction vial equipped with a stir bar. Subsequently, 450 μL of 1.1 M isopropylamine hydrochloride, followed by 50 μL of a solution of ketoamide substrate (40 mg/mL) in methanol was added to the transaminase solution. The reaction was stirred at 22° C. and monitored by HPLC analysis of samples taken periodically from the reaction mixture (see Example 4 for analytical conditions). Table 2 provides the SEQ ID NO. corresponding to transaminase variants designated "++", the number of amino acid residue differences from the wild-type transaminase, and activity of each toward ketoamide substrate relative to that of the enzyme having the amino acid sequence of SEQ ID NO: 4.

Example 8: Stereoselective Transamination in Methanol of Ketoamide Substrate by Engineered Transaminases Designated "+++" in Table 2 Derived from *Arthrobacter* sp. KNK168

Improved transaminases designated "+++" in Table 2 derived from *Arthrobacter* sp. KNK168 variants were evaluated at preparative scale in methanol as follows. A 500 μL solution of transaminase variant (20 mg/mL) in 100 mM triethanolamine-chloride buffer pH 7.5 with 250 μM pyridoxal 5'-phosphate was added to 5 mL reaction vial equipped with a stir bar. Subsequently, 450 μL of 2.2 M isopropylamine hydrochloride, followed by 50 μL of a solution of ketoamide substrate (100 or 200 mg/mL) in methanol was added to the transaminase solution. The reaction was stirred at 30° C. and monitored by HPLC analysis of samples taken periodically from the reaction mixture (see Example 4 for analytical conditions). Table 2 provides the SEQ ID NO. corresponding to transaminase variants designated "+++", the number of amino acid residue differences from the wild-type transaminase, and activity of each toward ketoamide substrate relative to that of the enzyme having the amino acid sequence of SEQ ID NO: 22.

Example 9: Stereoselective Transamination in Methanol of Ketoamide Substrate by Engineered Transaminases Designated "++++" in Table 2 Derived from *Arthrobacter* sp. KNK168

Improved transaminases designated "++++" in Table 2 derived from *Arthrobacter* sp. KNK168 variants were evaluated at preparative scale in methanol as follows. A 500 μL solution of transaminase variant (20 mg/mL) in 100 mM triethanolamine-chloride buffer pH 8.5 with 250 μM pyridoxal 5'-phosphate was added to 5 mL reaction vial equipped with a stir bar. Subsequently, 400 μL of 2.5 M isopropylamine hydrochloride, followed by 100 μL of a solution of ketoamide substrate (200 mg/mL) in methanol was added to the transaminase solution. The reaction was stirred at 45° C. and monitored by HPLC analysis of samples taken periodically from the reaction mixture (see Example 4 for analytical conditions). Table 2 provides the SEQ ID NO. corresponding to transaminase variants designated "++++", the number of amino acid residue differences from the wild-type transaminase, and activity of each toward ketoamide substrate relative to that of the enzyme having the amino acid sequence of SEQ ID NO: 48.

Example 10: Stereoselective Transamination in DMSO of Ketoamide Substrate by Engineered Transaminases Designated "+++++" in Table 2 Derived from *Arthrobacter* sp. KNK168

Improved transaminases designated "+++++" in Table 2 derived from *Arthrobacter* sp. KNK168 variants were evaluated at preparative scale in DMSO as follows. A 250 μL solution of transaminase variant (20 mg/mL) in 100 mM triethanolamine-chloride buffer pH 8.5 with 250 μM pyridoxal 5'-phosphate was added to 5 mL reaction vial equipped with a stir bar. Subsequently, 500 μL of 2 M isopropylamine hydrochloride, followed by 250 μL of a solution of ketoamide substrate (200 mg/mL) in DMSO was added to the transaminase solution. The reaction is stirred at 45° C. and monitored by HPLC analysis of samples taken periodically from the reaction mixture (see Example 4 for analytical conditions). Table 2 provides the SEQ ID NO. corresponding to transaminase variants designated "+++++", the number of amino acid residue differences from the wild-type transaminase, and activity of each toward ketoamide substrate relative to that of the enzyme having the amino acid sequence of SEQ ID NO: 58.

Example 11: Stereoselective Transamination in DMSO of Ketoamide Substrate by Engineered Transaminases Designated "++++++" in Table 2 Derived from *Arthrobacter* sp. KNK168

Improved transaminases designated "++++++" in Table 2 derived from *Arthrobacter* sp. KNK168 variants were evaluated at preparative scale in DMSO as follows. A 250 μL solution of transaminase variant (8 mg/mL) in 100 mM triethanolamine-chloride buffer pH 8.5 with 4000 μM pyridoxal 5'-phosphate was added to 5 mL reaction vial equipped with a stir bar. Subsequently, 250 μL of 4 M isopropylamine hydrochloride, followed by 500 μL of a solution of ketoamide substrate (100 mg/mL) in DMSO was added to the transaminase solution. The reaction is stirred at 45° C. and monitored by HPLC analysis of samples taken periodically from the reaction mixture (see Example 4 for analytical conditions). Table 2 provides the SEQ ID NO. corresponding to transaminase variants designated "++++++", the number of amino acid residue differences from the wild-type transaminase, and activity of each toward ketoamide substrate relative to that of the enzyme having the amino acid sequence of SEQ ID NO: 104.

Example 12: Process I for Conversion of Ketoamide Substrate to Sitagliptin

The following example illustrates a large scale process used to increase conversion of substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine. This process uses nitrogen sparging to remove the acetone co-product and increase the conversion of substrate to product. The addition of isopropylamine in water helps keep the volume constant and maintain the pH of the reaction.

The large scale process contains the following reaction components:

| | |
|---|---|
| Substrate Ketoamide: | 20 g (98%) (48.2 nmole) |
| Isopropylamine-HCl: | 18.44 g (193 nmole) |
| Pyridoxal phosphate PLP: | 200 mg (98%) (0.79 nmole) |
| Transaminase (SEQ ID NO: 86): | 2.2 g |
| 0.1M triethanolamine pH 8.5: | 140 mL |
| DMSO: | 20 mL + 40 mL |
| 4M iPr amine (free base): | 38.5 mL |

Process. To a 500 mL three neck round bottom (RB) flask with 4-baffles and fitted with stirrer, pH probe, temp, probe, needle for nitrogen sparge, and vacuum needle was added 18.25 g of isopropylamine hydrochloride (4 equiv.) followed by 200 mg of pyridoxal 5'-phosphate hydrate (vitamin B6). This was dissolved in 140 mL of pH 8.5, 0.1 M triethanolamine buffered water. DMSO (20 ml) was added followed by 2 g of transaminase enzyme (SEQ ID NO: 86) powder. The solution was brought to 45° C. and the pH was again adjusted to 8.5 with 4 M aqueous isopropylamine. After this stabilized (~5 min.), a solution of 20 g substrate dissolved in 40 mL of DMSO was added over 3 h. During the addition, and throughout the reaction, pH steadily dropped. The pH was controlled by continuous addition of 4 M aqueous isopropylamine when pH decreased by more than 0.1 units. In addition, nitrogen was sparged through the reaction after 2 h until 12 h. After 21 h, the conversion was at 93%. A total of 38.5 mL of 4M isopropyl amine (3.056 equiv.) was added to the reaction during the process. The pH control unit had a thermocouple, pH probe, and 4 M isopropylamine in water to control pH.

A substrate-product eneamine adduct impurity present in the product mixture (retention time of 4.1 min under the separation conditions described below) was destroyed by acidifying the mixture to pH 2.0 with 10.5 mL 6 N HCl followed by stirring for 1 h at 45° C. Subsequently, 6 g Celite was added, stirred another hour, and then filtered through a Celite pad (85 mm ID frit, 10 mm thick pad of wetted Celite) with agitated washings (4×30 mL) of water/DMSO (90/10 with 1 drop 6 N HCl). Assays show a yield of 91% sitagliptin and 7% substrate ketoamide.

The product was further processed by adding 200 mL isopropyl acetate (IPac) followed by 32 mL 5 N NaOH with stirring until the pH was ~11. Layers were separated (35 min. settling with emulsion in organic layer) and extracted aqueous layer with another 200 mL isopropyl acetate. A final extraction was carried out with an additional 100 mL of isopropyl acetate. All three isopropyl acetate layers were combined and allowed to settle for 30 min and the residual water drained off. The product in the organic layer was then washed with 150 mL brine (settles in <1 h), separated and dried with $Na_2SO_4$, and then filtered. The solvent was switched to isopropanol (66.29 g isopropanol (IPA) solution). Assay of the final product shows the following:

26.8 wt. % sitagliptin (17.73 g).

1.89 wt. % ketoamide substrate (1.25 g).

~60.3 mL IPA

The HPLC conditions for separation of the product mixture were as follows:

Column: Zorbax Eclipse Plus C18, 4.6×50 mm, 1.8 um

| Gradient: min | $H_2O$ (0.1 % $H_3PO_4$)/$CH_3CN$ |
|---|---|
| 0 | 90/10 |
| 5 | 5/95 |
| 6 | 5/95 |
| 6.01 | 90/10 |
| 8 | stop |

Flow: 1.5 mL/min

Column Temperature: 25° C.

Sample volume: 5 μL

Detector: UV @ 210 nm

Samples for HPLC analysis were prepared in 0.2 mg/mL in 1/1 $H_2O$ (0.1% $H_3PO_4$)/$CH_3CN$. The retention times under the chromatographic conditions above were as follows:

Sitagliptin: 2.2 min

Ketoamide substrate: 3.2 min

Ketoamide substrate (enol): 3.9 min

Substrate-product eneamine: 4.1 min.

The purging with nitrogen gas removes acetone, the product of the transamination reaction, thereby shifting the equilibrium of the transaminase catalyzed reaction towards product formation, and hence a higher percentage conversion of substrate to product. In addition, the continual addition of isopropylamine not only maintains the pH of the reaction condition, but also replenishes the amino group donor lost in the transamination reaction. Although the transaminase polypeptide having SEQ ID NO: 86 was used in this process, it is to be understood that this exemplary process can employ any of the subsequent engineered transaminases disclosed herein.

Example 13: Process II for Increasing Conversion of Ketoamide Substrate to Sitagliptin The following example illustrates a second large scale process used to increase conversion of substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine. This process uses a vacuum to remove the acetone product and increase the conversion of substrate to product. As in the preceding example, addition of isopropylamine in water helps keep the volume constant and maintain the pH of the reaction.

Materials.

| Reaction component | Amount | Mole Equivalents |
|---|---|---|
| Ketoamide substrate: | 1000 g (96%) (2.36 mole) | 1.0 |
| Isopropylamine-HCL: | 903 g (9.45 mole) | 4.0 |
| Pyridoxal phosphate PLP: | 10 g (98%) (0.04 mole) | 0.017 |
| Transaminase (SEQ ID NO: 102): | 50.0 g | |
| Triethanolamine: | 104 g | |
| DMSO: | 1.5 L + 2 L | |
| 4M aqueous isopropylamine (free base): | 157 mL | |

Equipment for the process has the following features: a pH control unit that has thermocouple, a pH probe, and reservoir of 4M isopropylamine in water to control pH. The reaction vessel is connected to a vacuum line and corresponding controller (set to 375 torr) and ReactIR probe (Metter Toledo, Maryland, USA) to measure acetone and product formation.

Process. A 22 L mechanically stirred round bottom (RB) flask was fitted with a ReactIR probe, a base feed line connected to a reservoir of 4 M aqueous isopropylamine, a ketoamide feed line connected to a reservoir of ketoamide substrate, a pH probe, and a vacuum line to a control box and a trap. The flask was charged with 900 g of isopropylamine hydrochloride followed by addition of 6.4 L deionized water and 93 mL of triethanolamine (2 m/s tip speed) and 10 g pyridoxal 5'-phosphate (pH 8.4) was added. This was followed by charging of the flask with 50 g of dissolved transaminase polypeptide having SEQ ID NO: 102. After 10 min. of stirring at RT, 1.5 L of DMSO was added over 30 min, and the reactor was warmed to 40° C. After the temperature stabilized, the pH probe was exchanged for a temperature probe, and the pH maintained at pH 8.5 with a pH controller and 4 M isopropylamine solution. Ketoamide substrate (1 Kg) was dissolved in 2 L of DMSO and placed into a 5 L addition funnel. Vacuum (~500 torr initially then 375 torr overnight after addition) was applied to the reaction vessel, and the ketoamide solution was added to the reactor over 4 hrs (667 mL/h). A total of 1.45 equiv. of isopropylamine was added after 25 h. There was about 94% conversion of substrate to product.

After allowing the reaction to proceed for 1 day, 580 mL 5 N HCl was added to the reaction solution until pH 2 and the solution stirred for 2 hrs at 45° C. The solution was filtered through a wide diameter Buchner funnel using two layers of cotton towel resulting in 12.3 kg of filtrate. The filtrate residue was agitated in 5% DMSO in 0.01 N HCl and then rinsed with an additional 3×2 L of 5% DMSO in 0.01 N HCl (6.6 kg total). The residue was placed in aqueous acidic solution, washed (~18 L total) into an extractor and then placed in 9 L of isopropyl acetate. The pH was adjusted to 10 with 5 N NaOH (1.4 L), the solution agitated at 165 RPM in 50 L ChemGlass vessel #1, the layers allowed to settle for about 10 min, and the isopropyl acetate separated out. The solution was extracted again with 9 L of isopropyl acetate, and the extracted isopropyl acetate layers were combined and allowed to settle for 20 h. The isopropyl acetate layers were washed with 6 L of brine (5.9 kg). The IP Ac solution was assayed and contained 861 g sitagliptin. Solvent was switched from IP Ac (861 g in 19 L IP Ac, 90% assay yield) to IPA on rotary vacuum evaporator by feeding over 1 h at 30° C. and concentrating to 50% volume. At this point, the sitagliptin free base precipitated out of solution. 2 L of 1% water in IPA was added to dissolve the precipitate. 8 L of 1% water in IPA over 1 h was added at 35-40° C. bath temperature. Since additional precipitates form, additional 400 mL water was added to dissolve the precipitate. The solution was allowed to sit on a rotary vacuum evaporator overnight, and then transferred to another round bottom flask along with an additional 2 L of 1% water in IPA. Concentration gave 2.5746 kg of an IPA/water solution of sitagliptin.

Example 14: Preparation of Sitagliptin Phosphate Monohydrate

Preparation of sitagliptin phosphate monohydrate is illustrated as follows:

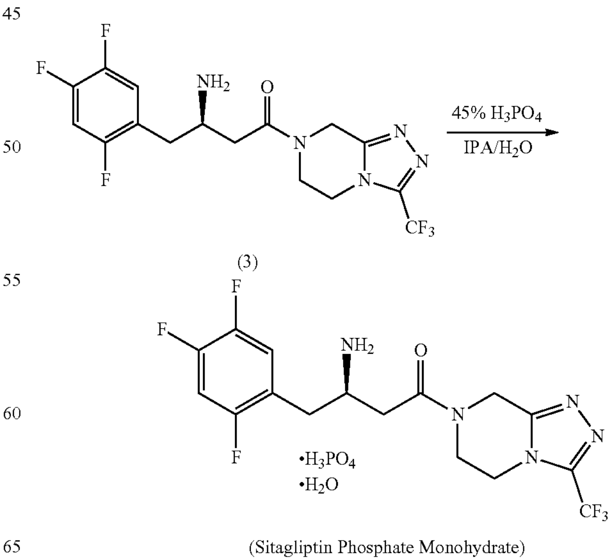

(Sitagliptin Phosphate Monohydrate)

Materials for the preparation of the phosphate monohydrate salt of sitagliptin is as follows:

| Reaction component | Amount | Mole Equivalents |
|---|---|---|
| Crude 3 | 757 g (1.86 mole) | 1.0 |
| 45% w/w $H_3PO_4$ | 411 g (1.89 mole) | 1.02 |
| water | 347 + 491 + 100 mL | 0.017 |
| Isopropanol | 1.63 + 1.36 + 0.17 + 0.5 + 0.5 + 1.65 L | |
| Seed | 5 g | 0.005 |
| 88/12 isopropanol/water | 1.4 L | |

Process. To a solution containing 757 g Crude 3 in 1630 mL isopropanol and 347 mL water was added 1.36 L isopropanol followed by 491 mL of deionized water. The solution was transferred to 20 L stirred vessel, and then charged with 411 g of 45% w/w $H_3PO_4$ (Fisher 85%) and 172 mL IPA. Solution was heated to 72-80° C. to dissolve initial phosphate salt and charged with an additional 100 mL of water and 500 mL isopropanol to completely dissolve the phosphate salt. Solution was cooled to 62-66° C. and seeded with 5 g of pure sitagliptin phosphate. Reaction was allowed to sit for 3 h at 60-65° C., and then cooled to 20-25° C. over 5 h and then additionally overnight. The reaction was charged with 2.65 L isopropanol over 2 h (solution is ~6:1 isopropanol/water) and allowed to sit for 1 h at RT and 2 h at 2° C. The material was passed through a filter that was prepared by wetting with 88/12 isopropanol/water. The resulting cake was washed with a total of 1.4 L 88/12 isopropanol/water and dried under atmosphere for about 3 h, and then transferred to a tray to dry at ~40° C. in vacuum oven with nitrogen sweep (200 torr) for 3 days providing 966 g sitagliptin phosphate hydrate. The material met (or exceeded) all purity specifications for manufactured sitagliptin phosphate hydrate and showed no residual solvent, enzyme (<18 ppm), PLP co-factor (<0.1 ppm), or endotoxin (<0.05 ng).

Example 15: Process III for Increasing Conversion of Ketoamide Substrate to Sitagliptin The following example illustrates a third large scale process used to increase conversion of substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine. Generally, the process uses the same equipment and conditions as described in Example 12 but with a higher concentration of DMSO and substrate.

Process: The reaction was run in a vessel fitted with a mechanical stirrer, temperature probe, pH probe, and a base addition line. The base addition line was used to control pH between 8.6 and 8.4 using a feed of 4 M isopropylamine free base in water. To the vessel was added 1.92 L water, followed by 109 mL (0.82 mol, 0.33 equiv.) triethanolamine and 1.64 L (6.56 mol, 2.67 equiv.) of 4 M isopropylamine solution. The pH was then adjusted to 8.5 using 12 N HCl (424 mL). The reactor was then charged with 6.7 g (0.027 mol, 0.011 equiv.) of PLP followed by 40 g of the transaminase polypeptide having SEQ ID NO: 110 and the mixture was carefully dissolved with gentle agitation. The vessel was placed on the reactor block with the temperature probe, base addition line, pH probe, and stirrer set to 400 RPM (Note: pH control loop is off at this point). Next, 2.22 L of DMSO was added into the stirring solution and the reactor was heated to 45° C. When the temperature stabilized, the pH control loop was turned on and adjusted to pH to 8.5 (pH controlled with 4 M isopropylamine in water). At this point, stirring was increased to 600 RPM, but tip speed is kept below 2 m/s to avoid vortexing. Then, 1.0 kg (corrected weight is 1 kg as received ketoamide is typically 96-98 wt % as a hemi-hydrate; 2.46 mol, 1.00 equiv.) of ketoamide was dissolved into 1.11 L of DMSO. This DMSO/ketoamide solution was then added to the reactor over 2-3 h. The reactor was then stirred at 45° C. and with the pH maintained between 8.6-8.4 for another ~13 h with acetone removal being accomplished with 300 torr vacuum and 2 fps nitrogen sweep. After ~15 h total reaction time (1.3-2.0 equiv. isopropylamine uptake), the reaction was at 90-95% conversion as judged by reverse phase HPLC analysis.

As described below, either a filtration or a direct extraction work-up procedure can be used to prepare the product for downstream processing.

Filtration work-up: The pH control loop was turned off and 13 g of solka-floc was added to the vessel followed by 12 M HCl until pH 2-3. The reaction was then aged 1-2 h at 45° C. and 1000 RPM. The slurry was then passed through a filter (e.g., fritted plastic Buchner with filter paper on 1 kg scale, or sparkle filter with no recycle loop on pilot plant scale). The vessel and filter was rinsed with 1 L of 0.01 N HCl. To this aqueous acidic filtrate was then added 3 L of IP Ac and the pH of the aqueous phase was then adjusted to pH 11 with 19 N NaOH. The layers were agitated with stirring, and then allowed to settle and separated (mild heat or vacuum accelerates phase separation). This was repeated twice more with 3 L of IP Ac and the combined organics were then washed with 3 L of brine (at pH 11). The resulting IP Ac solution of the sitagliptin free base was then assayed for yield (typically 88-92% assay yield; 882-922 g) and solvent switched to IPA for downstream processing to sitagliptin phosphate monohydrate.

Direct extraction work-up: The pH control loop was turned off and 12 M HCl was added until pH 2-3. The reaction was then aged 1-2 h at 45° C. and 1000 RPM. The batch was cooled to RT and then 3 L of IPA was added, followed by 3 L of IP Ac. The pH of the aqueous layer was then adjusted to 11 with 19 N NaOH. The mixture was agitated at 20-45° C. (heat may be used to break the emulsion), and then allowed to settle and separate. The IPAc/IPA layer was set aside and the aqueous layer was extracted with 3 L of 80/20 (vol/vol) IPAc/IPA. The combined IPAc/IPA extracts were then washed with 3 L of brine. The resulting IPAc/IPA solution of the sitagliptin free base was then assayed for yield (typically 87-90% assay yield, 872-902 g) and solvent switched to IPA for downstream processing to sitagliptin phosphate monohydrate Example 16: Process IV for Increasing Conversion of Ketoamide Substrate to Sitagliptin The following example illustrates a fourth large scale process used to increase conversion of the ketoamide substrate to the sitagliptin freebase product and the subsequent preparation of the sitagliptin phosphate. Generally, the process uses the same equipment conditions as described in Examples 12, 14, and 15 but with alterations as detailed below.

A buffer solution was prepared by combining 0.59 L 4M isopropyl amine solution, 0.67 L water, and 39 mL triethanolamine at 0-35° C. The pH of the buffer was adjusted to 8.4-9.2 at 20-25° C. using 12N hydrochloric acid. To this mixture was charged 1.22 g PLP and 16.25 g of the transaminase polypeptide of SEQ ID NO: 110 at 15-25° C. The PLP and enzyme were dissolved with agitation. Next, 0.72 L DMSO was charged to the batch at 15-46° C. over a minimum of 30 minutes. The enzyme mixture was then heated to 44-46° C. and then adjusted to pH 8.4-8.7 with 4M isopropyl amine solution. Until the enzyme mixture was quenched following reaction, the pH was monitored and 4M isopropyl amine solution was charged as necessary to maintain the pH within the range of 8.4-8.7.

The ketoamide substrate, 4-oxo-4-[3-(trifluoromethyl)-5, 6-dihydro[1,2,4]triazolo[4,3-a]pyrazin-7(8H)-yl]-1-(2,4,5-trifluorophenyl)butan-2-one (406.28 g, 1.00 mole) was dissolved into 0.48 L of DMSO, and this DMSO/ketoamide solution was added to the enzyme mixture over 2-8 hours. This enzyme mixture was then allowed to react at 44-46° C. and pH 8.4-8.7 for another 7-22 hours. During both the DMSO/ketoamide solution addition and the subsequent reaction, the pressure of the reactor was varied as necessary to evaporate acetone and thereby push the reaction to formation of product sitagliptin free base. In addition, during the course of the reaction, 4M isopropyl amine solution was charged (typically a minimum of 0.25 L, or 1.0 molar equivalent) as necessary in order to maintain the pH at 8.4-8.7.

The reaction mixture was quenched by charging 65 g solka floe at 44-46° C. Following the solka floe charge, 12N hydrochloric acid was charged to the batch until pH 2-3 is reached. The mixture was stirred at 44-46° C. and pH 2-3 for at least 3 hours. The mixture was then filtered at 44-46° C., and the waste cake washed with 0.01N hydrochloric acid (1.02 L-4.47 L). The combined filtrate and 0.01N hydrochloric acid wash was cooled to 15-25° C., and then 2.44 L of isopropyl acetate (IPAc) was added. The apparent pH was then adjusted to 10.5-11.5 with 19N sodium hydroxide. The mixture was then agitated at 15-40° C., settled, and separated. The top, organic layer was set aside and the lower, aqueous layer was then extracted with 1.22 L of IP Ac at 15-25° C. The two organic extracts were then combined and washed with water (0.20 L-1.23 L) at 15-40° C. The final organic layer yielded 4.07 L of a sitagliptin freebase crude stream at 100 g/L (407.31 g, 1.00 mole) that was used in the preparation of the sitagliptin phosphate monohydrate.

The 4.07 L of sitagliptin freebase crude stream was concentrated under vacuum to 1.68 L at 20-35° C. and then solvent switched to isopropanol using a minimum of 2.52 L of isopropanol. To this solution was charged a minimum of 0.27 L water to dissolve all solids. The addition of water enhances formation of the monohydrate at the start of the crystallization. Aqueous phosphoric acid (1.02 mole) was added to this solution, then heated to dissolve.

The solution then was cooled to 62-68° C., seeded with 2.62 g of milled sitagliptin phosphate monohydrate (e.g., mean volume of 10-20 microns with 95$^{th}$ percentile between 25-45 microns as determined by Microtrac analysis) and allowed to age for 3-6 hours at 62-68° C. The slurry was cooled to 20-25° C. over a minimum of 2 hours. To the slurry was charged 0.48 L of isopropanol over a minimum of 2 hours, while maintaining temperature at 20-25° C. The slurry was then cooled to −15° C. to 20° C. over a minimum of 2 hours. The slurry was then filtered at −15° C. to 20° C. and the wetcake washed with aqueous isopropanol (minimum water content of 8 wt %). The wetcake was dried at a maximum temperature of 45° C. in vacuo to yield sitagliptin phosphate monohydrate.

Example 17: Process V for Increasing Conversion of Ketoamide Substrate to Sitagliptin The following example illustrates a fifth large scale process used to increase conversion of the ketoamide substrate to the sitagliptin freebase product and the subsequent preparation of the sitagliptin phosphate. Generally, this large scale process uses the same equipment and conditions as described in Example 16 but with some alterations as detailed below.

Buffer solution was prepared by combining 50.68 L 4M isopropyl amine solution, 58.1 L water, and 3.36 L triethanolamine at 20-25° C. The pH of the buffer was then adjusted to 8.8-9.2 at 20-25° C. using 12N hydrochloric acid. To the batch mixture was charged 0.11 kg of PLP, and then 1.40 kg of the transaminase enzyme of SEQ ID NO: 110 at 20-25° C. The PLP and enzyme were dissolved with agitation (confirmed after 30 min). Next, 61.76 L of DMSO was charged to the batch at 20-46° C. The batch was then heated to 44-46° C. and once at temperature, 4M isopropyl amine solution was charged to adjust the pH to 8.4-8.7.

The ketoamide substrate (35.00 kg) was dissolved into 41.18 L of DMSO, and this DMSO/ketoamide solution added to the batch over 2-3 hours. The batch was then allowed to react at 44-46° C. and pH 8.4-8.7 for another 12-22 hours. During both the DMSO/ketoamide solution addition and the subsequent aging, the pressure of the reactor was varied in order to remove acetone (typical pressure conditions for acetone removal: ~325-350 mm Hg vacuum and ~3-6 scfm nitrogen headspace sweep). In addition, during the course of the reaction, 4M isopropyl amine solution was charged as necessary in order to maintain the pH at 8.4-8.7. Typical end of reaction conversion results are 88-93% after 15-17 hours of total reaction time, which includes the DMSO/ketoamide transfer time.

The reaction was quenched by charging 5.60 kg solka floe slurry in 42 L water. Following the solka floe charge, 12N hydrochloric acid was charged to the batch until pH 2-3 was reached. The reaction was stirred at 44-46° C. and pH 2-3 for 3 hours. The batch was then filtered at 44-46° C., and the waste cake washed with 154 L of 0.01N hydrochloric acid solution.

The combined filtrate and wash solution was cooled to 15-25° C., and then 210 L of isopropyl acetate (IPAc) added. The apparent pH of the batch was then adjusted to 10.5-11.5 with 19N sodium hydroxide. The mixture was then agitated at 15-25° C., settled, and separated (Extraction #1). The top, organic layer was set aside and the lower, aqueous layer was then extracted with 105 L of IP Ac at 15-25° C. (Extraction #2). The two organic extracts were then combined and washed with 17.50 L water at 32-38° C. (Extraction #3). The final organic layer yielded 29.44 assay kg of sitagliptin freebase crude stream (~85.9% assay yield).

The freebase crude stream, 294.40 L at 100 g/L (29.44 kg, 72.28 mole), was concentrated under vacuum (30-60 mmHg) to 121.59 L at 20-35° C. The batch was solvent switched to isopropanol using 182.39 L of isopropanol. To the batch was charged 19.72 L of water to dissolve all solids. Then, 15.87 kg of 45 wt % aqueous phosphoric acid was added to the batch, which was heated to 72-80° C. to dissolve. The batch solution was cooled to 62-66° C. and seeded with 0.19 kg pin milled sitagliptin phosphate monohydrate. The batch was aged for 3 hours at 62-66° C. and then cooled to 20-25° C. over 2 hours. To the batch was charged 34.40 L of isopropanol over 2 hours, while maintaining batch temperature at 20-25° C. The batch was then cooled to a −15° C. to 0° C. over 2 hours. The slurry was then filtered at −15° C. to 0° C. and the wetcake washed with 70.05 L aqueous isopropanol (minimum of 8 wt % water). The wetcake was dried at 40° C. in vacuo to yield sitagliptin phosphate monohydrate (37.34 physical kg, ~98% yield).

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A recombinant transaminase polypeptide comprising an amino acid sequence at least 90% identical to SEQ ID NO: 2, wherein the amino acid sequence of the recombinant transaminase polypeptide further comprises a residue difference as compared to SEQ ID NO: 2 at residue position X65 and at residue position X81.

2. The recombinant transaminase polypeptide of claim 1, wherein said recombinant transaminase polypeptide is capable of converting 4-oxo-4-[3-(trifluoromethyl)-5,6-dihydro[1,2,4]triazolo[4,3-a]pyrazin-7 (8H)-yl]-1-(2,4,5-trifluorophenyl) butan-2-one ("ketoamide substrate") to (2R)-4-oxo-4-[3-(trifluoromethyl)-5,6-dihydro[1,2,4]triazolo[4,3-a]pyrazin-7 (8H)-yl]-1-(2,4,5-trifluorophenyl) butan-2-amine ("product") under a defined reaction condition in the presence of an amino group donor isopropylamine to levels of the product detectable by HPLC-UV at 210 nm, where the reaction condition comprises about 2 g/L ketoamide substrate, about 0.5 M isopropylamine, about 22° C., about pH 7.5, about 5% DMSO, about 100 μM pyridoxal phosphate, and about 20 mg/mL of transaminase polypeptide.

3. The recombinant transaminase polypeptide of claim 2, wherein said recombinant transaminase polypeptide is capable of converting the ketoamide substrate to the product with an activity that is equal to or greater than the activity of the polypeptide of SEQ ID NO: 4 under the defined reaction condition.

4. The recombinant transaminase polypeptide of claim 2, wherein said recombinant transaminase polypeptide is capable of converting the ketoamide substrate to product in at least 90% enantiomeric excess.

5. The recombinant transaminase polypeptide of claim 2, wherein said recombinant transaminase polypeptide is capable of converting the ketoamide substrate to product in at least 99% enantiomeric excess.

6. The transaminase polypeptide of claim 1, wherein the amino acid sequence corresponds to the sequence of SEQ ID NO: 68, 70, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168.

7. The transaminase polypeptide of claim 1, wherein the amino acid sequence includes the following features: X69 is C or T; X122 is M or I; X223 is P; and X284 is G.

8. The transaminase polypeptide of claim 1, wherein the amino acid sequence includes the following features: X69 is C or T; X122 is M or I; X223 is P; and X284 is G.

9. The transaminase polypeptide of claim 1, wherein the amino acid sequence additionally comprises a residue difference as compared to SEQ ID NO:2 at one or more of the following residue positions: X4; X5; X8; X18; X25; X26; X27; X28; X30; X41; X42; X48; X49; X50; X54; X55; X60; X61; X62; X94; X96; X102; X117; X120; X124; X126; X136; X137; X138; X146; X148; X150; X152; X155; X156; X160; X163; X164; X169; X174; X178; X195; X199; X204; X208; X209; X211; X215; X217; X225; X230; X252; X269; X273; X282, X292; X297; X302; X306; X321; and X329.

* * * * *